US008038991B1

(12) United States Patent
Stankus et al.

(10) Patent No.: US 8,038,991 B1
(45) Date of Patent: Oct. 18, 2011

(54) HIGH-VISCOSITY HYALURONIC ACID COMPOSITIONS TO TREAT MYOCARDIAL CONDITIONS

(75) Inventors: John J. Stankus, Campbell, CA (US); Eugene Michal, San Francisco, CA (US); Mikael Trollsas, San Jose, CA (US); Brandon Katz, Saratoga, CA (US); Shubhayu Basu, Mountain View, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 925 days.

(21) Appl. No.: 11/933,922

(22) Filed: Nov. 1, 2007

Related U.S. Application Data

(63) Continuation-in-part of application No. 10/414,602, filed on Apr. 15, 2003.

(51) Int. Cl.
*C12N 5/00* (2006.01)
(52) U.S. Cl. .......................... 424/93.7; 424/530; 514/54
(58) Field of Classification Search ........................ None
See application file for complete search history.

(56) References Cited

U.S. PATENT DOCUMENTS

| | | | |
|---|---|---|---|
| 2,512,569 A | 6/1950 | Saffir | |
| 3,584,624 A | 6/1971 | de Ciutiis | |
| 3,780,733 A | 12/1973 | Martinez-Manzor | |
| 3,890,976 A | 6/1975 | Bazell et al. | |
| 4,141,973 A * | 2/1979 | Balazs ............................ 514/54 | |
| 4,617,186 A | 10/1986 | Schafer et al. | |
| 4,794,931 A | 1/1989 | Yock | |
| 4,818,291 A | 4/1989 | Iwatsuki et al. | |
| 4,842,590 A | 6/1989 | Tanabe et al. | |
| 5,000,185 A | 3/1991 | Yock | |
| 5,024,234 A | 6/1991 | Leary et al. | |
| 5,049,130 A | 9/1991 | Powell | |
| 5,092,848 A | 3/1992 | DeCiutiis | |
| 5,100,185 A | 3/1992 | Menke et al. | |
| 5,116,317 A | 5/1992 | Carson et al. | |
| 5,128,326 A | 7/1992 | Balazs et al. | |
| 5,171,217 A | 12/1992 | March et al. | |
| 5,202,745 A | 4/1993 | Sorin et al. | |
| 5,203,338 A | 4/1993 | Jang | |
| 5,270,300 A | 12/1993 | Hunziker | |
| 5,291,267 A | 3/1994 | Sorin et al. | |
| 5,306,250 A | 4/1994 | March et al. | |
| 5,321,501 A | 6/1994 | Swanson et al. | |
| 5,328,955 A | 7/1994 | Rhee et al. | |
| 5,336,252 A | 8/1994 | Cohen | |
| 5,354,279 A | 10/1994 | Hofling | |
| 5,365,325 A | 11/1994 | Kumasaka et al. | |
| 5,372,138 A | 12/1994 | Crowley et al. | |
| 5,380,292 A | 1/1995 | Wilson | |
| 5,437,632 A | 8/1995 | Engelson | |
| 5,455,039 A | 10/1995 | Edelman et al. | |
| 5,459,570 A | 10/1995 | Swanson et al. | |
| 5,464,395 A | 11/1995 | Faxon et al. | |
| 5,465,147 A | 11/1995 | Swanson | |
| 5,485,486 A | 1/1996 | Gilhousen et al. | |
| 5,499,630 A | 3/1996 | Hiki et al. | |
| 5,516,532 A | 5/1996 | Atala et al. | |
| 5,540,912 A | 7/1996 | Roorda et al. | |
| 5,546,948 A | 8/1996 | Hamm et al. | |
| 5,554,389 A | 9/1996 | Badylak et al. | |
| 5,575,815 A | 11/1996 | Slepian et al. | |
| 5,580,714 A | 12/1996 | Polovina | |
| 5,580,856 A | 12/1996 | Prestrelski et al. | |
| 5,588,432 A | 12/1996 | Crowley | |
| 5,621,610 A | 4/1997 | Moore et al. | |
| 5,642,234 A | 6/1997 | Altman et al. | |
| 5,655,548 A | 8/1997 | Nelson et al. | |
| 5,667,778 A | 9/1997 | Atala | |
| 5,676,151 A | 10/1997 | Yock | |
| 5,693,029 A | 12/1997 | Leonhardt | |
| 5,722,403 A | 3/1998 | McGee et al. | |
| 5,725,551 A | 3/1998 | Myers et al. | |
| 5,730,732 A | 3/1998 | Sardelis et al. | |
| 5,740,808 A | 4/1998 | Panescu et al. | |
| 5,749,915 A | 5/1998 | Slepian | |
| 5,785,689 A | 7/1998 | De Toledo et al. | |
| 5,810,885 A | 9/1998 | Zinger | |
| 5,811,533 A | 9/1998 | Gold et al. | |
| 5,827,313 A | 10/1998 | Ream et al. | |

(Continued)

FOREIGN PATENT DOCUMENTS

EP           0331584          9/1989

(Continued)

OTHER PUBLICATIONS

Abbott Medical Optics, website for HEALON(R) OVD, copyright 2010, accessed Dec. 15, 2010. URL:<http://www.abbottmedicaloptics.com/products/cataract/ovds/healon-viscoelastic> 2pages.*
Product Information Sheet for HEALON(R), from Abbott Medical Optics, copyright 2005. 1 page.*
Haynesworth et al, "Platelet Effects on Human Mesenchymal Stem Cells" Abstract, presented at Orthopaedic Research Society 48th Annual Meeting, Dallas, TX, Feb. 10-13, 2002. 2 pages.*
PCT International Preliminary Report on Patentability and Written Opinion dated Dec. 24, 2008 for PCT/US2007/013181, 11 pages.
Abbott Cardiovascular Systems in, PCT Search Report and Written Opinion dated Aug. 26, 2008 for PCT/US2007/016433.
Abbott Cardiovascular Systems in, PCT Search Report and Written Opinion dated Jul. 31, 2008 for PCT/US2007/024158.
Abbott Cardiovascular Systems in, PCT Search Report dated Feb. 12, 2008, PCT Appln No. PCT/US2007/013181, 17 pages.

(Continued)

*Primary Examiner* — Allison Ford
(74) *Attorney, Agent, or Firm* — Randy Shen; Blakely Sokoloff Taylor & Zafman LLP

(57) ABSTRACT

Embodiments of single component bioscaffolding systems formed of a hydrogel such as hyaluronic acid or salt thereof are described. The hyaluronic acid or salt thereof may be dissolved in a buffer, plasma, or combination thereof to minimize adverse immunogenic responses when applied to a treatment site. Additionally, the hydrogel component includes stem cells to facilitate angiogenesis or facilitate tissue repair and/or regeneration of ischemic tissue, particularly in compromised cardiac tissue. The bioscaffolding may also be formed on a stent or a cardiac medical device.

10 Claims, 35 Drawing Sheets

U.S. PATENT DOCUMENTS

| | | | |
|---|---|---|---|
| 5,843,156 A | 12/1998 | Slepian et al. |
| 5,874,500 A | 2/1999 | Rhee et al. |
| 5,879,713 A | 3/1999 | Roth et al. |
| 5,900,433 A | 5/1999 | Igo et al. |
| 5,906,934 A | 5/1999 | Grande et al. |
| 5,919,449 A | 7/1999 | Dinsmore |
| 5,935,160 A | 8/1999 | Auricchio et al. |
| 5,939,323 A | 8/1999 | Valentini et al. |
| 5,941,868 A | 8/1999 | Kaplan et al. |
| 5,957,941 A | 9/1999 | Ream |
| 5,968,064 A | 10/1999 | Selmon |
| 5,979,449 A | 11/1999 | Steer |
| 5,980,887 A | 11/1999 | Isner et al. |
| 5,981,568 A | 11/1999 | Kunz et al. |
| 5,984,908 A | 11/1999 | Davis et al. |
| 5,997,536 A | 12/1999 | Osswald et al. |
| 6,022,540 A | 2/2000 | Bruder et al. |
| 6,045,565 A | 4/2000 | Ellis et al. |
| 6,050,949 A | 4/2000 | White et al. |
| 6,051,071 A | 4/2000 | Charvet et al. |
| 6,051,648 A | 4/2000 | Rhee et al. |
| 6,056,744 A | 5/2000 | Edwards |
| 6,058,329 A | 5/2000 | Salo et al. |
| 6,060,053 A | 5/2000 | Atala |
| 6,071,305 A | 6/2000 | Brown et al. |
| 6,086,582 A | 7/2000 | Altman et al. |
| 6,093,177 A | 7/2000 | Javier, Jr. et al. |
| 6,099,563 A | 8/2000 | Zhong |
| 6,099,864 A | 8/2000 | Morrison et al. |
| 6,102,887 A | 8/2000 | Altman |
| 6,102,904 A | 8/2000 | Vigil et al. |
| 6,102,926 A | 8/2000 | Tartaglia et al. |
| 6,120,520 A | 9/2000 | Saadat et al. |
| 6,120,904 A | 9/2000 | Hostettler et al. |
| 6,127,448 A | 10/2000 | Domb |
| 6,133,231 A | 10/2000 | Ferrara et al. |
| 6,134,003 A | 10/2000 | Tearney et al. |
| 6,151,525 A | 11/2000 | Soykan |
| 6,152,141 A | 11/2000 | Stevens et al. |
| 6,153,428 A | 11/2000 | Gustafsson et al. |
| 6,159,443 A | 12/2000 | Hallahan |
| 6,162,202 A | 12/2000 | Sicurelli et al. |
| 6,175,669 B1 | 1/2001 | Colston et al. |
| 6,177,407 B1 | 1/2001 | Rodgers et al. |
| 6,179,809 B1 | 1/2001 | Khairkhahan et al. |
| 6,183,432 B1 | 2/2001 | Milo |
| 6,183,444 B1 | 2/2001 | Glines et al. |
| 6,187,330 B1 | 2/2001 | Wang et al. |
| 6,190,353 B1 | 2/2001 | Makower et al. |
| 6,191,144 B1 | 2/2001 | Isner |
| 6,193,763 B1 | 2/2001 | Mackin |
| 6,197,324 B1 | 3/2001 | Crittenden |
| 6,201,608 B1 | 3/2001 | Mandella et al. |
| 6,206,893 B1 | 3/2001 | Klein et al. |
| 6,206,914 B1 | 3/2001 | Soykan et al. |
| 6,207,180 B1 | 3/2001 | Ottoboni et al. |
| 6,210,392 B1 | 4/2001 | Vigil et al. |
| 6,217,527 B1 | 4/2001 | Selmon et al. |
| 6,217,554 B1 | 4/2001 | Green |
| 6,221,049 B1 | 4/2001 | Selmon et al. |
| 6,231,546 B1 | 5/2001 | Milo et al. |
| 6,235,000 B1 | 5/2001 | Milo et al. |
| 6,241,710 B1 | 6/2001 | VanTassel et al. |
| 6,251,104 B1 | 6/2001 | Kesten et al. |
| 6,283,947 B1 | 9/2001 | Mirzaee |
| 6,287,285 B1 | 9/2001 | Michal et al. |
| 6,290,729 B1 | 9/2001 | Slepian et al. |
| 6,296,602 B1 | 10/2001 | Headley |
| 6,299,604 B1 | 10/2001 | Ragheb et al. |
| 6,309,370 B1 | 10/2001 | Haim et al. |
| 6,312,725 B1 | 11/2001 | Wallace et al. |
| 6,315,994 B2 | 11/2001 | Usala et al. |
| 6,323,278 B2 | 11/2001 | Rhee et al. |
| RE37,463 E | 12/2001 | Altman |
| 6,328,229 B1 | 12/2001 | Duronio et al. |
| 6,331,309 B1 | 12/2001 | Jennings, Jr. et al. |
| 6,333,194 B1 | 12/2001 | Levy et al. |
| 6,334,872 B1 | 1/2002 | Termin et al. |
| 6,338,717 B1 | 1/2002 | Ouchi |
| 6,346,098 B1 | 2/2002 | Yock et al. |
| 6,346,099 B1 | 2/2002 | Altman |
| 6,346,515 B1 | 2/2002 | Pitaru et al. |
| 6,358,247 B1 | 3/2002 | Altman et al. |
| 6,358,258 B1 | 3/2002 | Arcia et al. |
| 6,360,129 B1 | 3/2002 | Ley et al. |
| 6,368,285 B1 | 4/2002 | Osadchy et al. |
| 6,371,935 B1 | 4/2002 | Macoviak et al. |
| 6,371,992 B1 | 4/2002 | Tanagho et al. |
| 6,379,379 B1 | 4/2002 | Wang |
| 6,385,476 B1 | 5/2002 | Osadchy et al. |
| 6,391,052 B2 | 5/2002 | Buirge et al. |
| 6,395,023 B1 | 5/2002 | Summers |
| 6,409,716 B1 | 6/2002 | Sahatjian et al. |
| 6,416,510 B1 | 7/2002 | Altman et al. |
| 6,432,119 B1 | 8/2002 | Saadat |
| 6,436,135 B1 | 8/2002 | Goldfarb |
| 6,443,941 B1 | 9/2002 | Slepian et al. |
| 6,443,949 B2 | 9/2002 | Altman |
| 6,447,504 B1 | 9/2002 | Ben-Haim et al. |
| 6,458,095 B1 | 10/2002 | Wirt et al. |
| 6,458,098 B1 | 10/2002 | Kanesaka |
| 6,464,862 B2 | 10/2002 | Bennett et al. |
| 6,465,001 B1 | 10/2002 | Hubbell et al. |
| 6,478,776 B1 | 11/2002 | Rosenman et al. |
| 6,482,231 B1 | 11/2002 | Abatangelo et al. |
| 6,485,481 B1 | 11/2002 | Pfeiffer |
| 6,494,862 B1 | 12/2002 | Ray et al. |
| 6,514,217 B1 | 2/2003 | Selmon et al. |
| 6,544,230 B1 | 4/2003 | Flaherty et al. |
| 6,548,081 B2 | 4/2003 | Sadozai et al. |
| 6,554,801 B1 | 4/2003 | Steward et al. |
| 6,599,267 B1 | 7/2003 | Ray et al. |
| 6,602,241 B2 | 8/2003 | Makower et al. |
| 6,616,869 B2 | 9/2003 | Mathiowitz et al. |
| 6,624,245 B2 | 9/2003 | Wallace et al. |
| 6,628,988 B2 | 9/2003 | Kramer et al. |
| 6,629,947 B1 | 10/2003 | Sahatjian et al. |
| 6,632,457 B1 | 10/2003 | Sawhney |
| 6,635,267 B1 | 10/2003 | Miyoshi et al. |
| 6,660,034 B1 | 12/2003 | Mandrusov et al. |
| 6,682,730 B2 | 1/2004 | Mickle et al. |
| 6,689,608 B1 | 2/2004 | Mikos et al. |
| 6,692,466 B1 | 2/2004 | Chow et al. |
| 6,702,744 B2 | 3/2004 | Mandrusov et al. |
| 6,706,034 B1 | 3/2004 | Bhat |
| 6,737,072 B1 | 5/2004 | Angele et al. |
| 6,748,258 B1 | 6/2004 | Mueller et al. |
| 6,749,617 B1 | 6/2004 | Palasis et al. |
| 6,759,431 B2 | 7/2004 | Hunter et al. |
| 6,761,887 B1 * | 7/2004 | Kavalkovich et al. ....... 424/93.7 |
| 6,777,231 B1 | 8/2004 | Katz et al. |
| 6,790,455 B2 | 9/2004 | Chu et al. |
| 6,824,791 B2 | 11/2004 | Mathiowitz et al. |
| 6,858,229 B1 | 2/2005 | Hubbell et al. |
| 6,916,488 B1 | 7/2005 | Meier et al. |
| 6,916,648 B2 | 7/2005 | Goddard et al. |
| 6,926,692 B2 | 8/2005 | Katoh et al. |
| 6,992,172 B1 | 1/2006 | Chang et al. |
| 7,008,411 B1 | 3/2006 | Mandrusov et al. |
| 7,035,092 B2 | 4/2006 | Hillman et al. |
| 7,112,587 B2 | 9/2006 | Timmer et al. |
| 7,129,210 B2 | 10/2006 | Lowinger et al. |
| 7,169,127 B2 | 1/2007 | Epstein et al. |
| 7,361,360 B2 | 4/2008 | Kitabwalla et al. |
| 7,374,774 B2 | 5/2008 | Bowlin et al. |
| 7,438,692 B2 | 10/2008 | Tsonton et al. |
| 7,615,373 B2 | 11/2009 | Simpson et al. |
| 7,815,590 B2 | 10/2010 | Cooper |
| 2001/0023349 A1 | 9/2001 | VanTassel et al. |
| 2001/0055615 A1 | 12/2001 | Wallace et al. |
| 2002/0013408 A1 | 1/2002 | Rhee et al. |
| 2002/0042473 A1 | 4/2002 | Trollsas et al. |
| 2002/0072706 A1 | 6/2002 | Hiblar et al. |
| 2002/0076441 A1 | 6/2002 | Shih et al. |
| 2002/0090725 A1 | 7/2002 | Simpson et al. |
| 2002/0102272 A1 | 8/2002 | Rosenthal et al. |
| 2002/0124855 A1 | 9/2002 | Chachques |

| | | | |
|---|---|---|---|
| 2002/0131974 | A1 | 9/2002 | Segal |
| 2002/0142458 | A1 | 10/2002 | Williams et al. |
| 2002/0146557 | A1 | 10/2002 | Claude et al. |
| 2002/0188170 | A1 | 12/2002 | Santamore et al. |
| 2003/0023202 | A1 | 1/2003 | Nielson |
| 2003/0040712 | A1 | 2/2003 | Ray et al. |
| 2003/0050597 | A1 | 3/2003 | Dodge et al. |
| 2003/0078671 | A1 | 4/2003 | Lesniak et al. |
| 2003/0105493 | A1 | 6/2003 | Salo |
| 2003/0175410 | A1 | 9/2003 | Campbell et al. |
| 2004/0002650 | A1 | 1/2004 | Mandrusov et al. |
| 2004/0181206 | A1 | 9/2004 | Chiu et al. |
| 2004/0185084 | A1 | 9/2004 | Rhee et al. |
| 2004/0208845 | A1 | 10/2004 | Michal et al. |
| 2004/0213756 | A1 | 10/2004 | Michal et al. |
| 2004/0229856 | A1 | 11/2004 | Chandrasekar et al. |
| 2005/0015048 | A1 | 1/2005 | Chiu et al. |
| 2005/0031874 | A1 | 2/2005 | Michal et al. |
| 2005/0042254 | A1 | 2/2005 | Freyman et al. |
| 2005/0064038 | A1 | 3/2005 | Dinh et al. |
| 2005/0070844 | A1 | 3/2005 | Chow et al. |
| 2005/0186240 | A1 | 8/2005 | Ringeisen et al. |
| 2005/0281883 | A1 | 12/2005 | Daniloff et al. |
| 2006/0149392 | A1 | 7/2006 | Hsieh et al. |
| 2006/0233850 | A1 | 10/2006 | Michal |
| 2007/0270948 | A1 | 11/2007 | Wuh |
| 2008/0025943 | A1 | 1/2008 | Michal et al. |

FOREIGN PATENT DOCUMENTS

| | | |
|---|---|---|
| EP | 0861632 | 9/1998 |
| EP | 0938871 | 9/1999 |
| EP | 1214077 | 1/2004 |
| GB | 2194144 | 3/1988 |
| JP | 61205446 | 9/1986 |
| JP | 2003062089 | 3/2003 |
| WO | WO-92/10142 | 6/1992 |
| WO | WO-98/30207 | 7/1998 |
| WO | WO-98/54301 | 12/1998 |
| WO | WO-9953943 | 10/1999 |
| WO | WO-00/16818 | 3/2000 |
| WO | W0-0054661 | 9/2000 |
| WO | WO-00/71196 | 11/2000 |
| WO | WO-01/24775 | 4/2001 |
| WO | WO-0124842 | 4/2001 |
| WO | WO-01/45548 | 6/2001 |
| WO | WO-01/49357 | 7/2001 |
| WO | WO-0200173 | 1/2002 |
| WO | WO-0204008 | 1/2002 |
| WO | WO-02/28450 | 4/2002 |
| WO | WO-02/40070 | 5/2002 |
| WO | WO-02/072166 | 9/2002 |
| WO | WO-02/087623 | 11/2002 |
| WO | WO-03/022909 | 3/2003 |
| WO | WO-03/027234 | 4/2003 |
| WO | WO-03026492 | 4/2003 |
| WO | WO-03/064637 | 8/2003 |
| WO | WO-2004/000915 | 12/2003 |
| WO | WO-2004/050013 | 6/2004 |
| WO | WO-2004058305 | 7/2004 |
| WO | WO-2004/066829 | 8/2004 |
| WO | WO-2004/091592 | 10/2004 |
| WO | WO-2005/061019 | 7/2005 |
| WO | WO-2005/067890 | 7/2005 |
| WO | WO-2006/039704 | 4/2006 |
| WO | WO-2006/113407 | 10/2006 |
| WO | WO-2007/048831 | 3/2007 |
| WO | WO-2007145909 | 12/2007 |

OTHER PUBLICATIONS

Abbott Cardiovascular Systems in, PCT Search Report dated Jan. 31, 2007, PCT Appln No. PCT/US2006/014021, 11 pages.

Abbott Cardiovascular Systems in, PCT Search Report dated Mar. 27, 2008, PCT Appln No. PCT/US2007/003614, 18 pages.

Advanced Cardiovascular Systems, Inc. et al., PCT International Preliminary Report on Patentability dated Jun. 19, 2007, PCT Appln. No. PCT/US2005/045627.

Advanced Cardiovascular Systems, Inc., PCT International Preliminary Report on Patentability dated Nov. 3, 2005, PCT Appln. No. PCT/US2004/011356, 6 pages.

Advanced Cardiovascular Systems, Inc., PCT International Search Report and Written Opinion mailed Oct. 13, 2006, PCT Appln No. PCT/US2005/045627.

Advanced Cardiovascular Systems, Inc., PCT International Search Report dated Feb. 9, 2004, PCT Appln. No. PCT/US03/30464, 5 pages.

Advanced Cardiovascular Systems, Inc., PCT International Search Report dated Jan. 28, 2004, PCT Appln. No. PCT/US03/18360, 7 pages.

Advanced Cardiovascular Systems, Inc., PCT Invitation to Pay Additional Fees mailed Nov. 4, 2003, PCT Appln No. PCT/US03/18360, 3 pages.

Advanced Cardiovascular Systems, Inc., PCT Search Report and Written Opinion dated Nov. 24, 2004, PCT Appln. No. PCT/US2004/011356, 12 pages.

Agocha, A., et al., "Hypoxia regulates basal and induced DNA synthesis and collagen type I production in human cardiac fibroblasts: effects of transforming growth factor-beta 1, thyroid hormone, angiotensin II and basic fibroblast growth factor", J. Mol. Cell. Cardiol., 29(8), Apr. 1997, pp. 2233-2244.

Allemann, E., et al., "Kinetics of Blood Component Adsorption on poly(D,L-lactic acid) Nanoparticles: Evidence of Complement C3 Component Involvement", J. Biomed. Mater. Res., 37(2), Abstract downloaded from the Internet at: http://www.ncbi.nlm.nih.gov/entrez./query.fcgi?cmd=Retrieve&db=PubMed, Nov. 1997, pp. 229-234.

Anderson, James M., et al., "Biodegradation and biocompatibility of PLA and PLGA microspheres", Advanced Drug Delivery Reviews 28, (1997), pp. 5-24.

Assmus, B., et al., "Transplantation of Progenitor Cells and Regeneration Enhancement in Acute Myocardial Infarction (TOPCARE-AMI)", Clinical Investigation and Reports, Oct. 8, 2002, pp. 3009-3017, Department of Molecular Cardiology and Department of hematology (H.M., D.H.) University of Frankfurt, Frankfurt, germany. Circulation Available at http://www.circulationha.org DOI: 10.116.

Baxter, "FloSeal Matrix Hemostatic Sealant", downloaded from the Internet on Nov. 14, 2002, from: http://www.fusionmed.com/docs/surgeon/default.asp, 2 pages.

Berger, et al., "Poly-L-cysteine", J. Am. Chem. Soc., 78(17), Sep. 5, 1956, pp. 4483-4488.

Bernatowicz, M., et al., "Preparation of Boc-[S-(3-nitro-2-pyridinesulfenyl)]-cysteine and its use for Unsymmetrical Disulfide Bond Formation", Int. J. Peptide Protein Res. 28(2), Aug. 1996, pp. 107-112.

Boland, E. D., "Electrospinning Collagen and Elastin: Preliminary Vascular Tissue Engineering", Frontiers in Bioscience, vol. 9, May 1, 2004, pp. 1422-1432.

Brust, G., "Polyimides", downloaded from the Internet at: http://www.pslc.ws/macrog/imide.htm, 2005, 4 pages.

Buschmann, I., et al., "Arteriogenesis versus angiogenesis: Two mechanisms of vessel growth", News Physiol. Sci., vol. 14, Jun. 1999, 121-125.

Canderm Pharma, "Technical Dossier: Artecoll", downloaded from the Internet on Oct. 22, 2002 from: http://www.canderm.com/artecoll/tech.html, 3 pages.

Capan, Y., et al., "Preparation and Characterization of Poly(D,L-lactide-co-glycolide) Microspheres for Controlled Release of Human Growth Hormone", AAPS PharmSciTech.; 4(2): article 28, Downloaded from the Internet at: http://www.aapspharmscitech.org/view.asp?art=pt040228&pdf=yes, (2003), 12 pages.

Caplan, Michael J., et al., "Dependence on pH of polarized sorting of secreted proteins", Dept. of Cell Biology and Dept. of Pathology, Yale University School of Medicine, Nature, vol. 329, Oct. 15, 1987, p. 630.

Carpino, L., et al., "Tris(2-aminoethyl)amine as a Substitute for 4-(Aminomethyl)piperidine in the FMOC/Polyamine Approach to Rapid Peptide Synthesis", J. Org. Chem., 55(5), Mar. 1990, pp. 1673-1675.

Chandy, et al., "The development of porous alginate/elastin/PEG composite matrix for cardiovascular engineering", Journal of Biomaterials Applications, vol. 17, Apr. 2003, pp. 287-301.

Choi, Young Seon, et al., "Study on gelatin-containing artificial skin: I. Preparation and characteristics of novel gelatin-alginate sponge", Biomaterials, vol. 20, 1999, 409-417.

Corbett, S., et al., "Covalent Cross-linking of Fibronectin to Fibrin is Required for Maximal Cell Adhesion to a Fibronectin-Fibrin Matrix", The Journal of Biological Chemistry, 272(40), Oct. 3, 1997, pp. 24999-25005.

Creemers, E., et al., "Matrix Metalloproteinase Inhibition After Myocardial Infarction: A New Approach to Prevent Heart Failure?", Circ. Res., vol. 89, 2001, pp. 201-210.

Crivello, et al., "Synthesis and Photoinitiated Cationic Polymerization of Monomers with the Silsesquioxane Core", J Polym Science: Part A: Polymer Chemistry 35, 1997, pp. 407-425.

Davis, M. E., et al., "Injectable Self-Assembling Peptide Nanofibers Create Intramyocardial Microenvironments for Endothelial Cells", Circulation, 111, Feb. 2005, pp. 442-450.

De Rosa, et al., "Biodegradable Microparticles for the Controlled Delivery of Oligonucleotides", International Journal of Pharmaceutics, 242, Aug. 21, 2002, pp. 225-228.

Desai, M., et al., "Polymer bound EDC (P-EDC): A convenient reagent for formation of an amide bond", Tetrahedron Letters, 34(48), Abstract downloaded from the Internet at: http://www.sciencedirect.com, 1 page, Nov. 1993, pp. 7685-7688.

Dinbergs, et al., "Cellular response to transforming growth factor-$\beta 1$ and basic fibroblast growth factor depends on release kinetics and extracellular matrix interactions", The Journal of Biological Chemistry, vol. 271, No. 47, Nov. 1996, pp. 29822-29829.

Dong, Zhanfeng, et al., "Alginate/gelatin blend films and their properties for drug controlled release", Journal of Membrane Science, vol. 280, 2006, pp. 37-44.

Edelman, "Controlled and modulated release of basic fibroblast growth factor", Biomaterials, vol. 12, Sep. 1999, pp. 619-626.

Etzion, S., et al., "Influence of Embryonic Cardiomyocyte Transplantation on the Progression of Heart Failure in a Rat Model of Extensive Myocardial Infarction", J. Mol. Cell Cardiol., 33, May 2001, pp. 1321-1330.

Ferrara, N., "Role of Vascular Endothelial Growth Factor in the Regulation of Angiogenesis", Kidney International, 56(3), Abstract downloaded from the Internet at: http://www.nature.com/ki/journal/v56/n3/abs/4490967a.html, 1 page, 1999, pp. 794-814.

Fuchs, S., et al., "Catheter-Based Autologous Bone Marrow Myocardial Injection in No-Option Patients with Advanced Coronary Artery Disease", J. Am. Coll. Cardiol., 41(10), 2003, pp. 1721-1724.

Fukumoto, S., et al., "Protein Kinase C $\delta$; Inhibits the Proliferation of Vascular Smooth Muscle Cells by Suppressing G1 Cyclin Expression", The Journal of Biological Chemistry, 272(21), May 1997, pp. 13816-13822.

Giordano, F., et al., "Angiogenesis: The Role of the Microenvironment in Flipping the Switch", Current Opinion in Genetics and Development, 11, 2001, pp. 35-40.

Gossler, et al., "Transgenesis by means of blastocyst-derived embryonic stem cell lines", Proc. Natl. Acad. Sci. USA, 83, Dec. 1986, pp. 9065-9069.

Grafe, T. H., "Nanofiber Webs from Electrospinning", Presented at the Nonwovens in Filtration—Fifth International Conference, Stuttgart, Germany, Mar. 2003, pp. 1-5.

Gref, R., et al., "Biodegradable Long-Circulating Polymeric Nanospheres", Science, 263(5153), Abstract downloaded from the Internet at: http://www.sciencemag.org/cgi/content/abstract/263/5153/1600, 1 page, Mar. 1994, pp. 1600-1603.

Grund, F., et al., "Microembolization in Pigs: Effects on Coronary Blood Flow and Myocardial Ischemic Tolerance", Am. J. Physiol., 277 (Heart Circ. Physiol. 46), 1999, pp. H533-H542.

Gupta, et al., "Changes in Passive Mechanical Stiffness of Myocardial Tissue with Aneurysm Formation", Circulation, 89(5), May 1994, pp. 2315-2326.

Hanawa, T., et al., "New oral dosage form for elderly patients: preparation and characterization of silk fibroin gel", Chemical and Pharmaceutical Bulletin, Pharmaceutical Society of Japan, Tokyo, vol. 43, No. 2, Jan. 1995, pp. 284-288.

Hashimoto, T., et al., "Development of Alginate Wound Dressings Linked with Hybrid Peptides Derived from Laminin and Elastin", Biomaterials, 25, 2004, pp. 1407-1414.

Haugland, et al., "Dialkylcarbocyanine and Dialkylaminostryryl Probes", Handbook of Fluorescent Probes and Research Products, Molecular Probes, Inc., 2002, pp. 530-534.

Haugland, et al., "Membrane-permeant reactive tracers", Handbook of Fluorescent Probes and Research Products, Molecular Probes, Inc., 2002, pp. 458-553.

Heeschen, C., et al., "Nicotine Stimulates Tumor Angiogenesis", American College of Cardiology, 37(2) Supplement A, Abstract downloaded from the Internet at: http://24.132.160.238/ciw-01acc/abstract_search_author.cfm?SearchName=Heeschen, 1 page, Feb. 2001, pp. 1A-648A.

Helisch, A., et al., "Angiogenesis and arteriogenesis—not yet for prescription", NEUE Diagnostische Und Therap. Verfahren, Z Kardiol 89, 2000, pp. 239-244.

Hendel, R. C., et al., "Effect of Intracoronary Recombinant Human Vascular Endothelial Growth Factor on Myocardial Perfusion: Evidence for a Dose-Dependent Effect", Circulation, 101, 2000, pp. 118-121.

Henry, R. R., et al., "Insulin Action and Glucose Metabolism in Nondiabetic Control and NIDDM Subjects: Comparison Using Human Skeletal Muscle Cell Cultures", Diabetes, 44(8), Abstract downloaded from the Internet at: http://diabetes.diabetesjournals.org/cgi/content/abstract/44/8/936, 1 page, 1995, pp. 936-946.

Hoffman, "Hydrogels for Biomedical Applications", Advanced Drug Delivery Reviews, vol. 43, 2002, pp. 3-12.

Holland, N. B., et al., "Biomimetic Engineering of Non-Adhesive glycocalyx-like Surfaces Using Oligosaccharide Surfactant Polymers", Nature, 392, Abstract downloaded from the Internet at: http://www.nature.com, 1 page, Apr. 1998, pp. 799-801.

Horan, R.L., et al., "In Vitro Degradation of Silk Fibroin", Biomaterials, vol. 26, 2004, pp. 3385-3393.

Hovinen, J., et al., "Synthesis of 3'-functionalized oligonucleotides on a single solid support", Tetrahedron Letters, 34(50), Abstract downloaded from the Internet at: http://www.sciencedirect.com, 1 page, Dec. 1993, pp. 8169-8172.

Huang, K., et al., "Synthesis and Characterization of Self-Assembling Block Copolymers Containing Bioadhesive End Groups", Biomacromolecules, 3(2), 2002, pp. 397-406.

Hutcheson, K., et al., "Comparison of Benefits on Myocardial Performance of Cellular Cardiomyoplasty with Skeletal Myoblasts and Fibroblasts", Cell Transplantation, 9(3), 2000, pp. 359-368.

Huynh, T. V., et al., "Constructing and Screening cDNA Libraries in $\lambda$gt10 and $\lambda$gt11", Chapter 2 in DNA Cloning, vol. 1: A Practical Approach, ed. by D.M. Glover, 1985, pp. 49-78.

Indik, Z., et al., "Production of Recombinant Human Tropoelastin: Characterization and Demonstration of Immunologic and Chemotactic Activity", Arch. Biochem. Biophys., 280(1), Abstract downloaded from the Internet at: http://www.ncbi.nlm.nih.gov/entrez/query.fcgi?cmd=Retrieve&db=PubMed, 1 page, Jul. 1990, pp. 80-86.

Iskandrian, A. S., et al., "Nuclear Cardiac Imaging: Principles and Applications", second edition, F.A. Davis Co., Philadelphia, cover page, title page and TOC, 1996, 5 pages.

Isner, J. M., "Vascular Endothelial Growth Factor: Gene Therapy and Therapeutic Angiogenesis", Am. J. Cardiol., 82(10A), (Nov 19, 1998), pp. 63S-64S.

Ito, Wulf D., et al., "Monocyte chemotactic protein-1 increases collateral and peripheral conductance after femoral artery occlusion", Max-Planck-Institute for Physiological and Clinical Research, Bad Nauheim, Germany, Feb. 21, 1997, pp. 829-837.

Johnson, et al., "The stabilization and encapsulation of human growth hormone into biodegradable microspheres", Pharmaceutical Research, vol. 14, No. 6, 1997, pp. 730-735.

Jonasson, P., et al., "Denatured states of human carbonic anhydrase II: an NMR study of hydrogen/deuterium exchange at tryptophan-indole-Hn sites", FEBS Letters, 445, 1999, pp. 361-365.

Kalltorp, Mia, et al., "Inflammatory cell recruitment, distribution, and chemiluminescence response at IgG precoated- and thiol functionalized gold surfaces", Swedish Biomaterials Consortium, Swedish Foundation for Strategic Research, Apr. 9, 1999, pp. 251-259.
Kaplan, D.L., et al., "Spiderless Spider Webs", Nature Biotechnology, vol. 20, 2002, pp. 239-240.
Kawai, et al., "Accelerated tissue regeneration through incorporation of basic fibroblast growth factor-impregnated gelatin microspheres into artificial dermis", Biomaterials, 21(5), Mar. 2002, pp. 489-499.
Kawasuji, M., et al., "Therapeutic Angiogenesis with Intramyocardial Administration of Basic Fibroblast Growth Factor", Ann Thorac Surg, 69, Abstract downloaded from the Internet at: http://ats.ctsnetjournals.org/cgi/content/abstract/69/4/1155, 2 pages, 2000, pp. 1155-1161.
Kelley, et al., "Restraining Infarct Expansion Preserves Left Ventricular Geometry and Function After Acute Anteroapical Infarction", Circulation, 99, 1999, pp. 135-142.
Kelly, E. B., "Advances in Mammalian and Stem Cell Cloning", Genetic Engineering News, vol. 23, No. 7, Apr. 1, 2003, pp. 17-18 & 68.
Khademhosseini, et al., "Microscale Technologies for Tissue Engineering and Biology", PNAS, vol. 103, No. 8, Feb. 21, 2006, pp. 2480-2487.
Kim, D., et al., "Glow Discharge Plasma Deposition (GDPD) Technique for the Local Controlled Delivery of Hirudin from Biomaterials", Pharmaceutical Research, 15(5), 1998, pp. 783-786.
Kim, Ung-Jin, et al., "Structure and Properties of Silk Hydrogels", Biomacromolecules, vol. 5(3), 2004, pp. 786-792.
Kinart, et al., "Electrochemical Studies of 2-hydroxy-3-(3,4-dimethy1-9-oxo-9H-thioxanthen-2-yloxy)N,N,N-trimethyl-1-propanium chloride", J. Electroanal. Chem, 294, 1990, pp. 293-297.
Kipshidze, Nicholas, et al., "Therapeutic angiogenesis for critical limb ischemia to limit or avoid amputation", University of Wisconsin Medical School, The Journal of Invasive Cardiology, vol. 11, No. 1, Jan. 1999, pp. 25-28.
Klein, S., et al., "Fibroblast Growth Factors as Angiogenesis Factors: New Insights Into Their Mechanism of Action", Regulation of Angiogenesis, I.D. Goldberg and E.M. Rosen (eds.), 79, 1997, pp. 159-192.
Klugherz, Bruce D., et al., "Gene delivery from a DNA controlled-release stent in porcine coronary arteries", Nature Biotechnology, vol. 18, Nov. 2000, pp. 1181-1184.
Kohilas, K., et al., "Effect of prosthetic titanium wear debris on mitogen-induced monocyte and lymphoid activation", John Hopkins University, Dept. of Orthopaedic Surgery, Apr. 1999, pp. 95-103.
Kweon, H. Y., et al., "Preparation of semi-interpenetrating polymer networks composed of silk fibroin and poly(ethyleneglycol) macromer", Journal of Applied Polymer Science, John Wiley and Sons Inc., New York, NY, vol. 80, Jan. 2001, pp. 1848-1853.
Kwok, C., et al., "Design of Infection-Resistant Antibiotic-Releasing Polymers: I. Fabrication and Formulation", Journal of Controlled Release, 62, 1999, pp. 289-299.
Laboratory of Liposome Research, "Liposomes: General Properties", downloaded from the Internet on Feb. 9, 2006 at: http://www.unizh.ch/onkwww/lipos.htm, 5 pages.
Laham, R. J., "Intrapericardial Delivery of Fibroblast Growth Factor-2 Induces Neovascularization in a Porcine Model of Chronic Myocardial Ischemia", J. Pharmacol Exper Therap, 292(2), 2000, pp. 795-802.
Leibovich, S. J., et al., "Macrophage-Induced Angiogenesis is Mediated by Tumour Necrosis Factor-α", Nature, vol. 329, Oct. 15, 1987, pp. 630-632.
Leor, J., et al., "Bioengineered Cardiac Grafts-A New Approach to Repair the Infarcted Myocardium?", Circulation, 102[suppl III], 2000, pp. III-56-III-61.
Leor, J., et al., "Gene Transfer and Cell Transplant: An Experimental Approach to Repair a 'Broken Heart'", Cardiovascular Research, 35, 1997, pp. 431-441.
Leroux, J. C., et al., "An Investigation on the Role of Plasma and Serum Opsonins on the Internalization of Biodegradable poly(D,L-lactic acid) Nanoparticles by Human Monocytes", Life Sci., 57(7), Abstract downloaded from the Internet at: http://www.ncbi.nlm.nih.gov/entrez/query.fcgi?cmd=Retrieve&db=pubmed, 1 page, 1995, pp. 695-703.
Lewin, B., "Repressor is Controlled by a Small Molecule Inducer", Genes VII, Oxford University Press, 7th ed., 2000, pp. 277-280.
Li, et al., "Cell Therapy to Repair Broken Hearts", Can. J. Cardiol., vol. 14, No. 5, May 1998, pp. 735-744.
Li, W. W., et al., "Lessons to be Learned from Clinical Trials of Angiogenesis Modulators in Ischemic Diseases", Angiogenesis in Health & Disease: Basic Mechanisms and Clinical Applications, Rubanyi, G. (ed), Marcel Dekker, Inc. New York, 2000, Chapter 33.
Li, J., et al., "PR39, A Peptide Regulator of Angiogenesis", Nature Medicine, 6(1), Jan. 2000, pp. 49-55.
Li., Y. Y., et al., "Differential Expression of Tissue Inhibitors of Metalloproteinases in the Failing Human Heart", Circulation, 98(17), 1998, pp. 1728-1734.
Lindsey, M., et al., "Selective Matrix Metalloproteinase Inhibition Reduces Left Ventricular Remodeling but does not Inhibit Angiogenesis after Myocardial Infarction", Circulation, 105(6), 2002, pp. 753-758.
Long, D. M., et al., "Self-Cleaving Catalytic RNA", FASEB Journal, 7, 1993, pp. 25-30.
Lopez, J. J., et al., "Angiogenic potential of perivascular delivered aFGF in a porcine model of chronic myocardial ischemia", The American Physiological Society, 0363-6135/98, 1998, H930-H936.
Lopez, J. J., et al., "VEGF Administration in Chronic Myocardial Ischemia in Pigs", Cardiovasc. Res., 40(2), Abstract downloaded from the Internet at: http://www.ncbi.nlm.nih.gov/entrez/query.fcgi?cmd=Retrieve&db=pubmed, 1 page, 1998, pp. 272-281.
Lu, L., et al., "Biodegradable Polymer Scaffolds for Cartilage Tissue Engineering", Clinical Orthopaedics and Related Research, Carl T. Brighton (ed.). No. 391S, 2001, pp. S251-S270.
Luo, Y., et al., "Cross-linked Hyaluronic Acid Hydrogel Films: New Biomaterials for Drug Delivery", Journal of Controlled Release, 69, 2000, pp. 169-184.
Lutolf, M., et al., "Synthesis and Physicochemical Characterization of End-Linked Poly(ethylene glycol)-co-peptide Hydrogels Formed by Michael-Type Addition", Biomacromolecules, vol. 4, 2003, pp. 713-722.
Lyman, M. D., et al., "Characterization of the Formation of Interfacially Photopolymerized Thin Hydrogels in Contact with Arterial Tissue", Biomaterials, 17(3), 1996, pp. 359-364.
Mansour, S., et al., "Disruption of the proto-oncogene int-2 in mouse embryo-derived stem cells: a general strategy for targeting mutations to non-selectable genes", Nature, 336, 1988, pp. 348-352.
Martin, S. L., et al., "Total Synthesis and Expression in *Escherichia coli* of a Gene Encoding Human Tropoelastin", Gene, 1995, Abstract, 1 page.
McDevitt, T., et al., "In vitro Generation of Differentiated Cardiac Myofibers on Micropatterned Laminin Surfaces", J. Biomed Mater Res., 60, 2002, pp. 472-479.
Meinel, L., et al., "The Inflammatory Responses to Silk Films In Vitro and In Vivo", Biomaterials, vol. 26, 2005, pp. 147-155.
Narmoneva, D. A., et al., "Self-assembling short oligopeptides and the promotion of angiogenesis", Biomaterials, 26, 2005, pp. 4837-4846.
Nazarov, R., et al., "Porous 3-D Scaffolds from Regenerated Silk Fibroin", Biomacromolecules, vol. 5(3), 2004, pp. 718-726.
Nguyen, K. T., et al., "Photopolymerizable Hydrogels for Tissue Engineering Applications", Biomaterials, 23, 2002, pp. 4307-4314.
Nikolic, S. D., et al., "New Angiogenic Implant Therapy Improves Function of the Ischemic Left Venticle", Supplement to Circulation; Abstracts From Scientific Sessions 2000, 102(18), Oct. 2000, pp. 11-689, Abstract 3331.
Nikolic, Serjan D., et al., "Novel means to improve coronary blood flow", Clinical Science, Abstracts from Scientific Sessions, 2000, pp. II-689.
Nitinol Technical Information, "NiTi Smart Sheets", downloaded from the Internet on Dec. 10, 2002 at: http://www.sma-inc.com/information.html, 1 page.

Nose, et al., "A novel cadherin cell adhesion molecule: its expression patterns associated with implantation and organogenesis of mouse embryos", Journal of Cell Biology, vol. 103 (No. 6, Pt. 2), The Rockefeller University Press, Dec. 1986, pp. 2649-2658.

Ohyanagi, H., et al., "Kinetic Studies of Oxygen and Carbon Dioxide Transport into or from Perfluorochemical Particles", Proc. ISAO, vol. 1 (Artificial Organs vol. 2 (Suppl.)), 1977, pp. 90-92.

Ozbas, B., et al., "Salt-Triggered Peptide Folding and Consequent Self-Assembly into Hydrogels with Tunable Modulus", Macromolecules, 37(19), 2004, pp. 7331-7337.

Ozbas-Turan, S., "Controlled Release of Interleukin-2 from Chitosan Microspheres", Journal of Pharmaceutical Sciences, 91(5), May 2002, pp. 1245-1251.

Palmiter, R., et al., "Germ-Line Transformation of Mice", Ann. Rev. Genet., 20, 1986, pp. 465-499.

Patrick, C. R., "Mixing and Solution Properties of Organofluorine Compounds", Preparation, Properties and Industrial Applications of Organofluorine Compounds, Chapter 10, R.E. Banks (ed.), 1st edition, Ellis-Horwood Ltd., Chichester:England, 1982, pp. 323-342.

Peattie, R. A., et al., "Stimulation of In Vivo Angiogenesis by Cytokine-Loaded Hyaluronic Acid Hydrogel Implants", Biomaterials, 25(14), Abstract downloaded from: www.sciencedirect.com, Jun. 2004, 2 pages.

Penta, K., et al., "Del1 Induces Integrin Signaling and Angiogenesis by Ligation of $\alpha V\beta 3$", J. Biolog. Chem., 274(16), Apr. 1999, pp. 11101-11109.

Perin, E. C., et al., "Transendocardial, Autologous Bone Marrow Cell Transplantation for Severe, Chronic, Ischemic Heart Failure", Circulation, 2003, 1 page.

Pouzet, B., et al., "Is Skeletal Myoblast Transplantation Clinically Relevant in the Era of Angiotensin-Converting Enzyme Inhibitors?", Circulation, 104 [suppl I], Sep. 2001, pp. 1-223-1-228.

Prather, et al., "Nuclear Transplantation in Early Pig Embryos", Biol. Reprod., 41, 1989, pp. 414-418.

Prosci Incorporated, "ILPIP (CT) Peptide", 1 page.

Quellec, P., et al., "Protein Encapsulation Within Polyethylene Glycol-coated Nanospheres. I. Physicochemical Characterization", J. Biomed. Mater. Res., 42(1), 1998, Abstract, 1 page.

Ramirez-Solis, R., et al., "Gene Targeting in Embryonic Stem Cells", Methods in Enzymology, 225, 1993, pp. 855-878.

Rowley, et al., "Alginate Hydrogels as Synthetic Extracelllular Matrix Materials", Biomaterials, 20(1), 1999, pp. 45-53.

Sawhney, A. S., et al., "Bioerodible Hydrogels Based on Photopolymerized Poly(ethylene glycol)-co-poly(a-hydroxy acid) Diacrylate Macromers", Macromolecules, 26(4), 1993, pp. 581-587.

Sbaa-Ketata, E., et al., "Hyaluronan-Derived Oligosaccharides Enhance SDF-1- Dependent Chemotactic Effect on Peripheral Blood Hematopoietic CD34+ Cells", Stem Cells, 20(6), Letter to the Editor downloaded from the Internet at: http://stemcells.alphamedpress.org/cgi/content/full/20/6/585, 2002, pp. 585-587.

Segura, T., et al., "Crosslinked Hyaluronic Acid Hydrogels: A Strategy to Functionalize and Pattern", Biomaterials, vol. 26(4), Feb. 2005, pp. 359-371.

Segura, T., et al., "DNA delivery from hyaluronic acid-collagen hydrogels via a substrate-mediated approach", Biomaterials, vol. 26, 2005, pp. 1575-1584.

Segura, T., et al., "Substrate-Mediated DNA Delivery: Role of the Cationic Polymer Structure and Extent of Modification", Journal of Controlled Release, 93, 2003, pp. 69-84.

Segura, T., et al., "Surface-Tethered DNA Complexes for Enhanced Gene Delivery", Bioconjugate Chem, 13(3), 2002, pp. 621-629.

Shibasaki, F., et al., "Suppression of Signalling Through Transcription Factor NF-AT by Interactions Between Calcineurin and Bcl-2", Nature, 386(6626), Abstract downloaded from the Internet at: http://www.ncbi.nlm.nih.gov/entrez/query.fcgi?CMD=Text&DB=pubmed, 1 page, 1997.

Shin, H., et al., "Attachment, Proliferation, and Migration of Marrow Stromal Osteoblasts Cultured on Biomimetic Hydrogels Modified with an Osteopontin-Derived Peptide", Biomaterials, 25, 2004, pp. 895-906.

Shin, H., et al., "In vivo bone and soft tissue response to injectable, biodegradable oligo(poly(ethylene glycol) fumarate) hydrogels", Biomaterials 24, Elsevier Science Ltd., 2003, pp. 3201-3211.

Shu, Z., et al., "Disulfide-crosslinked hyaluronan-gelatin hydrogel films: a covalent mimic of the extracellular matrix for in vitro cell growth", Biomaterials, vol. 24(21), Sep. 2003, pp. 3825-3834.

Shu, Zheng, et al., "In situ crosslinkable hyaluronan hydrogels for tissue engineering", Biomaterials, vol. 25, 2004, pp. 1339-1348.

Simons, M., et al., "Clinical trials in coronary angiogenesis: Issues, problems, consensus, an expert panel summary", Angiogenesis Research Center, American Heart Association, Inc., Sep. 12, 2000, pp. 1-14.

Spenlehauer, G., et al., "In vitro and in vivo degradation of poly(D,L lactide/glycolide) type microspheres made by solvent evaporation method", Biomaterials, vol. 10, Oct. 1989, pp. 557-563.

Spinale, F. G., "Matrix Metalloproteinases—Regulation and Dysregulation in the Failing Heart", Circ. Res., 90, 2002, pp. 520-530.

Springer, M., et al., "Angiogenesis Monitored by Perfusion with a Space-Filling Microbead Suspension", Mol. Ther., 1(1), Abstract downloaded from the Internet at: http://www.ncbi.nlm.nih.gov/entrez/query.fcgi?cmd=Retrieve&db=PubMed, 1 page, 2000, pp. 82-87.

Storm, G., et al., "Surface Modification of Nanoparticles to Oppose Uptake by the Mononuclear Phagocyte System", Advanced Drug Delivery Reviews, 17(1), Abstract downloaded from the Internet at: http://www.sciencedirect.com, 1 page, Oct. 1995, pp. 31-48.

Strauer, B., et al., "Repair of Infarcted Myocardium by Autologous Intracoronary Mononuclear Bone Marrow Cell Transplantation in Humans", Circulation, 106, 2002, pp. 1913-1918.

Tybulewicz, V., et al., "Neonatal lethality and lymphopenia in mice with a homozygous disruption of the c-abl proto-oncogene", Cell, 65(7), Abstract downloaded from the Internet at: http://www.sciencedirect.com, 2 pages, Jun. 1991, pp. 1153-1163.

Unger, E. F., et al., "Effects of a Single Intracoronary Injection of Basic Fibroblast Growth Factor in Stable angina Pectoris", Am. J. Cardiol., 85(12), Abstract downloaded from the Internet at: http://www.sciencedirect.com, 2 pages, Jun. 2000, pp. 1414-1419.

Van Der Giessen, Willem J., et al., "Marked inflammatory sequelae to implantation of biodegradable and nonbiodegradable polymers in porcine coronary arteries", Dept. Of Cardiology, Erasmus University Rotterdam, Circulation, vol. 94, No. 7, Oct. 1, 1996, pp. 1690-1697.

Van Luyn, M. J., et al., "Cardiac Tissue Engineering: Characteristics of in Unison Contracting Two- and Three-Dimensional Neonatal Rat Ventricle Cell (Co)-Cultures", Biomaterials, 23, 2002, pp. 4793-4801.

Vercruysse, K. P., et al., "Synthesis and in Vitro Degradation of New Polyvalent Hydrazide Cross-Linked Hydrogels of Hyaluronic Acid", Bioconjugate Chem, 8(5), Abstract downloaded from the Internet at: http://pubs.acs.org/cgi-bin/abstract.cgi/bcches/1997/8/i05/abs/bc9701095.html, 1 page, 1997, pp. 686-694.

Visscher, G.E., et al., "Tissue response to biodegradable injectable microcapsules", Journal of Biomaterials Applications, vol. 2, Jul. 1987, pp. 118-119.

Vlodavsky, I., et al., "Extracellular Matrix-resident Basic Fibroblast Growth Factor: Implication for the Control of Angiogenesis", J. Cell Biochem, 45(2), Abstract downloaded from the Internet at: http://www.ncbi.nlm.nih.gov/entrez/query.fcgi?cmd=Retrieve&db=PubMed, 1 page, Feb. 1991, pp. 167-176.

Wang, M., et al., "Mechanical Properties of Electrospun Silk Fibers", Macromolecules, vol. 37(18), 2004, pp. 6856-6864.

Wasielewski, "Ischamische Erkrankungen, Gefassneubildung anregen", Deutsche Apotheker Zeitung, vol. 140, No. 3, Stuttgart (DE), Jan. 20, 2000, pp. 232-233.

Wilensky, R., et al., "Direct intraarterial wall injection of microparticles via a catheter: a potential durg delivery strategy following angioplasty", American Heart Journal, 122, 1991, pp. 1136.

Witzenbichler, B., et al., "Vascular Endothelial Growth Factor-C (VEGF-C/VEGF-2) Promotes Angiogenesis in the Setting of Tissue Ischemia", Am Pathol., 153(2), Aug. 1998, pp. 381-394.

Yager, P., et al., "Silk Protein Project", www.faculty.washington.edu/yagerp/silkprojecthome.html, Aug. 23, 1997 18 pages.

Yamamoto, N., et al., "Histologic evidence that basic fibroblast growth factor enhances the angiogenic effects of transmyocardial laser revascularization", Basic Research in Cardiology, vol. 95, No. 1, Feb. 1, 2000, pp. 55-63.

Yeo, L.Y., et al., "AC Electrospray Biomaterials Synthesis", Biomaterials, 2005, 7 pages.

Zervas, L., et al., "On Cysteine and Cystine Peptides. II. S-Acylcysteines in Peptide Synthesis", J. Am. Chem. Soc., 85(9), May 1963, pp. 1337-1341.

Zheng, W., et al., "Mechanisms of coronary angiogenesis in response to stretch: role of VEGF and TGF-beta", Am J Physiol Heart Circ Physiol., 280(2), Feb. 2001, pp. H909-H917.

Zimmermann, W., et al., "Engineered Heart Tissue for Regeneration of Diseased Hearts", Biomaterials, 25, 2004, pp. 1639-1647.

Abbott Cardiovascular Systems, International Preliminary Report on Patentability dated Jul. 30, 2009 for PCT/US2008/051505.

Abbott Cardiovascular Systems, Final office action dated Nov. 12, 2009 for U.S. Appl. No. 12/013,286.

Abbott Cardiovascular Systems, Final office action dated Nov. 25, 2009 for U.S. Appl. No. 11/566,643.

Abbott Cardiovascular Systems, Non final office action dated Dec. 9, 2009 for U.S. Appl. No. 10/781,984.

Abbott Cardiovascular Systems, Examination Report dated Jan. 13, 2010 for EP Application No. 07795729.8.

Abbott Cardiovascular Systems, Non final office action dated Feb. 5, 2010 for U.S. Appl. No. 11/447,340.

Abbott Cardiovascular Systems, Final Office Action dated Jan. 29, 2010 for U.S. Appl. No. 10/792,960.

Abbott Cardiovascular Systems, Examination Report dated Jan. 15, 2010 for EP 08727952.7.

Abbott Cardiovascular Systems, Examination Report dated Feb. 5, 2010 for EP 07810637.4.

Zheng, Shu , et al., "In situ crosslinkable hyaluronan hydrogels for tissue engineering", Biomaterials, Elsevier Science Publishers, vol. 25, No. 7-8, (2004), 1339-1348.

Abbott Cardiovascular Systems Inc, PCT International Search Report and Written Opinion mailed Feb. 10, 2009 for PCT Application No. PCT/US2007/023419, 17 pages.

Friedman, Paul M., et al., "Safety Data of Injectable Nonanimal Stabilized Hyaluronic Acid Gel for Soft Tissue Augmentation," Dermatologic Surgery, 2002, vol. 28, pp. 491-494.

Abbott Cardiovascular Systems, Non final office action dated Apr. 14, 2010 for U.S. Appl. No. 12/016,180.

Abbott Cardiovascular Systems, Final office action dated Apr. 22, 2010 for U.S. Appl. No. 10/414,602.

Abbott Cardiovascular Systems, Non final office action dated Apr. 29, 2010 for U.S. Appl. No. 10/792,960.

Hao, X , et al., "Angiogenic effects of sequential release of VEGF-A165 and PDGF-BB with alginate hydrogels after myocardial infarction", Cardiovascular Research, 75, (2007), 178-185.

Ritter, A. B., et al., "Elastic modulus, distensibility, and compliance (capacitance)", Biomedical Engineering Principles, Chapter 4, (2005), 187-191.

Abbott Cardiovascular Systems, Non Final Office Action dated May 12, 2009 for U.S. Appl. No. 11/496,824.

Abbott Cardiovascular Systems, Non Final Office Action dated Mar. 13, 2009 for U.S. Appl. No. 10/414,602.

Abbott Cardiovascular Systems, International search report and written opinion dated Jun. 18, 2009 for PCT/US2008/051505.

Abbott Cardiovascular Systems, Non final office action dated Jul. 9, 2009 for U.S. Appl. No. 11/561,328.

Abbott Cardiovascular Systems, Non Final Office Action dated Apr. 29, 2009 for U.S. Appl. No. 12/013,286.

Abbott Cardiovascular Systems, Non Final Office Action dated Apr. 13, 2009 for U.S. Appl. No. 11/566,643.

Abbott Cardiovascular Systems, Non Final Office Action dated Mar. 30, 2009 for U.S. Appl. No. 10/792,960.

Abbott Cardiovascular Systems, Non Final Office Action dated Apr. 6, 2009 for U.S. Appl. No. 11/447,340.

Elbert, D. L., et al., "Protein delivery from materials formed by self-selective conjugate addition reactions", Journal of Controlled Release, 76, (2001), 11-25.

Staatz, WD , et al., "Identification of a tetrapeptide recognition sequence for the alpha 2 beta 1 integrin in collagen", Journal of Biological Chemistry, 1991, 266(12), pp. 7363-7367.

Abbott Cardiovascular Systems, Non-Final Office Action dated Jun. 4, 2010 for U.S. Appl. No. 10/781,984.

Abbott Cardiovascular Systems, Final Office Action dated Jun. 11, 2010 for U.S. Appl. No. 11/561,328.

Abbott Cardiovascular Systems, Non final office action dated Aug. 13, 2010 for U.S. Appl. No. 11/447,340.

Abbott Cardiovascular Systems, Japanese Office Action dated Dec. 8, 2010 for Japanese Patent App No. 2006-509975, 6 pages.

Bull, S., et al., "Self-Assembled Peptide Amphiphile Nanofibers Conjugated to MRI Contrast Agents", Nano Letters, vol. 5, No. 1, (Jan. 2005), 4 pages.

Csonka, E., et al., "Interspecific Interaction of Aortic Endothelial and Smooth Muscle Cells", Acta Morphologica Hungarica, vol. 35, No. 1-2, (1987), 31-35.

Griese, D. P., et al., "Vascular gene delivery of anticoagulants by transplantation of retrovirally-transduced endothelial progenitor cells", Cardiovascular Research, vol. 58, (2003), 469-477.

Hartgerink, J. D., et al., "Peptide-amphiphile nanofibers: A versatile scaffold for the preparation of self-assembling materials", PNAS, vol. 99, No. 8, (Apr. 16, 2002), 5133-5138.

Hartgerink, J. D., et al., "Self-Assembly and Mineralization of Peptide-Amphiphile Nanofibers", Science, vol. 294, (Nov. 23, 2001), 1684-1688.

Li, B., et al., "VEDF and PlGF promote adult vasculogenesis by enhancing EPC recruitment and vessel formation at the site of tumor neovascularization", The FASEB Journal, vol. 20, (2006), 1495-1497.

Seeger, J. M., et al., "Improved in vivo endothelialization of prosthetic grafts by surface modification with fibronectin", J Vasc Surg, vol. 8, No. 4, (Oct. 1988), 476-82 (Abstract only).

Urbich, C. , et al., "Endothelial Progenitor Cells: Characterization and Role in Vascular Biology", Circulation Research, vol. 95, (2004), 343-353.

Advanced Cardiovascular Systems, Extended European search report dated Apr. 21, 2011 for EP Application No. 10186186.2.

Advanced Cardiovascular Systems, Extended EP Search Report dated May 20, 2011 for EP Application No. 10186197.9.

Chung, Y., et al., "Sol-gel transition temperature of PLGA-g-PEG aqueous solutions", Biomacromolecules, vol. 3, No. 3, (May 2002), 511-516.

* cited by examiner

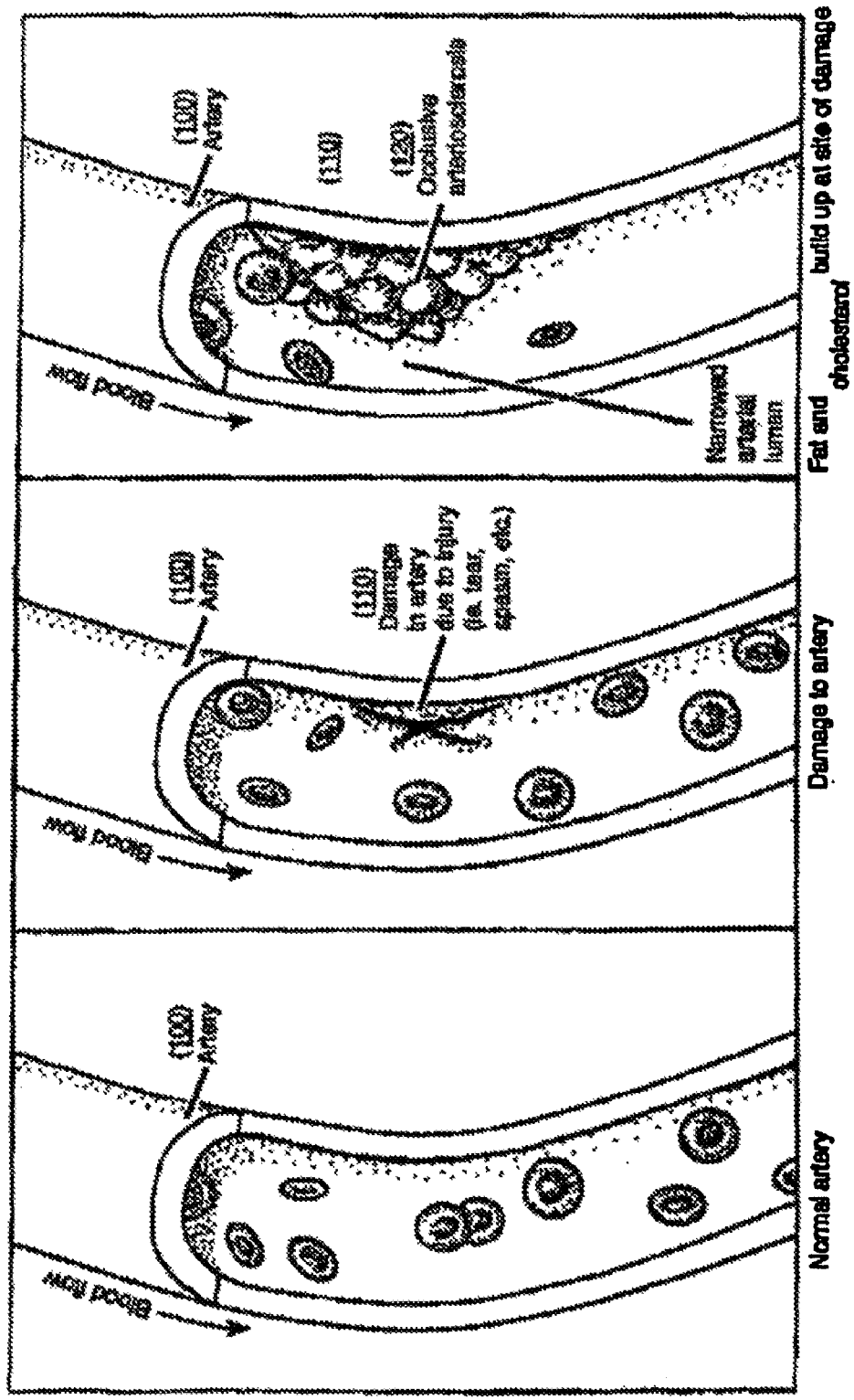

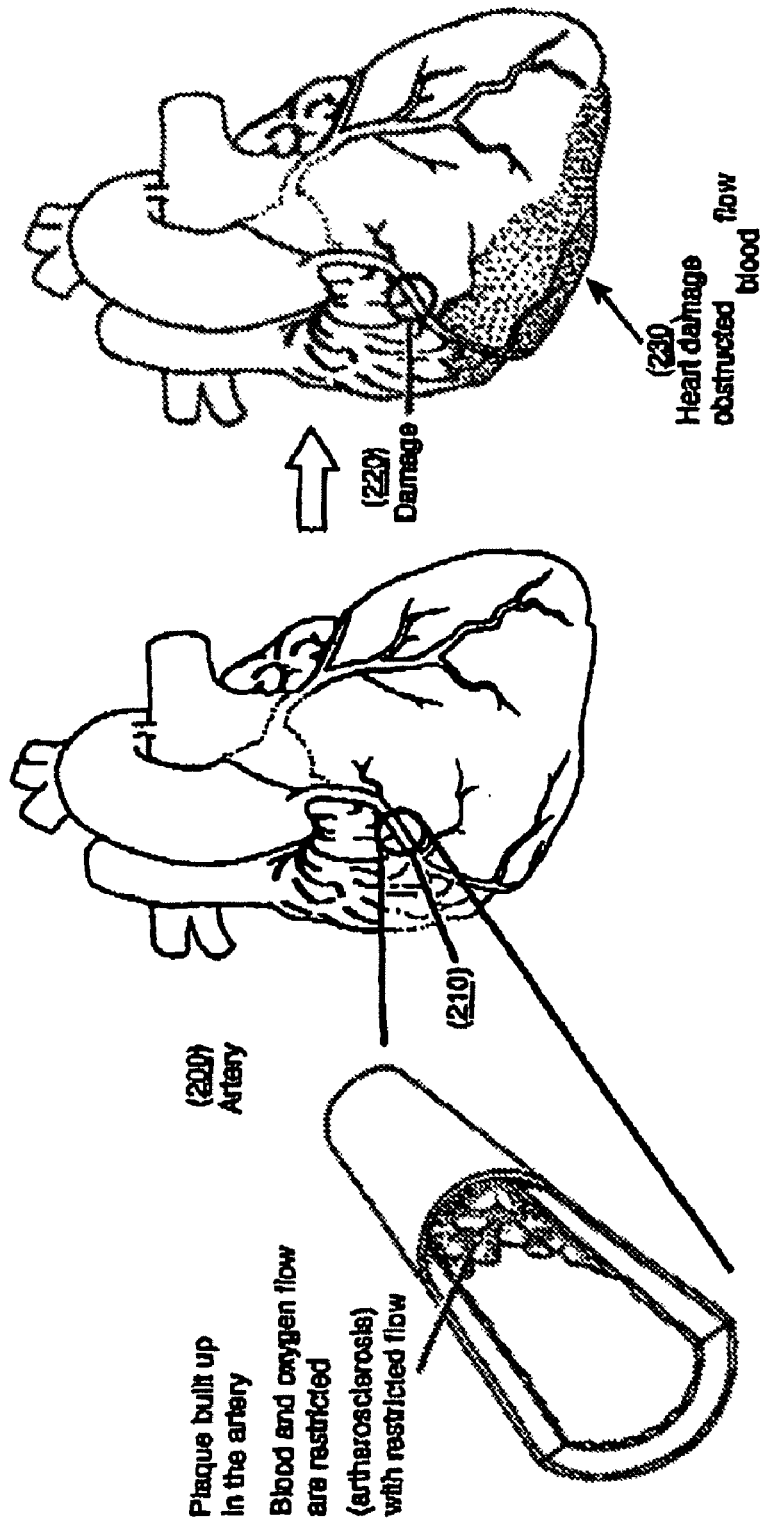

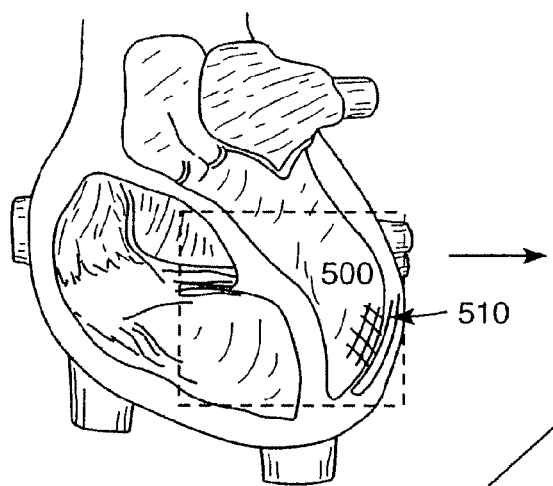
FIG. 5A
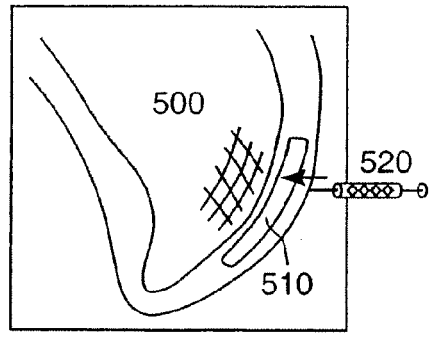
FIG. 5B
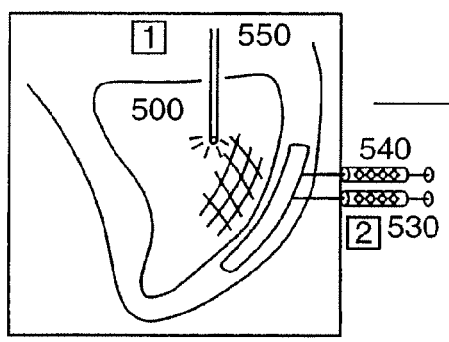
FIG. 5C
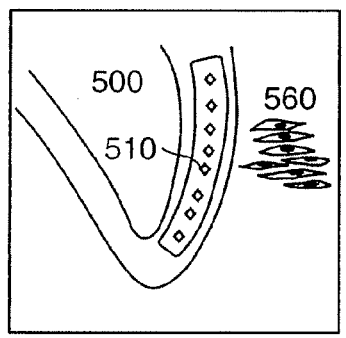
FIG. 5D
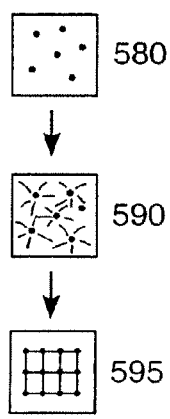
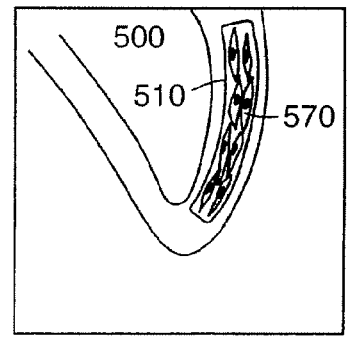
FIG. 5E

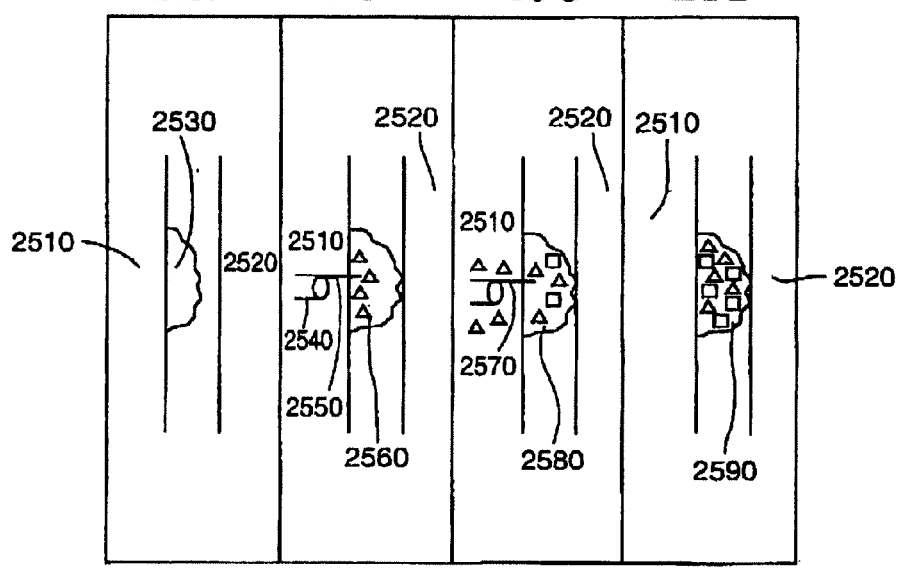

HIGH-VISCOSITY HYALURONIC ACID COMPOSITIONS TO TREAT MYOCARDIAL CONDITIONS

CROSS-REFERENCE

This application is a continuation-in-part of patent application Ser. No. 10/414,602, filed on Apr. 15, 2003, now pending.

FIELD

Composition(s) for the treatment of cardiomyoplasty, methods of manufacture and methods of treatment.

BACKGROUND OF THE INVENTION

Ischemic heart disease typically results from an imbalance between the myocardial blood flow and the metabolic demand of the myocardium. Progressive atherosclerosis with increasing occlusion of coronary arteries leads to a reduction in coronary blood flow. Blood flow can be further decreased by additional events such as changes in circulation that lead to hypoperfusion, vasospasm or thrombosis.

Myocardial infarction accounts for approximately 20% of all deaths. It is a major cause of sudden death in adults.

Myocardial Infarction (MI) is one form of heart disease that often results from the sudden lack of supply of oxygen and other nutrients. The lack of blood supply is a result of closure of the coronary artery that nourishes the particular part of the heart muscle. The cause of this event is generally caused by arteriosclerosis "hardening of the arteries" in coronary vessels.

Formerly, it was believed that an MI was caused from a slow procession of closure from, for example, 95% then to 100%. However, an MI can also be a result of minor blockages where, for example, there is a rupture of the cholesterol plaque resulting in blood clotting within the artery. Thus, the flow of blood is blocked and downstream cellular damage occurs. This damage can cause irregular rhythms that can be fatal even though the remaining muscle is strong enough to pump a sufficient amount of blood. As a result of this insult to the heart tissue, scar tissue tends to naturally form.

Even though systemic drugs presently exist to treat MI, such as ACE-inhibitors and Beta-blockers, a significant portion of the population that experiences a major MI ultimately develops heart failure. An important component in the progression to heart failure is remodeling of the heart due to mechanical forces resulting in uneven stress and strain distribution in the left ventricle. Once an MI occurs, remodeling of the heart begins. The principle components of the remodeling event include myocyte death, edema and inflammation, followed by fibroblast infiltration and collagen deposition, and finally scar formation. The principle component of the scar is collagen. Since mature myocytes of an adult are not regenerated, the infarct region experiences significant thinning. Myocyte loss is the major etiologic factor of wall thinning and chamber dilation that may ultimately lead to progression of cardiac myopathy. Myocyte death can and does occur. In other areas, remote regions experience hypertrophy (thickening) resulting in an overall enlargement of the left ventricle. This is the end result of the remodeling cascade. These changes in the heart result in changes in the patient's lifestyle and their ability to walk and to exercise. These changes also correlate with physiological changes that result in increase in blood pressure and worsening systolic and diastolic performance.

FIGS. 1A-1C illustrates blood flow by longitudinal cross sectioning of the artery. FIG. 1A illustrates a normal unobstructed artery. FIG. 1B illustrates artery damage due to a tear or spasm. FIG. 1C illustrates an artery with plaque build-up that reduces the blood flow demonstrated by the blocked blood cell above the atherosclerotic mass. Fat and cholesterol build up at the site of damage. This mass can be detected by methods currently available which methods include an echocardiogram, single photon emission computed tomography (SPECT), magnetic resonance imaging (MRI), or an angiogram.

FIGS. 2A-2B illustrate the progression of heart damage once the build-up of plaque induces an infarct to occur. The most common pathogenesis of this disease is occlusive intracoronary thrombus where a thrombus is covering an ulcerated stenotic plaque. This causes approximately 90% of transmural acute myocardial infarctions. Other possible triggers of an MI are vasospasms with or without coronary atherosclerosis and possible association with platelet aggregation. Another possible trigger is embolisms from left-sided mural thrombosis, vegetative endocarditis or a paradoxic embolism from the right side of the heart through a patent foramen ovale. FIG. 2A illustrates a site where blockage and restricted blood flow can occur from any of the indicated causes. FIG. 2B illustrates the extensive damage to the left ventricle that can be a result of the lack of oxygen and nutrient flow carried by the blood to the inferior region left ventricle of the heart. This area will likely undergo remodeling and eventually a scar will form and a non-functional (an area that does not contract) area will exist.

Significant atherosclerotic build-up can reduce the arterial lumen and reduce blood flow. Build-up is capable of rupturing resulting in a total or partial occlusion of the artery. Complete coronary occlusion will lead to an acute MI. Thus the T-cells, platelets, fibrin and multiple other factors and cells are blocked from progression through the blood stream and the result is an inadequate vascular supply as seen. This leads to myocyte death. Myocyte death, in addition to fibrosis in the form of collagen deposition, can lead to a compromised left ventricle and overload on the remaining myocytes. This process is further complicated by compensation of the remaining myocytes that hypertrophy (enlarge). This can cause the left ventricle to enlarge and if the cycle continues can result in eventual heart failure.

The morphological appearance of the infarcted heart tissue post-MI can vary. A transmural infarct involves the entire thickness of the left ventricular wall from the endocardium to the epicardium. It may extend into the anterior free wall and the posterior free wall. This damage may include extensions into the right ventricular wall. A sub-endocardial infarct may have multiple focal regions and a necrosis area may be confined to the inner one-third to one-half of the left ventricular wall. The evolutionary changes in a sub-endocardial infarct do not evolve the same as in a transmural MI.

Over time post-MI morphological changes occur. The gross morphological changes that occur over approximately a 7-week period are pallor of the myocardium that leads to some hyperemia, then a yellowing central to the damaged region. At approximately 15 days, the area is mostly yellow with soft vascular margins. This area eventually turns white from fibrosis. On a microscopic level, the initial examination reveals wavy myocardial fibers. Coagulation and necrosis with loss of cross striations occur followed by contraction bands, edema, hemorrhage, and neutrophilic infiltrate. Within 24-72 hours there is total loss of nuclei and striations and heavy neutrophilic infiltrate. Then macrophage and mononuclear infiltration begin resulting in a fibrovascular response. Once this fibrovascular response occurs then prominent granulation of the tissue follows. This ultimately leads to fibrosis and a scar is formed by about 7 weeks post MI.

FIGS. 3A-3B illustrate the occlusion of an artery that may lead to an MI. FIG. 3A illustrates the cross-section of a normal coronary artery with unobstructed lumen 301. The normal arterial wall 302 is made up of an intima layer 303, a media layer 304, and an adventitia layer 305. Within the arterial lumen, the intima is in direct contact with the flow of blood. This region is mostly made up of endothelial cells. The media layer is mostly smooth muscle cells and extracellular matrix proteins. Finally, the adventitia layer is primarily made up of collagen, nerves, blood vessels and lymph vessels. FIG. 3B illustrates a coronary artery with atherosclerosis. In this example, this artery is about 50 percent occluded (only 50 percent of the arterial lumen is free of obstruction). Thus, the obstructed artery may lead to damage observed in a ventricle of an MI subject.

After an MI has occurred, three layers of tissue can be distinguished. The infarct region has (1) the region of significant necrosis/apoptosis tissue (2) the border zone that consists of a large concentration of apoptotic and necrotic tissue as well as viable tissue and (3) the unaffected region that consists of mainly viable tissue. In the border zone the cells exist in an oxygen-deprived state due to the damage from the MI.

FIGS. 3C-3J illustrate the details of a post-MI remodeling of the ventricle. The progression of heart failure after an MI is a result of the remodeling of the heart after the infarct. The remodeling process causes the infarcted region of the heart to stretch and become thinner causing the left ventricular diameter to increase. As the heart continues to remodel, the stresses on the heart increase. FIG. 3C illustrates the cross striations 306 and central nuclei 307 of a healthy myocyte population.

FIGS. 3D-3J depict the progression of the remodeling of the ventricle post-MI. FIG. 3D illustrates an early acute MI. Here, there are prominent pink contraction bands that are indicated by reference number 308. FIG. 3E illustrates the increasing loss of striations and some contraction bands. The nuclei in this illustration are incurring karyolysis (a stage of cell death that involves fragmentation of a cell nucleus; the nucleus breaks down into small dark beads of damaged chromatin) 309. In addition, the neutrophils are infiltrating the damaged myocardial region. FIG. 3F illustrates an acute MI. The loss of nuclei and loss of cross striations are evident. There is extensive hemorrhaging on the infarct border 310. FIG. 3G illustrate the prominent necrosis and hemorrhaging 310, as well as the neutrophilic infiltrate 311. Subsequently, a yellowish center is formed within the damaged area with necrosis and inflammation surrounded by the hyperemic border. After 3-5 days post-MI, the necrosis and inflammation are extensive. There is a possibility of rupture at this point. FIG. 3H illustrates approximately one week after the MI with capillaries, fibroblasts and macrophages filled with hemosiderin (hemosiderin is a long-term reserve of iron in tissues) 312. In two to three weeks, granulation is the most prominent feature observed. FIG. 3I illustrates extensive collagen deposition 313 seen after a couple of weeks. Collagenous scarring occurs in subendocardial locations in remote myocardial infarct regions. FIG. 3J illustrates myocytes 314 after several weeks of healing post-MI. They are hypertrophied with large dark nuclei 315 and interstitial fibrosis 316. Interstitial fibrosis is also observed. These enlarged cells contribute to the enlarged left ventricle.

A complication of an MI is an aneurysm that looks like a bulge in the left ventricular wall. The aneurysm is made up of non-functional tissue that is unable to contract. Therefore, the ejection and stroke volume of the heart are reduced. Additionally, parts of this mass can form a mural thrombus that can break off and embolize to the systemic circulation.

SUMMARY OF THE INVENTION

Embodiments of bioscaffoldings formed of a single component bioscaffolding system, i.e., hyaluronic acid or a salt thereof, in a liquid component, are described. The liquid component may be a buffer solution and may include human plasma or a plasma product. In some embodiments, the liquid component is simply human plasma. The bioscaffolding also includes a plurality of cells. In some embodiments, the bioscaffolding additionally includes a protein, cytokine, or growth factor. The bioscaffolding may include other modifications.

The bioscaffolding may be used to enhance cellular cardiomyoplasty at a post-myocardial infarction site, chronic heart failure tissue site, or otherwise compromised cardiac tissue; provide gel paving to vulnerable plaque within a diseased arterial vessel; or provide homing of healthy cells and proteins to a cancer site. In addition, the bioscaffolding may be used as a coating on implantable or insertable medical device to be inserted into a patient.

To minimize embolic risk and maximize injectability, cytocompatibility, biocompatibility, and cell retention, properties related to hyaluronic acid or salt thereof may be controlled. Such properties may include molecular weight, molecular weight distribution, source, purity and concentration of the hyaluronic acid. Additional properties may include the characteristics of the type of liquid component in which the hyaluronic acid is contained, i.e., human plasma, buffer solution, or buffer solution with human plasma.

Methods of delivering the bioscaffolding include delivering the precursors of the bioscaffolding, which include at a minimum hyaluronic acid or a salt thereof in a liquid component and a plurality of cells suspended therein, by a minimally invasive method such as via the femoral artery or the subxiphoid. The bioscaffolding precursor may be injected or infused into the treatment site.

BRIEF DESCRIPTION OF THE DRAWINGS

FIG. 1A illustrates a longitudinally sectioned healthy artery and blood flow therein.

FIG. 1B illustrates a longitudinally sectioned damaged artery due to a tear or a spasm.

FIG. 1C illustrates a longitudinally sectioned occluded artery due to fat and cholesterol build up.

FIG. 2A illustrates plaque build-up in an artery that may result in restriction of blood and oxygen flow to the heart FIG. 2B illustrates the damage to the heart as a result of the plaque build-up in an artery that lead to an MI.

FIGS. 5A-5E illustrates the introduction of a pro-fibroblastic agent to an infarct zone and the formation of structural scaffolding

FIGS. 25A-25D illustrate the introduction of two separate components into an infarct region of the ventricle and formation of a structurally reinforcing composition at the infarct region using a catheter with retractable dual delivery ports.

DETAILED DESCRIPTION OF THE INVENTION

Definitions

Figure 3A:
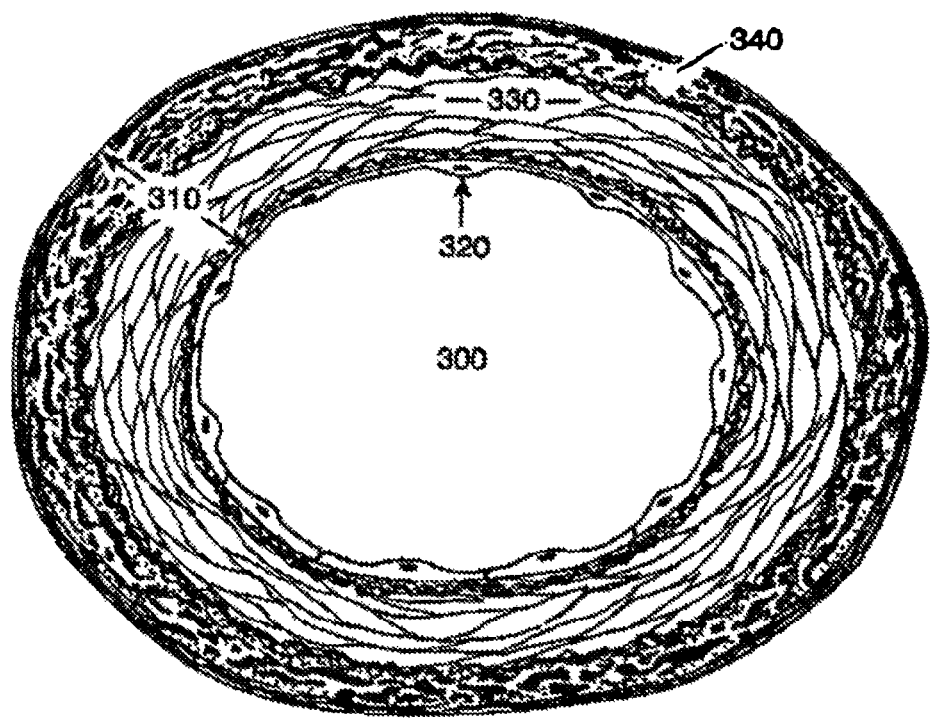
FIG. 3A illustrates a normal artery.
Figure 3B:
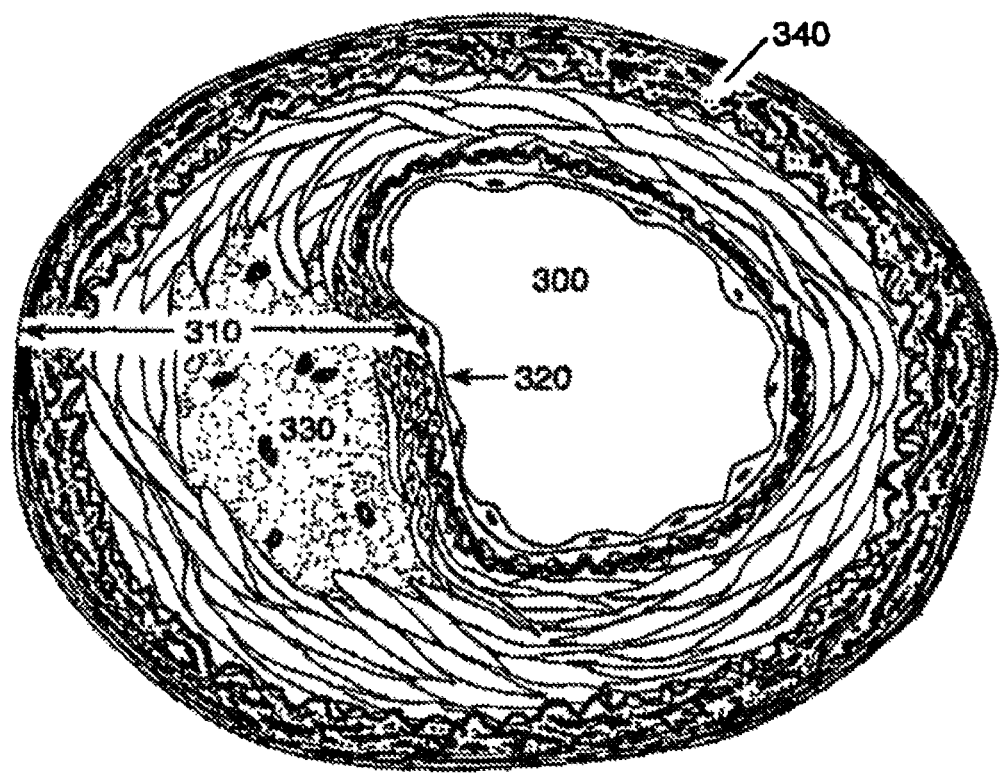
FIG. 3B illustrates an artery with arteriosclerosis (50 percent blockage) that may lead to an MI.
Figure 3C:
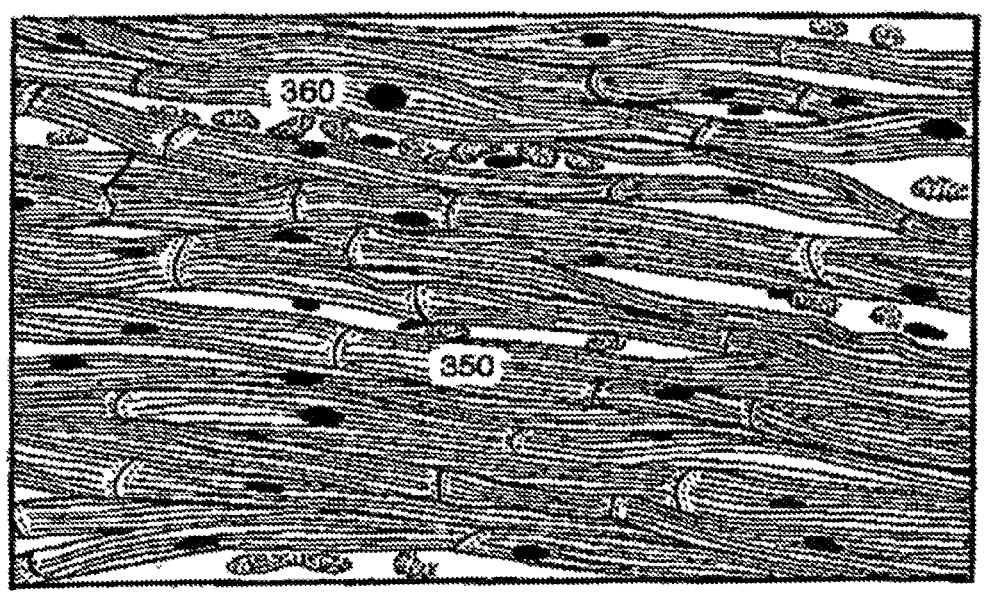
FIG. 3C illustrates normal myocardium.
Figure 3D:
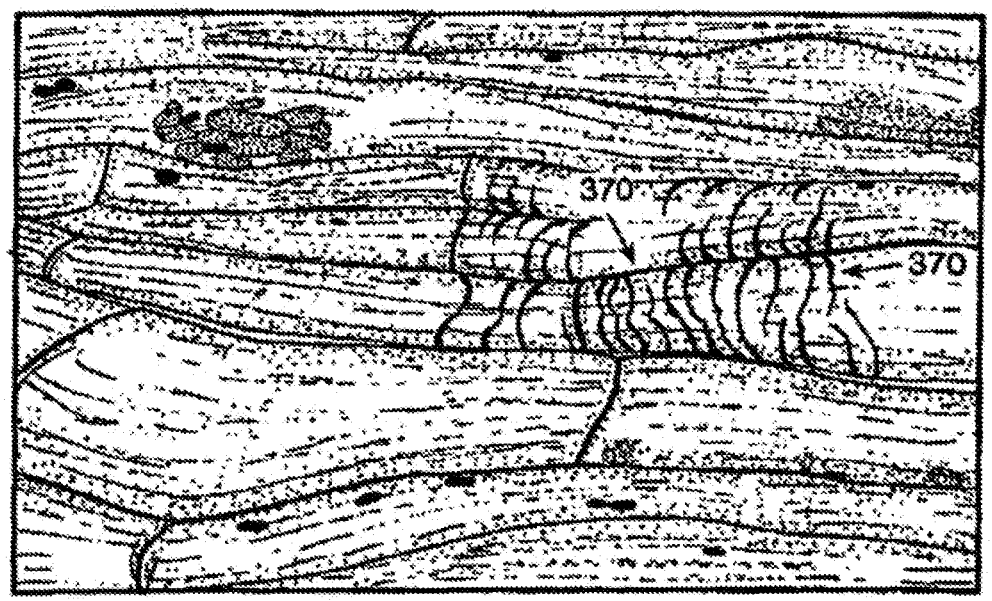
FIG. 3D illustrates an example of myocardium of an early acute myocardial infarction.
Figure 3E:
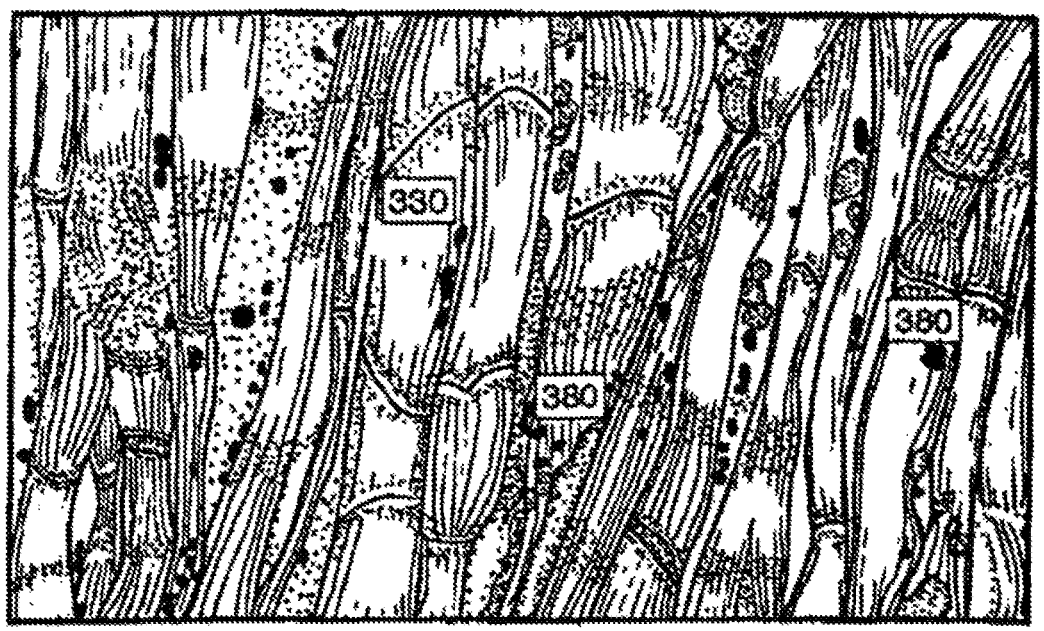
FIG. 3E illustrates an example of myocardium of an early myocardial infarction whereby a myocardium demonstrates increasing loss of cross-striations.
Figure 3F:
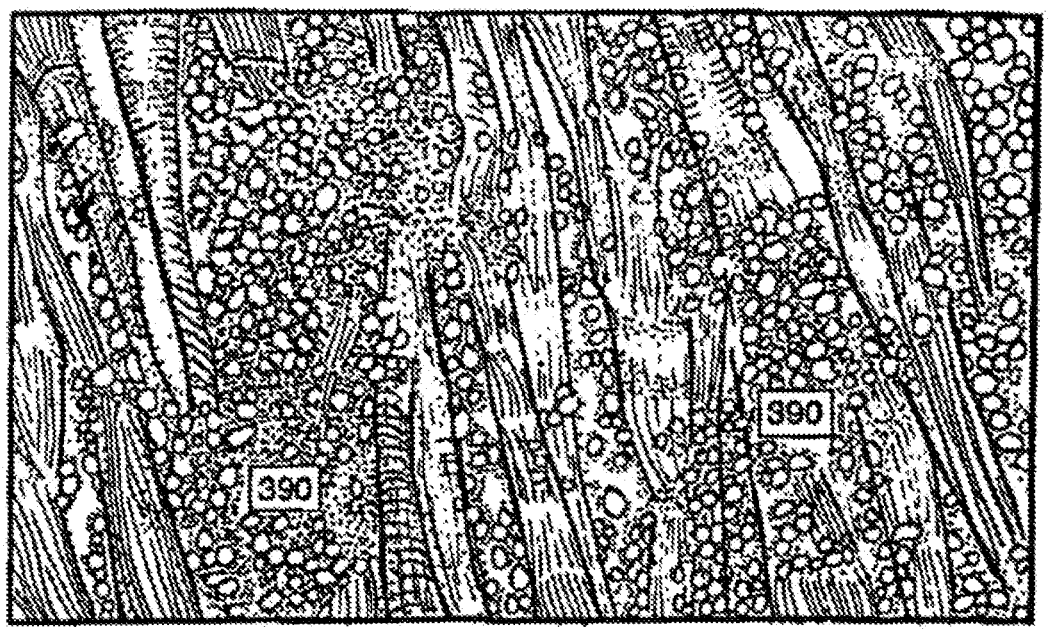
FIG. 3F illustrates an example of myocardium of an acute myocardial infarction and the loss of striations and the nuclei.
Figure 3G:
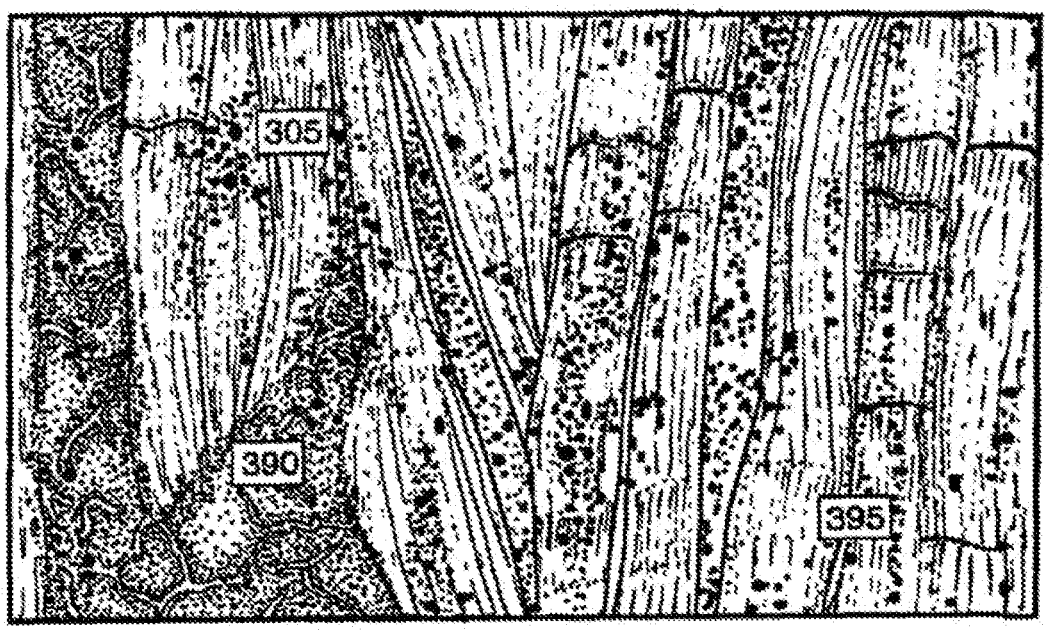
FIG. 3G illustrates an example of myocardium of an acute myocardial infarction resulting in neutrophilic infiltration and necrosis.
Figure 3H:
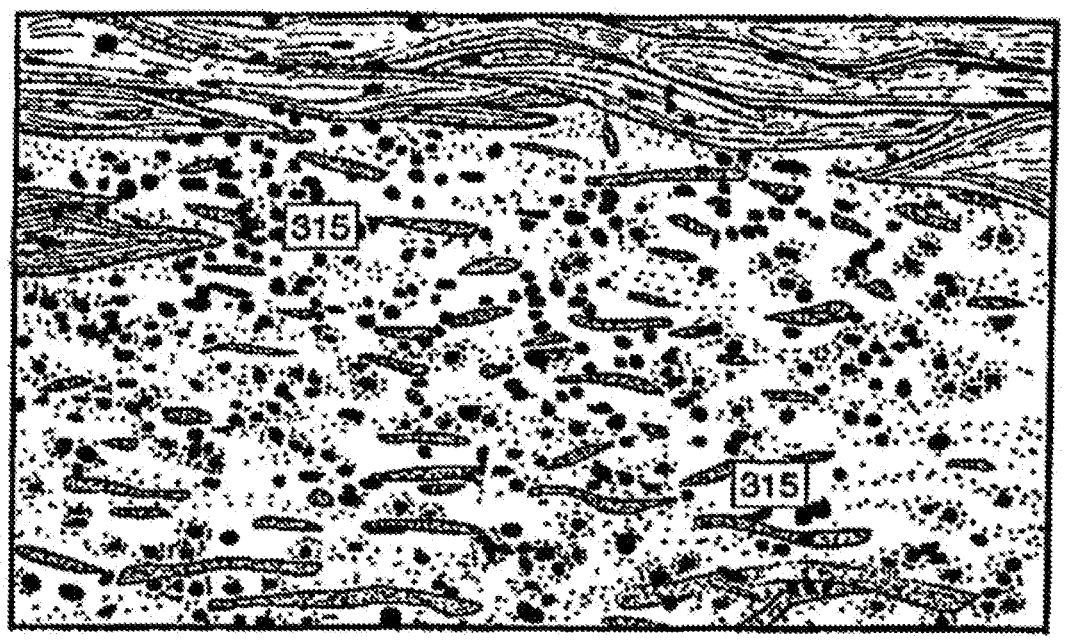
FIG. 3H illustrates an example of the myocardium of an acute myocardial infarction approximately one week after a myocardial infarction occurred.
Figure 3I:
FIG. 3I illustrates an example of the myocardium a couple of weeks after a myocardial infarction. A lot of collagen has been deposited at the site of damage.
Figure 3J:
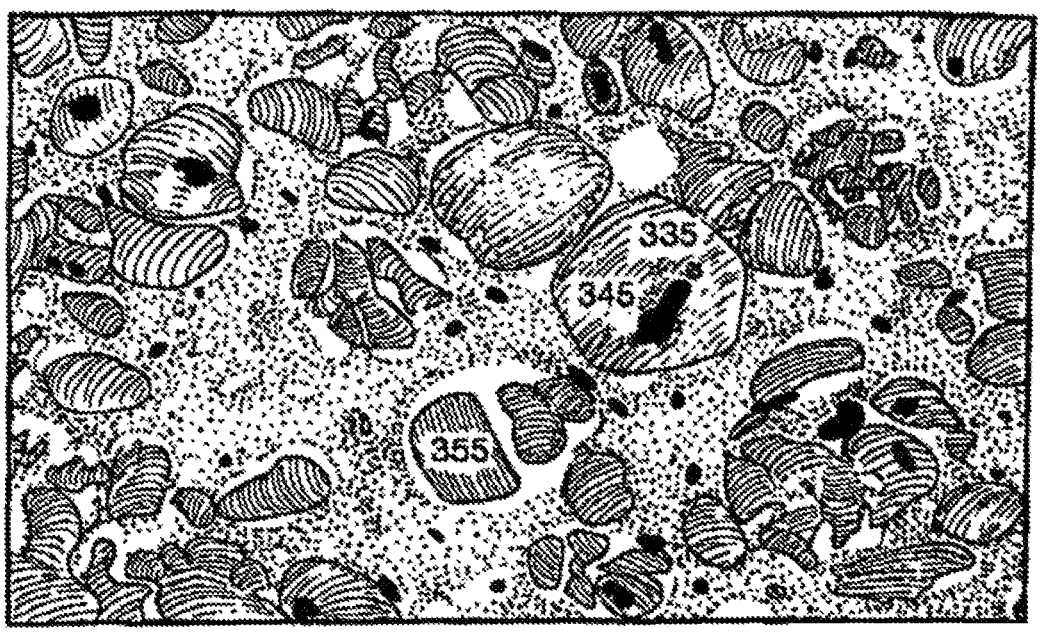
FIG. 3J illustrates myocardium several weeks after a myocardial infarction.

"a container"—a receptacle, such as a carton, can, vial, tube, bottle, or jar, in which material is held or carried.

"cardiomyocyte-like"—a cell(s) capable of converting to a cardiomyocyte(s) or a cell or components capable of functioning like a cardiomyocyte.

"polymer-forming"—any agent or agents capable of forming a gelatinous material either alone or in combination.

"delivery device"—an apparatus or system capable of depositing a solution, powder, concentrate, a single reagent and/or multiple reagents.

"pro-fibroblastic" agent—one or more compounds capable of retaining, inducing proliferation of and/or recruiting fibroblasts cells.

"compliance"—The ability of a blood vessel or a cardiac chamber to change its volume in response to changes in pressure has important physiological implications. In physical terms, the relationship between a change in volume ($\Delta V$) and a change in pressure ($\Delta P$) is termed compliance (C), where $C=\Delta V/\Delta P$. Compliance, therefore, is related to the ease by which a given change in pressure causes a change in volume. In biological tissues, the relationship between $\Delta V$ and $\Delta P$ is not linear. Compliance is the slope of the line relating volume and pressure that decreases at higher volumes and pressures. Another way to view this is that the "stiffness" of the chamber or vessel wall increases at higher volumes and pressures. Changes in compliance have important physiological effects in cardiac chambers and blood vessels.

Methods and compositions to treat a ventricle after a myocardial infarction (MI) are disclosed. In one embodiment, the infarct region or the area of the ventricle containing the infarct injury may be treated alone or in combination with other treatments. One benefit to such treatment is that the region of injury may be targeted with little or no affect on the outlying healthy heart tissue. In addition, another benefit of such treatment is that the treatment may prevent the loss of functionality of a region of injury due to the normal remodeling and scar forming procedure to mend an infarct region. Another benefit may be that the treatment may increase the compliance of the ventricle. Still another benefit is the reduction in thinning of a ventricular wall of an infarct zone. In the following description, structural reinforcement of the infarct region of the ventricle is described. Since most myocardial infarctions occur in the left ventricle most descriptions will be directed towards left ventricle repair. But, one of ordinary skill in the art will appreciate that treatment of the right ventricle may be achieved in a similar manner.

If the remodeling of the infarct region can be partially, substantially, or completely arrested prior to scar formation and ultimate thinning of the ventricular wall, functional tissue may be rescued. It is anticipated that the inhibition of scar formation and guided regeneration of viable cells will lead to increased wall strength and decreased collagen deposition instead of thinning and hypertrophied myocytes. Further, decreasing the probability of wall thinning and fortifying the influx of structural components such as fibroblasts might be beneficial and preferred over the current treatment of an MI, namely, continual exposure to systemic drugs to treat the symptoms and not the disease. Another benefit may be that any one of the treatments herein may result in an increase in compliance of the ventricle. Thus, any one or more combinations of these treatments may provide a potential for healing the infarct region and prevention of further complications.

In other embodiments, a kit (e.g., a pre-manufactured package) is disclosed. A suitable kit includes at least one agent and a lumen to house the agent. The agent has a property that may increase the modulus (tensile strength, "stiffness") of elasticity of the infarct region, increase compliance of the ventricle and/or prevent or reduce thinning caused by remodeling. The kit may be suitable, in one example, for use in the methods described Mapping of the Heart In each of the methods described herein, it is appreciated that specific areas of the heart may be targeted for application of any of the incorporated methods, thus there are techniques previously described that may be used for targeting the infarct region. One example of targeting a specific region such as an infarct zone uses a technique known as mapping the heart. See U.S. Pat. No. 6,447,504. The data are acquired by using one or more catheters that are advanced into the heart. These catheters usually have electrical and location sensors in their distal tips. Some of the catheters have multiple electrodes on a three-dimensional structure and others have multiple electrodes distributed over a surface area. One example of the later catheter may be sensor electrodes distributed in a circumferential series on the distal end portion of the catheter lying in planes spaced from each other. These techniques provide methods to characterize the condition of the heart in some situations using electrical potentials in the heart tissue as well as using electromechanical mapping, or ultrasonic mapping to map the viable and the non-viable regions of the heart such as, for example, the left ventricle and the infarct zone. In addition, the ultrasound waves may be used to determine the thickness of the heart tissue in the vicinity of the probe, for example, sensing the characteristic of the heart tissue by analyzing the ultrasound signals to determine the depth of the channels. Another method known as viability mapping (e.g., MRI, PET) may also be used. Viability mapping may be used to identify areas of the heart that are ischemic but still viable as well as area that have lost their viability due to infarction. These maps are based on electrophysiological data that indicate the flow of activation signals through the heart tissue. In addition, the data may be biomedical and/or mechanical data, such as data relating to variations in the thickness of the heart wall between systolic and diastolic stages of the heart cycle. The data that is used to analyze the heart by mapping may also be a combination of electrophysiological and biomedical data in order to more accurately locate and target the infarct region. In absence of viability mapping devices, one of ordinary skill in the art will appreciate that the location of the infarction may be also assessed through LV angiography or echocardiography where location of the akinetic or hypokinetic region may be identified.

Angiogenesis

After an MI, the infarct tissue as well as the border zone and the remote zone begin to remodel. The scar tissue forms in the infarct region as the granulation is replaced with collagen, causing the scar to thin out and stretch. The perfusion in this region is typically 10% of the healthy zone, decreasing the number of active capillaries. Increasing the number of capillaries may lead to an increase in compliance of the ventricle due to filling up with blood. Other benefits of increasing blood flow to the infarcted region include providing a route for circulating stem cells to seed and proliferate in the infarct region. Angiogenesis may also lead to increased oxygenation for the surviving cellular islets within the infarct region, or to prime the infarct region for subsequent cell transplantation for myocardial regeneration. In the border zone, surviving cells would also benefit from an increase in blood supply through an angiogenesis process. In the remote zone, where cardiac cells tend to hypertrophy and become surrounded with some interstitial fibrosis, the ability of cells to receive oxygen and therefore function to full capacity are also compromised; thus, angiogenesis would be beneficial in these regions as well. In one embodiment, angiogenesis will be stimulated in any region of the heart—infarct, border or remote—through delivery of angiogenesis-stimulating factors. Examples of these factors include but are not limited to isoforms of vasoendothelial growth factor (VEGF, e.g., VEGF121), fibroblast growth factor (FGF, e.g., b-FGF), Del 1, hypoxia inducing factor 1-alpha (HIF-1α), PR39, monocyte chemoattractant protein (MCP-1), nicotine, platelet derived growth factor (PDGF), insulin growth factor (IGF), transforming growth factor alpha (TGF-α), hepatocyte growth factor (HGF), estrogens, follistatin, proliferin, prostaglandin E1 or E2, tumor necrosis factor (TNF-α), interleukin 8 (IL-8), hematopoietic growth factors, erythropoietin, granulocyte colony-stimulating factors (G-CSF), platelet-derived endothelial growth factor (PD-ECGF), angiogenin. In other embodiments, these factors may be provided in a sustained release formulation as an independent factor or in combination with other factors or appropriate gene vectors with any of the platforms described in this application.

Delivery Systems

Any one or more catheters may be used to deliver embodiments of the single or multiple component bioscaffolding compositions to the infarct region area. Several catheters have been designed in order to precisely deliver compositions to a damaged region within the heart such as, for example, an infarct region. Several of these catheters have been described. See U.S. Pat. Nos. 6,102,926; 6,120,520; 6,251,104; 6,309,370; 6,432,119; 6,485,481. The delivery device may include an apparatus for intra-cardiac drug administration, including a sensor for positioning within the heart, a delivery device to administer the desired composition and amount of composition at the site of the position sensor. The apparatus may include, for example, a catheter body capable of traversing a blood vessel and a dilatable balloon assembly coupled to the catheter body comprising a balloon having a proximal wall. A needle may be disposed within the catheter body and includes a lumen having dimensions suitable for a needle to be advanced therethrough. The needle body includes an end coupled to the proximal wall of the balloon. The apparatus also includes an imaging body disposed within the catheter body and including a lumen having a dimension suitable for a portion of an imaging device to be advanced therethrough. The apparatus may further include a portion of an imaging device disposed within the imaging body adapted to generate imaging signal of the infarct region within the ventricle. The apparatus may be suitable for accurately introducing a composition at a desired treatment site.

In another embodiment, a needle catheter used to deliver the composition to the ventricle such as, for example, the infarct region may be configured to include a feedback sensor for mapping the penetration depth and location of the needle insertion. The use of a feedback sensor provides the advantage of accurately targeting the injection location. Depending on the type of composition administered, the target location for delivering the composition may vary. For example, one treatment may require multiple small injections within an infarct region where no two injections penetrate the same site.

In other embodiments, the catheter assembly may include a maneuverable instrument. This catheter assembly includes a flexible assembly. The catheter assembly may be deflectable and includes a first catheter, a second catheter, and a third catheter. The second catheter fits coaxially within the first catheter. At least one of the first catheter and the second catheter include a deflectable portion to allow deflection of that catheter from a first position to a second position, and the other of the first catheter and second catheter includes a portion which is pre-shaped (e.g., an angled portion formed by two segments of the angled portion). The third catheter has a sheath and a medical instrument positioned within the sheath. The third catheter fits coaxially within the second catheter. In another embodiment, a stabilizer, such as a donut-shaped balloon, is coupled to a distal portion of the third catheter. Each catheter is free to move longitudinally and radially relative to the other catheters. The catheter assembly may be used for the local delivery of bioagents, such as cells used for cell therapy, one or more growth factors for fibroblast retention, or vectors containing genes for gene therapy, to the left ventricle. In one embodiment, the catheter assembly described may be used in delivering cell therapy for heart failure or to treat one or more portions of the heart that are ischemic. The catheter assembly uses coaxially telescoping catheters at least one or more being deflectable, to position a medical instrument at different target locations within a body organ such as the left ventricle. The catheter assembly may be flexible enough to bend according to the contours of the body organ. The catheter assembly may be flexible in that the catheter assembly may achieve a set angle according to what the medical procedure requires. The catheter assembly will not only allow some flexibility in angle changes, the catheter assembly moves in a three coordinate system allowing an operator greater control over the catheter assembly's movement portion of the second catheter, allowing for the distal tip of the third catheter to be selectively and controllably placed at a multitude of positions. It will be appreciated that the deflectable portion may alternatively be on the second catheter and the pre-shaped portion may be on the first catheter.

In a further embodiment, an apparatus is disclosed. In one embodiment, the apparatus includes a first annular member having a first lumen disposed about a length of the first annular member, and a second annular member coupled to the first annular member having a second lumen disposed about a length of the second annular member, wherein collectively the first annular member and the second annular member have a diameter suitable for placement at a treatment site within a mammalian host. Representatively, distal ends of the first annular member and the second annular member are positioned with respect to one another to allow a combining of, for example, components of a bioscaffolding formulation introduced through each of the first annular member and the second annular member to allow a combining of treatment agents at the treatment site. Such an apparatus is particularly suitable for delivering a multi-component gel material (e.g., individual components through respective annular members that forms a bioerodable gel within an infarct region of a ventricle).

In the embodiments described herein, a composition delivery device and a method for delivering a composition are disclosed. The delivery device and method described are particularly suitable, but not limited to, local drug delivery in which a composition (possibly including multiple treatment agents and/or a sustained-release composition) is introduced via needle delivery to a treatment site within a mammalian host. A kit of a treatment agent composition is also described. One suitable application for a delivery device is that of a catheter device, including a needle delivery system. Suitable therapies include, but are not limited to, delivery of drugs for the treatment of arterial restenosis, therapeutic angiogenesis, or cancer treatment drugs/agents.

In other embodiments, larger doses of a composition may be considered, for example, about 2 mL to about 250 mL that may require any one or more of the delivery devices such as intra-venous retro infusion, intra-arterial infusion and needle catheter systems (e.g., INVIGOR available from Abbott Vascular, Santa Clara, U.S.A.) as well as subxyphoid approaches.

Various apparati (devices) and methods described herein can be used as a stand-alone injection needle/catheter during a surgical procedure such as an open heart surgery (e.g., coronary bypass graft (CABG)) procedure in which areas of the heart may be treated with, for example, growth factors, for affecting therapeutic angiogenesis, or incorporated into a catheter-based system to access locations that are commonly used in percutaneous transluminal coronary artery (PTCA) procedures. The apparati and methods may similarly be used in other surgical procedures such as cancer-related procedures (e.g., brain, abdomen, or colon cancer procedures or surgeries). Additionally, various apparati and methods described herein can be used in conjunction with various catheter-related or endoscopy procedures that generally require minimal invasive techniques to deliver a specific drug or growth factor into tissue. Examples of such procedures include, but are not limited to, orthoscopic surgery for joints (e.g., knee), laparoscopic surgery for the abdomen, and thoroscopic procedures related to chest injuries or treatments.

One concern of introducing a composition, whether adjacent a blood vessel to affect therapeutic angiogenesis, adjacent to a tumor to inhibit tumor growth, or to induce or stimulate collagen growth in orthoscopic procedures, is that the composition remain (at least partially) at the treatment site for a desired treatment duration (or a portion of the treatment duration). In this manner, an accurate dosage may be placed at a treatment site with reduced concern that the composition will disperse throughout other parts of the body, perhaps with serious consequences. In one embodiment, a composition and technique for retaining the composition (which may or may not include a treatment agent) at a treatment site (e.g., injection site) is described. In one embodiment, a treatment agent and a bioerodable gel or non-bioerodable gel or particle may be introduced at a treatment site (e.g., an injection site). The gel or particle(s) may be introduced prior to, after, or simultaneously with the treatment agent. In one preferred embodiment, the gel or particle(s) acts to retain the treatment agent at the treatment site by, representatively, sealing the treatment site or sealing the treatment agent at the treatment site. The use of a gel or particle(s) with a treatment agent can reduce the amount of treatment agent backflow from the injection site as well as reduce the load requirement of the treatment agent at the treatment site. For example, a bioerodable product such as a gel or particle may decrease the local pressure thereby further resulting in backflow reduction. A non-bioerodable product may also decrease the local pressure to reduce the backflow in a more permanent fashion and at the same time may also lead to an increase in compliance.

Using the above-mentioned techniques, an imaging modality may be added such as a contrast-assisted fluorescent scope that permits a cardiologist to observe the placement of the catheter tip or other instrument within the heart chamber. The contrast-assisted fluoroscopy utilizes a contrast agent that may be injected into heart chamber and then the area viewed under examination by a scope, thus the topography of the region is more easily observed and may be more easily treated. See U.S. Pat. Nos. 6,385,476 and 6,368,285. Suitable imaging techniques include, but are not limited to, ultrasonic imaging, optical imaging, and magnetic resonance imaging. Therefore, mapping of the heart is one technique that may be used in combination with the techniques proposed in the following embodiments. In one embodiment, an echocardiography procedure may be performed to confirm the occurrence and the location of the infarct region. In another embodiment, a computed axial tomography (CAT) scan may be performed to confirm an MI has occurred and to confirm the location of the infarct region.

In another embodiment, a method may include introducing a composition in a sustained release composition. The preferred period for sustained release of one or more agents is for a period of one to twelve weeks, preferably two to eight weeks. Methods for local delivery of sustained release agents include, but are not limited to, percutaneous devices such as intra-ventricular (coronary) or intravascular (coronary and peripheral) devices.

A. Fibroblast Retention and Recruiting Agents

1. Agents

Figure 4:
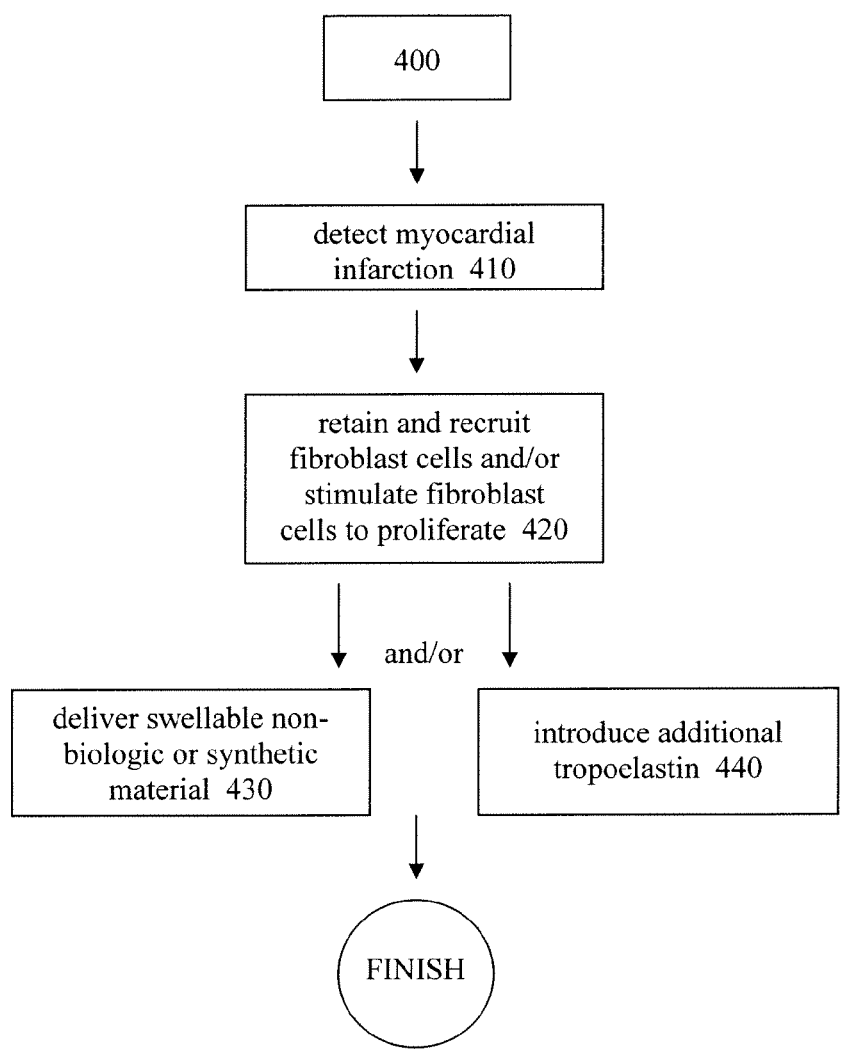
FIG. 4 illustrates various ways to restructure remodeling of the infarct region via retention and recruitment of fibroblasts and delivering a swellable reinforcing material and/or introduce additional tropoelastin to the infarct region.

FIG. 4 (block 400) illustrates one embodiment of a method to treat an infarct region of a left ventricle. This is an illustrative diagram only and any of the treatments may be used in parallel (e.g., at the same time) or sequentially or in any treatment combination. According to the method illustrated in FIG. 4, a myocardial infarction may be detected by, for example, an imaging, optical, or ultrasonic technique (block 410). Next, the area of the left ventricle is reinforced by retention or recruitment of surrounding fibroblasts cells (block 420). In FIG. 4, one option to encourage fibroblast occupancy of the infarct zone includes the use of swellable material (block 430) delivered to the infarct zone. Another method includes the delivery of tropoelastin to the site to encourage the occupancy of fibroblasts to the infarct zone (block 440). It has been demonstrated that injections of fibroblasts into a scar region may improve the structural integrity of a terminally injured heart in a rabbit model. See Hutcheson, K. A., et al., *Comparison of Benefits on Myocardial Performance of Cellular Cardiomyoplasty with Skeletal Myoblasts and Fibroblasts,* Cell Transplant, May-June 2000, pp. 359-368, 9(3). Since the fibroblasts naturally infiltrate the scar during the healing process, it would be beneficial to attract these cells in larger numbers, or to induce their proliferation in the infarct region such that fibroblasts are encouraged to remain in the region for a prolonged period, or, alternatively, permanently remain in the region. In addition, a further benefit of retaining fibroblasts in an infarct region may be to convert the fibroblast phenotype to influence the conversion from non-contractile cell to a muscular cell. The conversion is promoted in the presence of growth factors such as, for example TGF-β1. Therefore, the infarct region may be treated with agents that encourage fibroblast retention and recruitment. Suitable treatment agents that may modify or recruit fibroblasts include but are not limited to, angiotensin II, fibroblast growth factor (FGF basic and acidic), insulin growth factor (IGF), TGF-β in any of its isoforms, vascular endothelial growth factor (VEGF) in any of its isoforms, tumor necrosis factor-alpha (TGF-α), platelet-derived growth factor-BB (PDGF-BB), angiogenin, angiopoietin-1, Del-1, follistatin, granulocyte colony-stimulating factor (G-CSF), pleiotrophin (PTN), proliferin, transforming growth factor-alpha (TGF-α), vascular permeability factor (VPF), and LIH (leukemia inhibitory factor), genes that encode these proteins, transfected cells carrying the genes of these proteins, small molecules and pro-proteins that also contain these recruiting properties.

In one embodiment, basic fibroblast growth factor may be introduced to the infarct region by at least one of the methods described. In one embodiment, any of the described agents may be introduced in one or more doses in a volume of about 1 μL to 1 mL. In another embodiment, any of the described agents may be introduced in one or more doses in a volume of about 1 μL to 300 μL. In another embodiment, any of the described agents may be introduced in one or more doses in a volume of about 1 μL to 100 μL. In a preferred embodiment, the any of the described agents may be introduced in one or more doses in a volume of about 1 μL to 50

In alternate embodiments, the treatment volume may be larger (e.g., intravenous pressure perfusion (IV) route). These volumes may range from about 2 mL to about 250 mL. Alternatively, these volumes may range from about 2 mL to about 100 mL. In other embodiments, these volumes may range from about 2 mL to about 30 mL.

2. Sequence of Treatment

FIGS. 5A-5E illustrates the introduction and action of fibroblast retention and recruitment at treatment site 500. Detection of acute myocardial necrosis may be performed by, for example, electrocardiography or by a more modern technology. For example, one technology, such as $^{99m}$Technetium-pyrophosphate or $^{111}$In-antimyosin antibody imaging, has recently been approved by the Food and Drug Administration. With both these two tracers, results are obtained 24-48 hours after acute infarction and therefore, the clinical utility of these techniques have been limited. Another agent, $^{99m}$Tc-glucarate, produces results within an hour after acute myocardial infarction. See Iskandrian, A. S., et al., *Nuclear Cardiac Imaging: Principles and Applications,* 1996, $2^{nd}$ Ed. Once the MI is detected, the exact location of the infarct may be identified using magnetic resonance imaging. Then, the ventricle infarct region 510 may be treated by reinforcement. An agent 520 (for example, tropoelastin) is introduced to the infarct region 510. One way the agent may be introduced to the area is percutaneously with the use of a catheter 550. A distal end of catheter 550 is advanced to the infarct region 510 and the agent 520 is released. Then, fibroblasts 560 are recruited to the infarct region 510 resulting intreated infarct region 570. FIG. 5E illustrates the fibroblast reinforcement of the infarct area.

3. Description of Several Possible Treatment Agent(s) and Deliveries a. Tropoelastin In some embodiments, the combination of promoting fibroblast retention and migration into the infarct region may be achieved with the addition of tropoelastin. Elastin is a highly pliable extracellular protein. In vivo, it is usually in a cross-linked insoluble state. A linear non-cross-linked soluble precursor is available that is referred to as tropoelastin. Tropoelastin can be made by recombinant methods and is commercially available. Tropoelastin is an approximately 70-kDa protein consisting of alternating hydrophobic regions, responsible for elasticity, and cross-linking domains.

Additionally, it ends with a hydrophilic carboxy-terminal sequence containing its only two cysteine residues. Tropoelastin is a protein that is prominent in the skin of an infant; as one matures, less and less of this protein is produced. Tropoelastin is sometimes used as an important marker of some heart conditions, such as MI, since it is released into the bloodstream following heart injury. The production of recombinant tropoelastin in bacterial systems has greatly simplified the availability of tropoelastin. In addition, it provides a valuable means for obtaining human tropoelastin. Purification from human aortas was greatly simplified compared with tissue extraction methods, but relatively low yields were obtained. The purification from the aortas posed the potential for degradation of the polypeptide. Recently, human tropoelastin cDNA has also been expressed in bacteria as a fusion with influenza NS1 protein. See Indik, Z., et al., *Production of Recombinant Human Tropoelastin: Characterization and Demonstration of Immunologic and Chemotactic Activity*, Arch. Biochem. Biophys., July 1990, pp. 80-86, 280(1). This isoform of tropoelastin, containing exon 26A and the signal peptide, was the first form of human tropoelastin to be obtained for study. In view of tropoelastin's extreme amino acid usage, a synthetic human tropoelastin gene has been constructed containing codons designed to optimize expression in *E. coli*. See Martin, S. L., et al., *Total Synthesis and Expression in Escherichia coli of a Gene Encoding Human Tropoelastin*, Gene, Mar. 10, 1995, pp. 154-166, 154 (2). This synthetic gene is expressed at high levels in soluble form both as a fusion with glutathione S-transferase and directly, as the mature polypeptide. Alternatively, a simplified purification scheme using alcohol solubilization and eliminating the need for cyanogen bromide (CNBr) treatment resulted in significantly higher yields. Therefore, purified or genetically engineered tropoelastin is available. Recombinant forms of tropoelastin have proved to be viable alternatives to tissue-derived tropoelastin. Recombinant tropoelastin reacts with elastin antibodies, is a chemotactic agent, demonstrates coacervation ability and has the some similar characteristics to naturally occurring tropoelastin (i.e., circular dichroism).

In one embodiment, any of the described agents may be introduced in one or more doses in a volume of about 1 µL to 1 mL. In another embodiment, any of the described agents may be introduced in one or more doses in a volume of about 1 µL to 300 µL. In another embodiment, any of the described agents may be introduced in one or more doses in a volume of about 1 µL to 100 µL. In a preferred embodiment, any of the described agents may be introduced in one or more doses in a volume of about 1 µL to about 50 µL.

b. Microparticles and Growth Factors Delivery

One embodiment of a composition suitable for the described method includes the use of a bioerodable microparticle harboring one or more of the aforementioned growth factors. The bioerodable microparticle may consist of a bioerodable polymer such as poly(lactide-co-glycolide). The composition of the bioerodable polymer is controlled to release the growth factor over a period of 1-2 weeks. It was previously demonstrated that biodegradable microparticles made of, for example, poly(lactide-co-glycolide) were capable of controlled release of an oligonucleotide. These microparticles were prepared by the multiple emulsion-solvent evaporation technique. In order to increase the uptake of the oligonucleotide into the microparticles it was accompanied by poly(ethylenimine) (PEI). The PEI also tended to make the microparticles more porous thus facilitating the delivery of the oligonucleotide out of the particles. See De Rosa, et al., *Biodegradable Microparticles for the Controlled Delivery of Oligonucleotides*, Int. J. Pharm., Aug. 21, 2002, pp. 225-228, 242(1-2). In one preferred embodiment of a composition, the bioerodable microparticle may be a PLGA polymer 50:50 with carboxylic acid end groups. PLGA is a base polymer often used for controlled release of drugs and medical implant materials (i.e., anti-cancer drugs such as anti-prostate cancer agents). Two common delivery forms for controlled release include a microcapsule and a microparticle (e.g., a microsphere). The polymer and the agent are combined and usually heated to form the microparticle prior to delivery to the site of interest (Mitsui Chemicals, Inc). As the microparticles erode, a porous network of the microparticle composition is formed in the infarct region resulting in a matrix with a controlled pore size. As porous network is formed at least one angiogenic and/or pro-fibroblastic factor may be released encouraging the in-growth of new capillaries. One embodiment, the bioerodable polymer harbors the growth factor TGF-β1. In one embodiment, the PLGA polymer 50:50 with carboxylic acid end groups harbor TGF-β1 for slow release. It is preferred that each microparticle may release at least 20 percent of its contents and, more preferably, around 90 percent of its contents. In one embodiment, the microparticle harboring at least one angiogenic and/or pro-fibroblastic agent will degrade slowly over time releasing the factor or release the factor immediately upon contact with the infarct area in order to rapidly recruit fibroblasts to the site. In another embodiment, the microparticles may be a combination of controlled-release microparticles and immediate release microparticles. A preferred rate of deposition of the delivered factor will vary depending on the condition of the subject undergoing treatment.

Another embodiment of a composition suitable for the described method includes the use of non-bioerodable microparticles that may harbor one or more of the aforementioned growth factors. The growth factors may be released from the microparticle by controlled-release or rapid release. The microparticles may be placed directly in the infarct region. By directly placing the particles in the infarct region, they may also provide bulk for the region for reinforcement. The non-bioerodable microparticle may consist of a non-bioerodable polymer such as an acrylic based microsphere, for example, a tris-acryl microsphere (provided by Biosphere Medical). In one embodiment, non-bioerodable microparticles may be used alone or in combination with an agent to increase compliance of a ventricle. In another embodiment, non-bioerodable microparticles may be used alone or in combination with an agent to recruit fibroblasts and/or stimulate fibroblast proliferation. In addition, non-bioerodable microparticles may be used to increase compliance and recruit fibroblasts to an infarct region of a ventricle.

In one embodiment, the treatment agent compositions suitable for reinforcement of the infarct zone are rendered resistant to phagocytosis by inhibiting opsonin protein absorption to the composition of the particles. In this regard, treatment agent compositions including sustained release carriers include particles having an average diameter up to about 10 microns. In other situations, the particle size may range from about 1 µm to about 200 µm. The larger size particles may be considered in certain cases to avoid macrophage frustration and to avoid chronic inflammation in the treatment site. When needed, the particle size of up to 200 µm may be considered and may be introduced via an intra-ventricular catheter or retrograde venous catheter for any of the embodiments herein to avoid chronic inflammation due to macrophage influx into the treatment site.

One method of inhibiting opsonization and subsequent rapid phagocytosis of treatment agents is to form a composition comprising a treatment agent disposed with a carrier for example a sustained release carrier and to coat the carrier with an opsonin inhibitor. One suitable opsonin-inhibitor includes polyethylene glycol (PEG) that creates a brush-like steric barrier to opsonization. PEG may alternatively be blended into the polymer constituting the carrier, or incorporated into the molecular architecture of the polymer constituting the carrier, as a copolymer, to render the carrier resistant to phagocytosis. Examples of preparing the opsonin-inhibited microparticles include the following.

For the encapsulation polymers, a blend of a polyalkylene glycol such as polyethylene glycol (PEG), polypropylene-1,2 glycol or polypropylene-1,3 glycol is co-dissolved with an encapsulating polymer in a common organic solvent during the carrier forming process. The percentage of PEG in the PEG/encapsulating polymer blend is between five percent and 60 percent by weight. Other hydrophilic polymers such as polyvinyl pyrolidone, polyvinyl alcohol, or poly(oxyethylene)-poly(oxypropylene) copolymers can be used in place of polyalkylene glycols, although polyalkylene glycols and more specifically, PEG is generally preferred.

Alternatively, a diblock or triblock copolymer of an encapsulating polymer such as poly (L-lactide), poly (D,L-lactide), or poly (lactide-co-glycolide) with a polyalkylene glycol may be prepared. Diblocks can be prepared by: (i) reacting the encapsulating polymer with a monomethoxy polyakylene glycol such as PEG with one protected hydroxyl group and one group capable of reacting with the encapsulating polymer, (ii) by polymerizing the encapsulating polymer onto the monomethoxy polyalkylene glycol, such as PEG, with one protected group and one group capable of reacting with the encapsulating polymer; or (iii) by reacting the encapsulating polymer with a polyalkylene glycol such as PEG with amino functional termination. Triblocks can be prepared as described above using branched polyalkylene glycols with protection of groups that are not to react. Opsonization resistant carriers (microparticles/nanoparticles) can also be prepared using the techniques described above to form sustained-release carriers (microparticles/nanoparticles) with these copolymers.

A second way to inhibit opsonization is the biomimetic approach. For example, the external region of cell membrane, known as the "glycocalyx," is dominated by glycosylated molecules that prevent non-specific adhesion of other molecules and cells. Surfactant polymers consisting of a flexible poly (vinyl amine) backbone, brush-like dextran and alkanoyl (hexanoyl or lauroyl) side chains constrain the polymer backbone to lie parallel to the substrate. Hydrated dextran side chains protrude into the aqueous phase, creating a glycocalyx-like monolayer coating that suppresses plasma protein deposition on the foreign body surface. To mimic glycocalyx, glycocalyx-like molecules can be coated on the carriers (e.g., nanoparticles or microparticles) or blended into a polymer constituting the carrier to render the treatment agent resistant to phagocytosis. An alternate biomimetic approach is to coat the carrier with, or blend in, phosphorylcholine or a synthetic mimetic of phosphatidylcholine, into the polymer constituting the carrier.

For catheter delivery, a carrier comprising a treatment agent (e.g., the composition in the form of a nanoparticle or microparticle) may be suspended in a fluid for delivery through the needle, at a concentration of about one percent to about 20 percent weight by volume. In one embodiment, the loading of the treatment agent in a carrier is about 0.5 percent to about 30 percent by weight of the composition. Co-encapsulated with protein or small molecule treatment agents could be stabilizers that prolong the biological half-life of the treatment agent in the carrier upon injection into tissue. Stabilizers may also be added to impart stability to the treatment agent during encapsulation. Hydrophilic polymers such as PEG or biomimetic brush-like dextran structures or phosphorylcholine are either coated on the surface or the carrier, grafted on the surface of the carrier, blended into the polymer constituting the carrier, or incorporated into the molecular architecture of the polymer constituting the carrier, so the carrier is resistant to phagocytosis upon injection into the target tissue location.

Any one or more catheters may be used to deliver embodiments of the single or multiple component bioscaffolding compositions to the infarct region area. Several catheters have been designed in order to precisely deliver agents to a damaged region within the heart, for example, an infarct region. Several of these catheters have been described. See U.S. Pat. Nos. 6,309,370 6,432,119; 6,485,481. The delivery device may include an apparatus for intra-cardiac drug administration, including a sensor for positioning within the heart, a delivery device to administer the desired agent and amount at the site of the position sensor.

c. Microparticles and Angiogenic and Pro-fibroblastic Agents

The microparticles may be prepared as microparticles harboring an angiogenic and/or pro-fibroblastic agent. On the other hand, the microparticles may be prepared and then the angiogenic and/or pro-fibroblastic agent introduced into the microparticle, for example, by diffusion prior to introduction to the infarct region. In the later example, the microparticles might also be coated with the factor and, upon introduction to the infarct region, the factor immediately recruits fibroblasts to the area. Additionally, the microparticle-factor composition may consist of any combination of the above-mentioned treatments. In other embodiments, it may be necessary to add at least one pharmaceutically acceptable inhibitor to the microparticles that prevents decomposition of the angiogenic or pro-fibroblastic agent.

d. Microparticle Components

FIG. 4 also describes a method to structurally reinforce the infarct region. This method may be combined with any of the methods describing introducing angiogenic and/or fibroblast-recruiting agents, for example growth factors, to the infarct region to retain and/or promote fibroblast migration to this zone. Microparticles capable of taking up fluid will be introduced to the infarct region. Examples of these microparticles include swellable non-biological or synthetic biological particles (block 430). The microparticles are introduced to the infarct zone and become trapped in the tissue. The microparticles tend to immediately start to swell. The swollen microparticles remain lodged in the tissue and provide reinforcement to the ventricular wall and add thickness to the thinning infarct region.

The dimensions of the infarct zone may determine the size range of the microparticles and the number of microparticles introduced to the infarct region. This will insure that the optimum post-hydrated microparticle mass is achieved. An embodiment relates to microparticles that are about 200 microns or less in diameter. In another embodiment the microparticles may be about 20 microns or less in diameter. In a preferred embodiment, the particle size may be about 5-10 microns in diameter. Particles of about 20 microns or less may also include an opsonization inhibitor (previously discussed). The swellable microparticles may be a range of sizes introduced to the infarct region. In one embodiment, the swellable non-biological material may be a hydrogel microsphere material. These microparticles are available commercially (A.P. Pharma or BioSphere Medical). These microparticles are resistant to non-specific absorption and are bio-stable.

In other embodiments, hydrogels may be used as a treatment for a myocardial infarction. Examples of hydrogel materials are high molecular weight poly(acrylamide) or high molecular weight polyvinylpyrrolidone) (PVP). Typically, the monomer supplied in these products contains di-functional monomers such as di-vinyl benzene, ethylene glycol dimethylacrylate or bis-acrylamide acetate resulting in the formation of a cross-linked network resistant to dissolution in an aqueous environment or to stimulate controlled magnitude angiogenic response. These components may be used to generate microspheres. Alternatively the di-functional polymers may be used to synthesize a hydrogel microsphere.

In one embodiment of the invention the first component of a biosynthetic polymeric gel may be (acrylamidomethyl) cellulose acetate propionate and the second component may be a dithiol functional polyethylene glycol polymer (by Shearwater Polymers). In another embodiment, the first component of a biosynthetic polymeric gel may be (acrylamidomethyl) cellulose acetate proprionate and the second component may be a reduced peptide sequence. In a further embodiment, the reduced peptide sequence could be biologically derived such as the amino acid sequence, glycine-cysteine-tyrosine-lysine-asparagine-arginine-aspartic acid-cysteine-glycine. A dual bore needle system may deliver both components separately one at a time or simultaneously to an infarct zone. The thiol-group(s) of the thiol-containing component may undergo nucleophilic addition to the acrylamide functional group of the first component. This forms the elastomeric structurally reinforcing gel.

In other embodiments, the delivery of a non-biologic or synthetic gel may be combined with angiogenic and/or fibroblast recruiting agents utilizing microparticles capable of releasing the agents at a rate optimal for fibroblast retention and migration in the infarct region.

In one embodiment, tropoelastin suspended in a solution, such as saline, is introduced to the infarct region for structural reinforcement of the ventricular wall. Another embodiment includes the introduction of tropoelastin suspended in saline in the presence of copper ions. Another embodiment includes the introduction of tropoelastin in the presence of a converting enzyme. Another embodiment includes the introduction of tropoelastin in the presence of lysyl oxidase. Once introduced to the infarct zone, the solution forms elastin by cross-linking via a lysine residue oxidation. The cross-linked elastin remains in the infarct region to fortify the tissue and enhance the modulus (wall strength/elongation=modulus) of elasticity.

4. Methods for Introduction and Action

Referring again to FIGS. 5A-5E, the introduction and action of pro-fibroblastic agents to the treatment site 500 to recruit fibroblast cell growth is illustrated. The pro-fibroblastic agent may be introduced (perfused) to the infarct region 510 by a minimally invasive procedure such as by a sub-xiphoid or a percutaneous procedure. The solution may alternatively be injected into the infarct region 510 during an open chest procedure. The mode of introduction of the pro-fibroblastic agent(s) by a percutaneous injection includes one of the following: an intra-ventricular (coronary) catheter, a transvascular needle catheter, intra-coronary infusion, and retrograde venous perfusion. One percutaneous route for a catheter is via a femoral artery traversing through and then across the aortic arch into the left ventricle. Imaging techniques can guide the catheter to the infarct region. The infarct region 510, for example, may be distinguished from healthy tissue using an MRI technique. A catheter having imported the MRI data may then be guided directly to the infarct region. Once the agent is distributed throughout the infarct region 510, fibroblasts 560 may be attracted to the area by chemotactic responses (FIG. 5D). The fibroblast cells that infiltrate the area may proliferate in the area. Once the fibroblasts proliferate they form a reinforcing mass to the region and strengthen the infarct region 510. The fibroblast in this aspect may act as a structurally reinforcing agent in the treated infarct region 570 (FIG. 5E). These cells add bulk to the area and replace the degraded myocytes that normally lead to a thinning of the infarct regional wall. In turn, the viable fibroblast cells release factors that may recruit other cells into the area for further reinforcement of the infarct zone.

In one embodiment, any of the described agents may be introduced in one or more doses in a volume of about 1 µL to 1 mL. In another embodiment, any of the described agents may be introduced in one or more doses in a volume of about 1 µL to 300 µL. In another embodiment, any of the described agents may be introduced in one or more doses in a volume of about 1 µL to about 100 µL. In a preferred embodiment, the any of the described agents may be introduced in one or more doses in a volume of about 1 µL to about 50 µL. If an agent is introduced via an IV or an IC route the volumes may range from about 1 mL to about 500 mL.

Any one or more catheters may be used to deliver embodiments of the single or multiple component bioscaffolding compositions to the infarct region area. Several catheters have been designed in order to precisely deliver agents to a damaged region within the heart for example an infarct region. Several of these catheters have been described. See U.S. Pat. Nos. 6,309,370; 6,432,119; 6,485,481. The delivery device may include an apparatus for intra-cardiac drug administration, including a sensor for positioning within the heart, a delivery device to administer the desired agent and amount at the site of the position sensor.

B. Multiple Component Systems for Infarct Reconstruction

1. Component One

Figure 6:
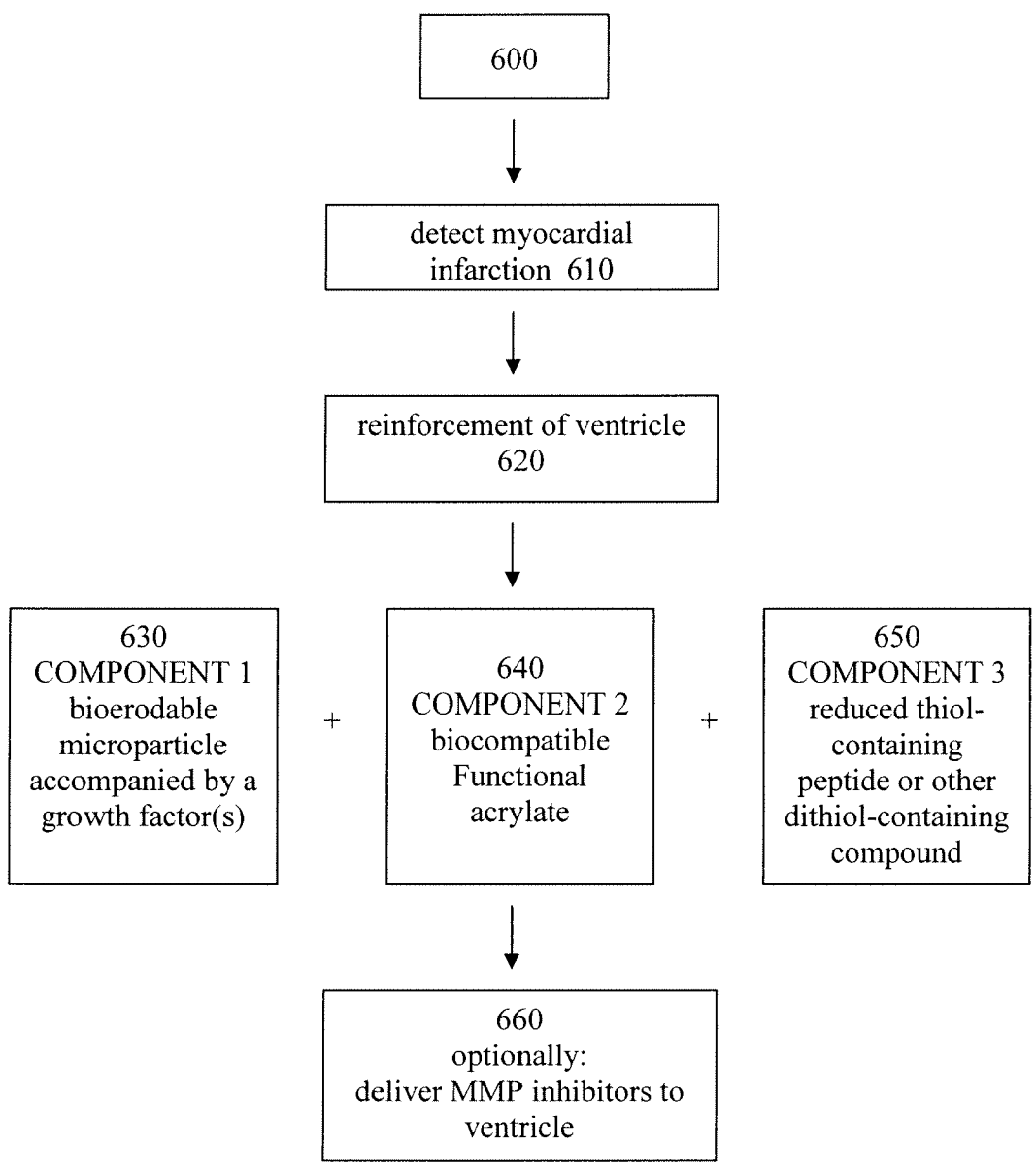
FIG. 6 illustrates a multi-component method for structurally reinforcing an infarct region.

To prevent heart failure, it has been proposed that cardiomyocytes can be directly introduced into the infarct region to restore cardiac function cells of various origins, including embryonic and adult stem cells. The viability of tissue engineering for a myocardial infarct zone requires that oxygen and nutrient supplies are readily available, as well as a mode for removal of waste products from cell metabolism. The cells in these areas also need a supporting structure for adherence. The bioerodable gel with angiogenic and/or fibroblast recruiting agents previously discussed provides this later supporting structure. In the literature, it is known that the introduction of scaffolding with a pore size of less than 10 microns leads to a tightly fibrotic encapsulated scaffold with poor capillary in-growth. On the other hand, as demonstrated in FIG. 9, if the scaffolding pore diameter is around 20 microns, cellular encapsulation of the scaffold system is well perfused with capillary in-growth leading to fibrotic poor cellular rich region. FIG. 6 (block 600) illustrates one embodiment of a method to treat an infarct region of a left ventricle by reinforcement of the ventricle (block 620). As further illustrated in FIG. 9, the force is distributed more evenly at the infarct region 910 and ventricular remodeling is partially, substantially, or completely prevented.

In one embodiment, separate components are included to provide a network such as described above (see, e.g., FIG. 6). A multi-component composition includes a first component, a second component, and a third component. In this particular composition, the resulting combination of components provides a porous scaffolding to enhance capillary in-growth. In one embodiment, the first component is bioerodable microparticles accompanied by a growth factor (block 630). The microparticles dispersed throughout the resulting matrix may be approximately 20 microns. In another embodiment, as illustrated in FIG. 9, the first component of the composition may be introduced in a minimally invasive procedure 960 such as a percutaneous procedure. A distal end of the catheter is advanced to the infarct region 910 and bioerodable microparticles 920 are released. In a further embodiment, the first component of the composition may be introduced via an intra-ventricular needle device 930 to the infarct region 910. In a further embodiment, an intra-ventricular needle device may be used to administer multiple injections to the infarct region to introduce the first component of the composition. The first component may serve in one aspect as a domain to promote cell growth. In addition, porosity may be controlled that leads to capillary in-growth. The factor or other agent may release over a 1-2 week period. One embodiment may be that the first component includes PLGA 50:50 (previously described) with carboxylic acid end groups. An example of capillary in-growth to the domain provided by the first component may be facilitated by the release of angiogenic factors 980. One embodiment includes microparticles containing angiogenic factors 980 that release rapidly after introduction to the infarct region. This tends to result in a rapid angiogenic response.

Biomaterials have been employed to conduct and accelerate otherwise naturally occurring phenomena, such as tissue regeneration in wound healing in an otherwise healthy subject; to induce cellular responses that might not normally be present, such as healing in a diseased subject or the generation of a new vascular bed to receive a subsequent cell transplant; and to block natural phenomena, such as the immune rejection of cell transplants from other species or the transmission of growth factor signals that stimulate scar formation in certain situations.

2. Component Two

Figure 9A:
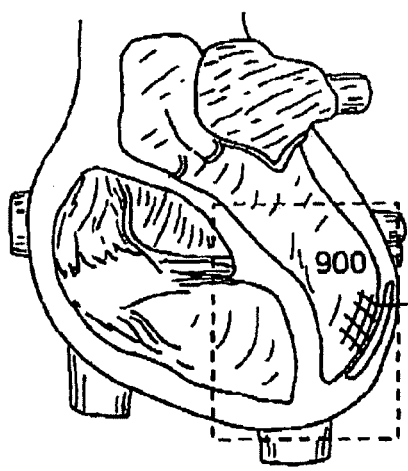
FIG. 9A shows a perspective front side view of a hert having an infarct region in the left ventricle.
Figure 9B:
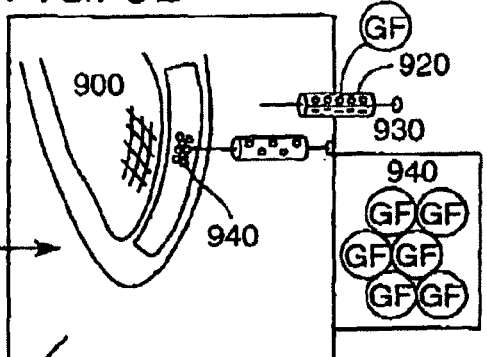
FIG. 9B shows the heart of FIG. 9A followingihe introduction of a first component to the infarct region.
Figure 9C:
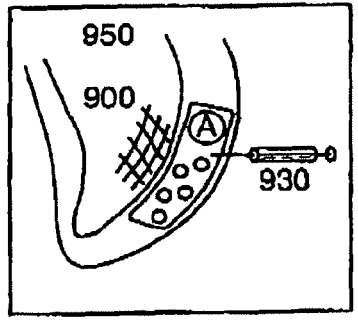
FIG. 9C shows the heart of FIG. 9A and the introduction of a second component to the infarct regions.
Figure 9D:
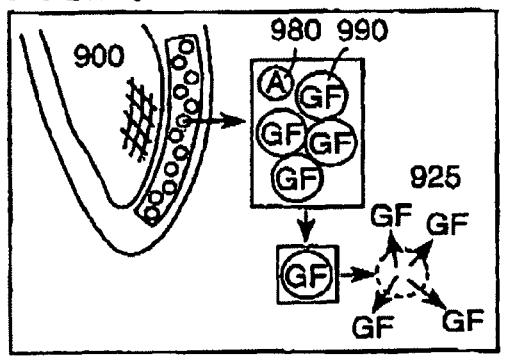
FIG. 9D shows the heart of FIG. 94 following the introduction of the second component.
Figure 9E:
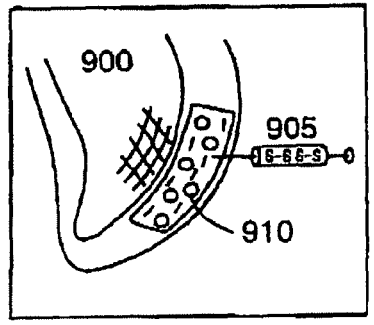
FIG. 9E shows the heart of FIG. 9A and the introduction of a third comnent to the infarct region.
Figure 9F:
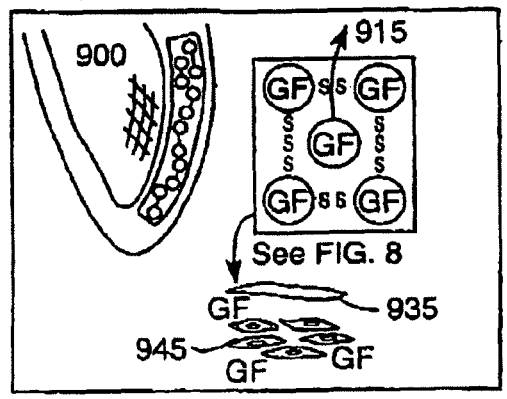
FIG. 9F shows the heart of FIG. 9A following the introduction of the third component.

A second component (block 640) of the multi-component composition according to a method may be an acrylate agent that is biocompatible. A second component serves in one aspect to disperse the first component in order to form a more uniform scaffold over the entire infarct region 910 and may include border zone as well. It may be an oligomeric di- (or multi-) functional acrylate agent based on a component that is biocompatible. An embodiment of the two-component composition may include a second component such as di-acryloyl polyethylene glycol, tetra-acryloyl polyethylene glycol (PEG), or (acrylamidomethyl) cellulose acetate proprionate. In order to dissolve the acrylamide functional cellulose component, ethanol or a biocompatible is required. The second component disperses the microparticles 970/990 thereby acting as a suspending media. It is known that PEG-coated microparticles 990 are less inflammatory and are not likely to elicit a fibrotic response. Thus, it in one aspect may serve as an anti-opsonization agent. Thus, they serve as a camouflage from the immune system for introduction of the microparticles to the infarct region. One embodiment includes the injection of both the growth factor containing microparticles and the scaffold-forming matrix (acryloyl functional macromer) using a dual bore needle. FIG. 9F illustrates the final formation of the scaffold gel 915. The introduction of the two solutions simultaneously creates the near instantaneous (around 10 seconds) formation of the gel with a microparticle network embedded within the scaffolding 915. As the microparticles 925 decompose, growth factors are released promoting the capillary formation within the matrix. In addition, cells 935 begin to grow in the infarct region 910. These cells release proteases that may result in the decomposition of the scaffolding ultimately creating additional area for cellular in-growth. In addition, the cells secrete their own extracellular matrix, the polymer degrades, and the resulting tissue may eventually become a completely natural environment. The decomposition products may be cleared from the area by the renal system since capillary re-growth may occur.

3. Component Three

Another component of a multi-component composition and method is illustrated in FIG. 6 (block 650) and FIG. 9. A third component includes one of the following: thiol-containing peptide or a di- or multi-functional biocompatible such as dithio-PEG. An example of a thiol-containing peptide 905 may be polycysteine oligomers. An example of this is a protected form of a polycysteine oligomer, poly-S-CBZ-L-cysteine or poly-5-benzyl-L-cysteine (Sigma Chemical P0263 and P7639 respectively). These agents can be de-protected using standard organic chemistry protocols. See Berger, et al., *Poly-L-cysteine*, J. Am. Chem. Soc., Sep. 5, 1956, pp. 4483-4488, 78. The preparation of these thiol-containing agents is well known. See Zervas, L., et al., *On Cysteine and Cystine Peptides. II. S-Acylcysteines in Peptide Synthesis*, J. Am. Chem. Soc., May 5, 1963, pp. 1337-1341, 85(9). Additional agents that may function as the third component of a multi-component composition may be naturally occurring peptides. In one embodiment, the third component of the multi-component scaffolding may be one of the following consisting of poly-S-CBZ-L-cysteine and poly-5-benzyl-L-cysteine. In another embodiment of a multi-component composition, the third component of the multi-component scaffolding may be a naturally occurring peptide. In a further embodiment of a multi-component composition the third component of a multi-component scaffolding may be the naturally occurring peptide glycine-cysteine-tyrosine-lysine-asparagine-arginine-aspartic acid-cysteine-glycine peptide sequence. The third component preferably contains at least two thiol groups. FIGS. 9A-9F illustrates the introduction of the three components to the infarct region to treat an MI. One embodiment may be the introduction of the first component and the second component 920/930 through a dual bore needle and then the introduction of a thiol-containing third component 905 through a second needle. FIG. 9F illustrates a schematic of the final structure 915 that subsequently recruits cells 935 (fibroblast growth) and capillary 945 in-growth into the infarct region. The thiol-containing component 905 may be used to decrease the rate of decomposition of the scaffold and control release of the fibroblast recruiting components of the microparticles.

Any one or more catheters may be used to deliver embodiments of the single or multiple component bioscaffolding compositions to the infarct region area. Several catheters have been designed in order to precisely deliver agents to a damaged region within the heart for example an infarct region. Several of these catheters have been described. See U.S. Pat. Nos. 6,309,370; 6,432,119; 6,485,481. The delivery device may include an apparatus for intra-cardiac drug administration, including a sensor for positioning within the heart, a delivery device to administer the desired agent and amount at the site of the position sensor.

C. Multi-Component System for Infarct Reconstruction and Infarct Re-Oxygenation

The progression of heart failure after an MI is a result of the remodeling of the heart after infarct. In the remodeling processes the heart becomes thinner and the diameter increases in response to a decrease in heart output, in an effort to maintain a continual cardiac output. This process of thinning results in an increase in the radius of the heart and the stresses on the heart increase.

It has been shown that perfluorocarbon compounds have a high affinity for gases, for example carbon dioxide and oxygen. The ability of perfluorocarbons to transport oxygen is approximately eighteen times greater than blood plasma in a comparable volume of each component. In addition, it was shown that the half-life for oxygenation/deoxygenation is approximately three and one half times faster for many perfluorinated compounds as compared to hemoglobin. Thus, perfluoro compounds may be used in tissues to aid in the re-oxygenation of an affected region such as an infarct region.

Figure 7:
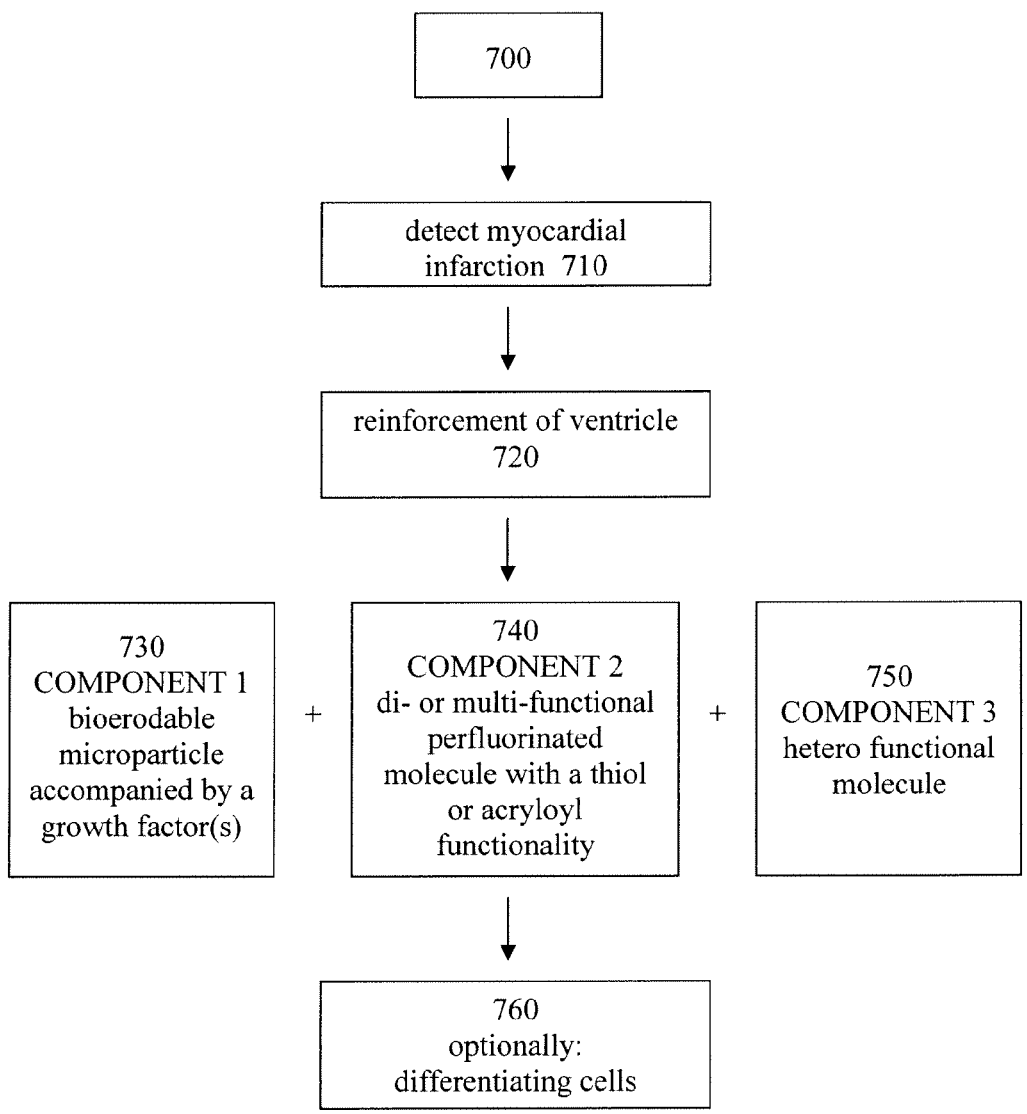
FIG. 7 illustrates a multi-component method for structurally reinforcing an infarct region and/or facilitating oxygenation of an infarct region.
Figure 8:
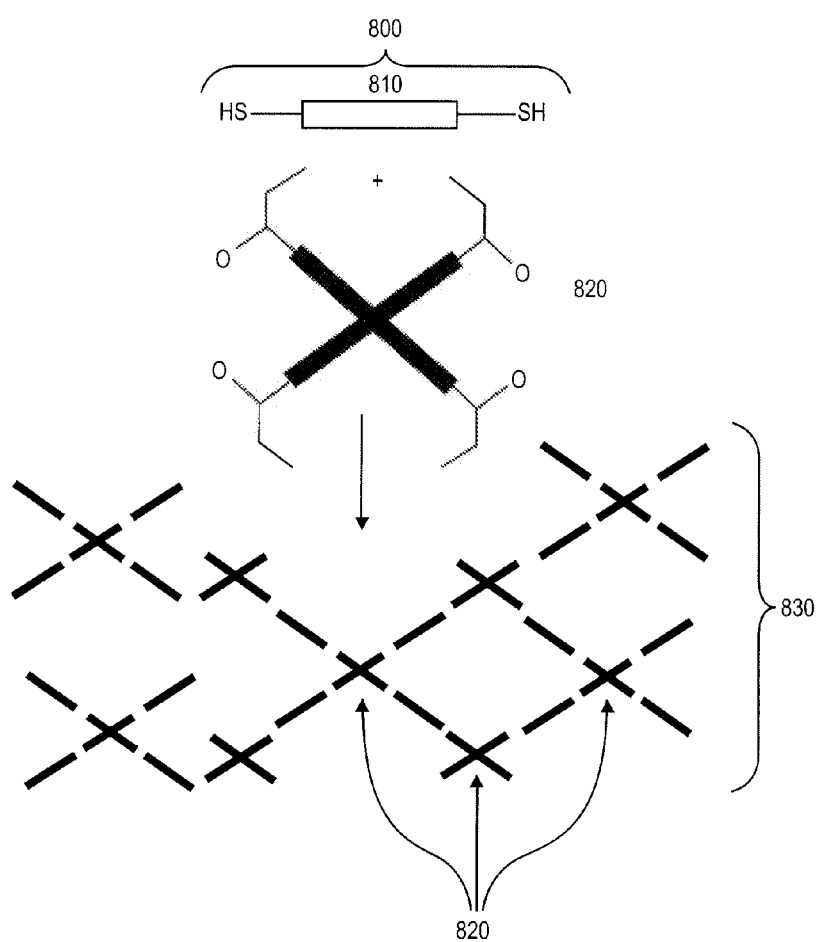
FIG. 8 illustrates a general structure of the first and of the second component of FIG. 7.

FIG. 7 (block 700) illustrates an embodiment of the reinforcement of the ventricle (block 720). The myocardial infarction is located detected (block 710). Then, the components are delivered to the region via a minimally invasive procedure by methods previously described and/or by catheter delivery. It was previously disclosed that the addition of a thiol functionality (e.g., component three of FIG. 6) in the presence of an electron deficient double bond, such as an acryloyl functionality (e.g., component two of FIG. 6), can undergo a Michael addition reaction. Under basic conditions, the thiol functionality becomes hyper-nucleophilic and rapidly (<10 seconds) forms a bond with the acryloyl functionality (see FIG. 10). As illustrated in FIG. 6, a gel may be formed to prevent infarct expansion and/or bulking, thus preventing a remodeling of the heart that may lead to heart failure. As illustrated in FIG. 7, the first component (block 730) includes a bioerodable polymerl and the second component (block 740) includes a di-functional or multifunctional perfluorinated compound with a thiol or acryloyl functionality to enhance oxygenation of the tissue. The third component (block 750) includes a hetero-functional molecule with a reactive functionality on one side of the spacer group, and a cell binding peptide sequence, such as the peptide sequences previously described, on the terminal end. One example of a peptide sequence includes the Arg-Gly-Asp (RGD) sequence. FIG. 8 illustrates in schematic form the reaction of thiol component 800 and acryloyl functional group 820 to form one compound 830 of the three-component system of FIG. 7. This three-component system may be introduced to the infarct region by similar minimally invasive methods as described previously. Examples of this three-component system are discussed in the example section.

In one embodiment, any of the described agents may be introduced in one or more doses in a volume of about 1 μL to 1 mL. In another embodiment, any of the described agents may be introduced in one or more doses in a volume of about 1 μL to 300 μl. In another embodiment, any of the described agents may be introduced in one or more doses in a volume of about 1 μL to 100 μL. In a preferred embodiment, the any of the described agents may be introduced in one or more doses in a volume of about 1 μL to 50 μL. Intra-ventricular and intra-coronary routes may be required which would involve larger treatment volumes (for example about 2 mL to about 250 mL).

Figure 10:
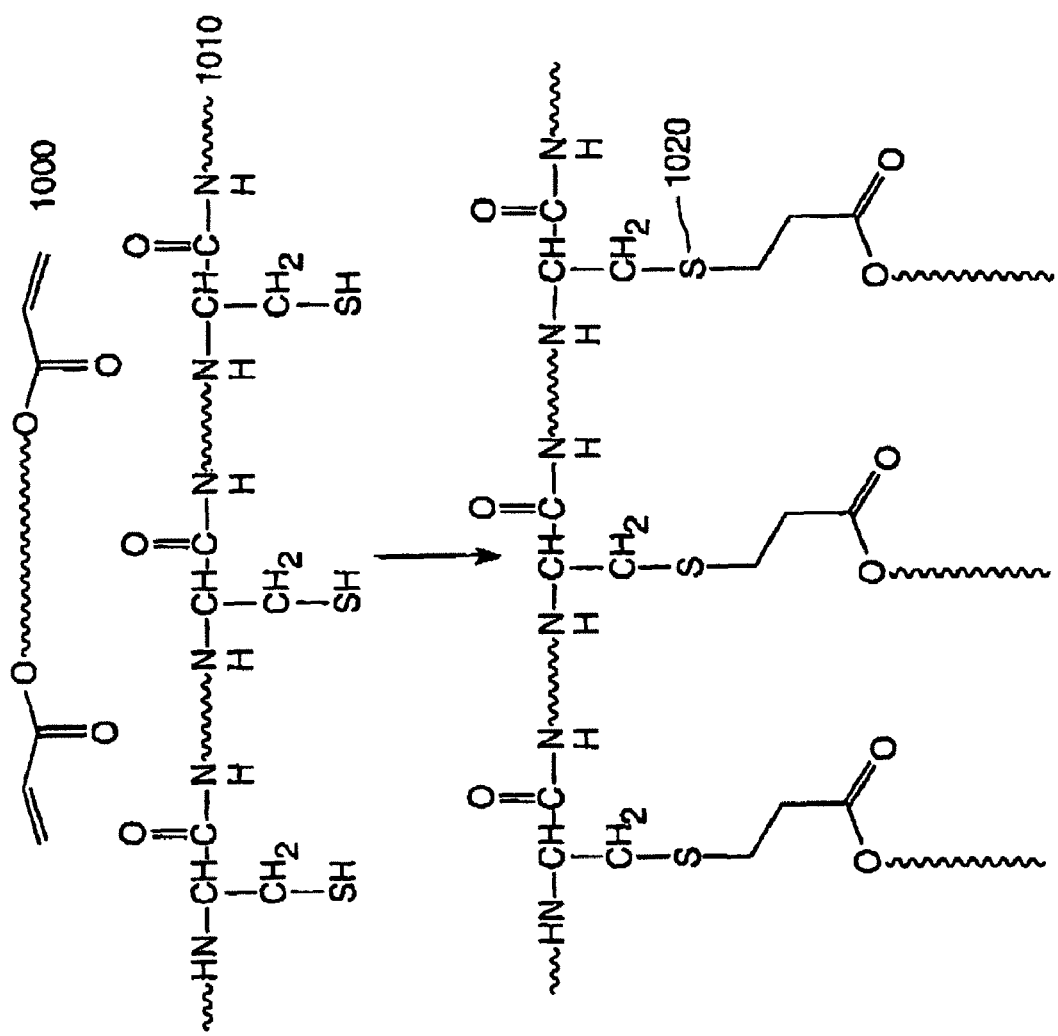
FIG. 10 illustrates an ester bond formed by at least two of the components of embodiments illustrated in FIG. 7 and FIG. 8.

FIG. 10 illustrates in molecular form the ester bond formed between the second component 1000 and the third component 1010 of a multi-component composition of FIG. 6. This bond 1020 is necessary for delaying the degradation of the scaffolding and release of the active agents within the microparticles. This bond tends to resist degradation for approximately 2 months.

D. Swellable Agent Systems for Reinforcement

Figure 11A:
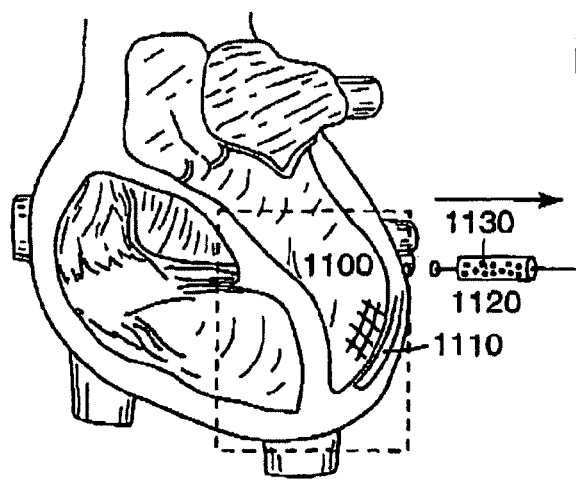
FIGS. 11A-11F illustrates introduction of structural reinforcement in the form of swellable microparticles to an infarct zone.
Figure 11B:
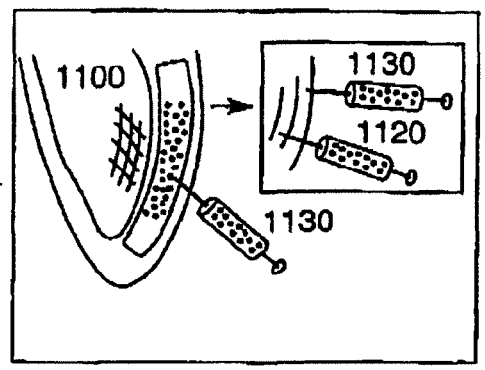
Figure 11C:
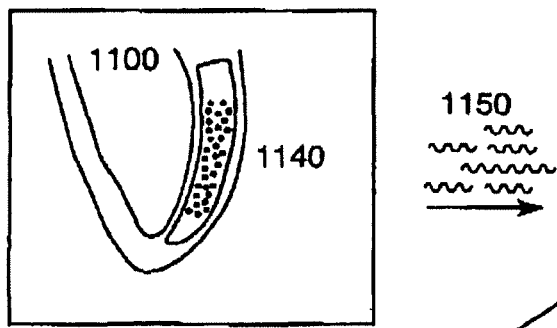
Figure 11D:
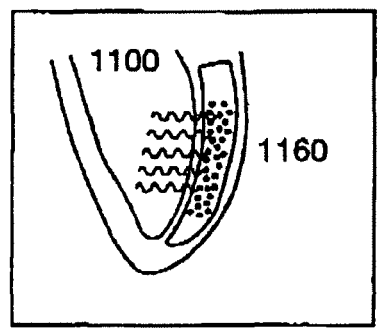

FIGS. 11A-11F illustrates the introduction of a swellable non-biologic material to structurally reinforce and/or bulk the infarct region. FIG. 11A illustrates the introduction of microparticles 1130 to infarct region 1110. Microparticles 1130 are shown accumulated in a mass at the site of the left ventricle 1100 within the infarct zone. One method for introduction of the microparticles 1120 is percutaneously with the use of a catheter 1130. A distal end of the catheter is advanced to the infarct region 1110 and the microparticles 1130 are released. The microparticles become lodged in the infarct tissue 1140. FIG. 11B illustrates microparticles 1130 acquiring the necessary surrounding fluid 1150 to swell 1160/1170. One embodiment includes the use of microparticle beads capable of fluid uptake in the infarct region to structurally reinforce the region. The particles will range in size from approximately 5 to approximately 10 microns. The microparticles will be less than 10 microns so that the completely swollen particle becomes lodged in the site treated infarct region 1180 but is not too large to become an obstruction in the area. In addition, the swollen microparticles provide mechanical strength and thickness to the damaged area by replacing the dead and degraded myocardial cells.

1. Agents a. Hydrogels Spheres

Examples of materials which can be used to form swellable hydrogel spheres are cross-linked poly(acrylamide) or cross-linked PVP. The monomeric form of these products will contain di-functional monomers such as di-vinyl benzene, ethylene glycol dimethylacrylate or 2,2-bis(acrylamide) acetic acid. These agents form a cross-linked network that is resistant to dissolution in aqueous systems.

b. Commercial Products

Figure 11E:
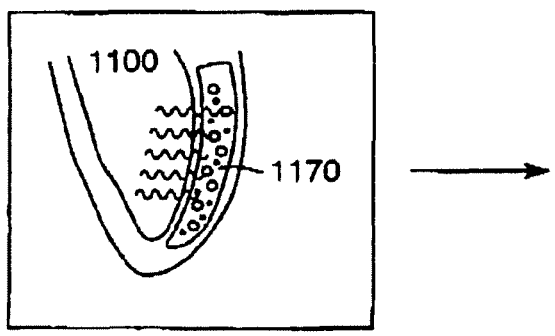
Figure 11F:
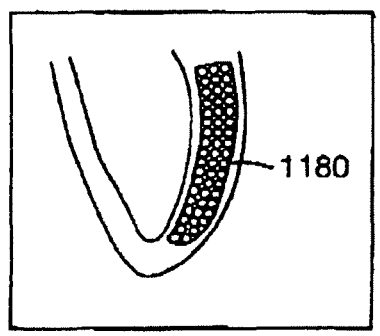

Several commercial products are available that may be used such as microparticles obtained from A.P. Pharma or Biosphere Medical. These microparticles resist non-specific protein absorption and have biostable backbone linkages. These microparticles are not bioerodable or bioabsorbable. FIG. 11E illustrates the microparticles dispersed in the infarct region taking up the surrounding fluid and swelling until they become lodged in the region (FIG. 11F).

E. Structural Reinforcement Compositions and Materials

Figure 12:
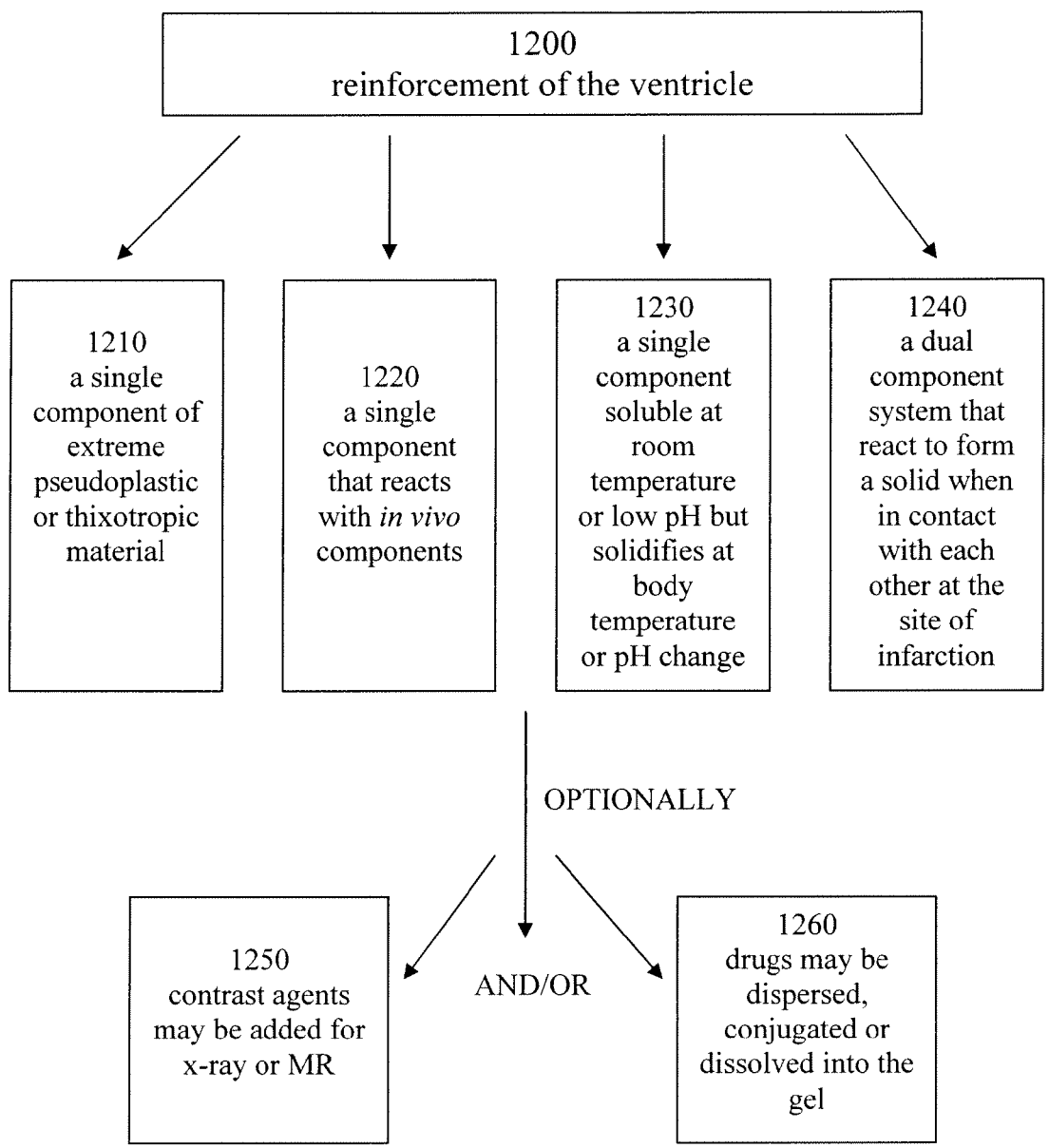
FIG. 12 illustrates a flowchart of several possible structural reinforcing agents that may be introduced to an infarct region.

FIG. 12 illustrates reinforcement of the ventricle (block 1200) by various single component embodiments. Restraining the infarct zone by suturing an epicardial polymer mesh bas been previously demonstrated. See Kelley, S. T., et al., *Restraining Infarct Expansion Preserves Left Ventricular Geometry and Function After Acute Anteroapical Infarction*, Circ., 1999, pp. 135-142, 99. Due to the nature of this technique, suturing the mesh directly into the tissue was necessary. This may cause further damage because the technique requires invasive surgery. In addition, the polymer mesh does not degrade over time and this may also be a problem. On the other hand, by injecting a reinforcing agent directly into the affected area by minimally invasive procedures, an intrusive suturing protocol can be avoided. However, in some embodiments, the solution may alternatively be injected in the infarct zone during an open chest procedure. In one embodiment, the introduction of the reinforcing solution includes sub-xiphoid and percutaneous procedures as well as retrograde venous perfusion. In another embodiment, the mode of introduction of the reinforcing solution by percutaneous injection may be performed by an intra-ventricular catheter or a transvascular needle catheter.

1. Single Component Systems

FIG. 12 illustrates embodiments of the reinforcement of the left ventricle post-MI (block 1200) by application of a single component bioscaffolding system. "Single component bioscaffolding" in the context of this application means that the platform used as the bioscaffolding is comprised of a single component or does not require cross-linking of at least two components to form the bioscaffolding when administered in vivo to an injury site of a patient. In one embodiment, a single component constitutes a single pseudoplastic or thixotropic material capable of forming a gel-like reinforcement to the infarct region wall (block 1210). Several examples of these materials exist. In one embodiment, the structural reinforcing agent includes one of the following: hyaluronic acid, bovine collagen, high-molecular weight ultra-pure poly(acrylamide), and polyvinylpyrrolidone.

In one embodiment, the single component for structural reinforcement comprises bovine collagen dispersed with PMMA poly(methyl methacrylate) beads. These beads may be manufactured under the trade name of ARTECOLL (Rofil Medical International, Breda, The Netherlands). PMMA is one of several cross-linked or highly insoluble microparticles. Recently, PMMA has been used in bone replacement of the jaw and hip. In addition, PMMA has been used for artificial eye lenses, pacemakers and dentures. ARTECOLL™ has principally been used in filling folds and wrinkles of the face, augmenting lips, adjusting an irregular nose.

Possibly one of the most important features of the insoluble microparticles is the surface of the microparticles must be smooth to induce collagen deposition. A rough surface promotes macrophage activity while discouraging collagen deposition. The methods incorporate the use of smooth surface particles. The components may act as a substrate for endogenous collagen deposition. As the reinforcing gel degrades, the highly stable and smooth microparticles may be exposed to the fibroblast cell population occupying the site. This triggers the production of collagen to replace the decomposing gel. Therefore, the infarct zone may be reinforced by the collagen replacement of the temporary gel. In one embodiment, the dispersing material includes one of the following: PMMA, poly(methyl methacrylate-co-butyl methacrylate) P(MMA-co BMA), carbon microparticles (DU-RASPHERET™), polystyrene, cross-linked acrylic hydrogels and PLGA. In another embodiment, the cross-linked acrylic hydrogel may include the following 2-hydroxyethyl methacrylate (HEMA), acrylic acid (AA), acrylamido-methyl-propane sulfonate (AMPS), acrylamide, N,N-dimethyl acrylamide, diacetone acrylamide, styrene sulfonate, and di- or tri-functional monomers. The di or tri-functional monomers may be EGDMA (ethylene glycol dimethacrylate) and DVB (di-vinyl benzene). In addition, the use of highly crystalline (and hydrolysis resistant) PLGA microparticles may outlast the carrier gel and also provide a useful substrate for collagen deposition.

Another single component system may be hyaluronic acid dissolved in sodium salt in water. Commercial forms of hyaluronic acid are available as an injectable visco-elastic (HEALON™, HEALON5™) or dermal augmentation crosslinked gel (RESTYLANE™). Hyaluronic acid hydrogel has also been used in the past for control of delivery of therapeutic agents in wound sites. Luo, Y. et al. *Cross-linked hyaluronic acid hydrogel films: new biomaterials for drug delivery*, J. of Controlled Release (2000) 69:169-184. Other possible single introduced components include bovine collagen (ZYDERM™ or ZYPLAST™), another dermal augmentation gel developed by Collagen Corp. The high molecular weight, ultrapure poly(acrylamide) in water may be FORMACRYL™ or BIOFORM™ other dermal augmentation gels. The bovine collagen may be dispersed by the PMMA product ARTECOLL™. ARTECOLL™ is best known for its success as a biocompatible dermal augmentation gel for reconstruction. RESOPLAST™ (Rofil Medical International, Breda, The Netherlands) may also be used as a single component gel.

In some embodiments, a single component bioscaffolding may be used to increase cytocompatibility and retention of cells (endogenous or exogenous) at an injury site. The single component hydrogel may be admixed with other diluting components, such as plasma or plasma products, buffers, or the like. Alternatively (or in addition to), the single component hydrogel may be blended, composited, or covalently grafted and/or linked with another (but different) synthetic or natural hydrogels such as poly(ethylene glycol), poly(vinyl alcohol), collagen, gelatin, chitosan, alginate, aloe/pectin, cellulose, silk-elastin, poly(N-isopropylacrylamide) (polyNIPAAM), or any combination thereof. In one embodiment, hyaluronan or a salt thereof may be used as the bioscaffolding platform. A one-component bioscaffolding system eliminates the necessity to achieve rapid and reproducible mixing at the needle tip prior to delivery as compared to a multi-component bioscaffolding system, e.g., a two-component system, which typically requires crosslinking. Additionally, a one-component bioscaffolding system only requires, in most cases, a single lumen delivery device which simplifies the application of such bioscaffolding to the injury site.

In one embodiment, a single component bioscaffolding platform includes hyaluronic acid or a salt thereof (hereinafter, referred to as "HA" or "NaHA") in a buffer or saline solution that may or may not contain plasma. Although previous experiments have shown that non-functionalized bioscaffoldings or bioscaffoldings seeded with stem cells provide angiogenesis at a fairly slow rate due to lack of cell-binding sites, it is anticipated that the embodiments disclosed herein will provide therapeutically useful results. For example, it is anticipated that plasma or a plasma product admixed with a non-functionalized bioscaffolding platform such as hyaluronic acid will provide additional cytokine signaling for the resulting bioscaffolding to effectuate angiogenesis or regenerative tissue growth. Referring to the single component bioscaffolding platform, the buffer should be capable of the maintenance of mammalian cells and may be, for example, phosphate buffered saline such as Dulbecco's phosphate buffered saline (DPBS). The plasma may be freshly harvested plasma from a mammalian source, refrigerated plasma, platelet-enriched plasma, fresh frozen plasma or frozen plasma, or dried plasma which may be reconstituted (hereinafter, collectively referred to as "plasma"). At least one advantage in having plasma admixed with the hyaluronic acid or salt thereof is that it is a natural constituent in the body, and, therefore, is anticipated to mitigate adverse reactions to the application (infusion or injection) of the single component bioscaffolding to an injury site, such as a strong immunogenic response.

The single component bioscaffolding also contains at least one cell type. In some embodiments, the cell type is either an embryonic or adult stem cell and may additionally be either autologous or non-autologous. Examples of such stem cells include, but are not limited to, localized cardiac progenitor cells, cardiac stem cells, mesenchymal stem cells, bone marrow derived mononuclear cells, adipose-derived stem cells, embryonic stem cells, umbilical cord blood derived stem cells, and skeletal myoblasts. An advantage of using stem cells is that they have the capability to differentiate into specialized cells or can serve as growth factor depots in a paracrine manner. For example, if stem cells are applied to a heart region, it is anticipated that they will differentiate into cardiomyocytes or provide sufficient supply of angiogenic and pro-survival cytokines. Other cell types include smooth muscle cells, fibroblasts and endothelial cells. The number of cells required in order to effectuate a therapeutic response should be in a range from about 0.5 million to about 100 million, preferably 10-50 million.

Properties of the hyaluronic acid or salt thereof may be controlled to minimize embolic risk, maximize injectability, cytocompatibility, biocompatibility, and to improve cell retention and overall cardiac function upon administration to an injury site. For example, properties such as the molecular weight, source, purity, viscosity and concentration of HA may all be controlled and/or optimized as necessary. For example, the source of HA may be derived from rooster combs and have an average molecular weight of between 1.5 million Daltons and 5 million Daltons. Alternatively, source of HA may be from a fermentation process. Additionally, the HA solution may have a concentration of between about 2.5 mg/mL to 30 mg/mL. It is anticipated that the single component bioscaffolding system as described will function to increase cell retention by preventing the initial mechanical loss of cells due to heart pumping in part due to the high viscosity of HA and its shear thinning characteristic. Also, since HA is a cytocompatible material, it should not generate significant inflammation in vivo and should allow for sufficient cell migration thus making it a preferable platform for a bioscaffolding in an infarct region. An additional advantage is its decreased embolic risk due to its quick dilution or dispersion upon accidental injection into the bloodstream.

In one embodiment, the single component bioscaffolding includes a cell suspension in a sodium hyaluronate solution at a concentration range of between 10 mg/mL and 23 mg/mL prior to the addition of the cell suspension wherein the NaHA has a weight average molecular weight of at least 4 million Daltons and the initial solution has a zero shear viscosity of between 300,000 millipascal second (mPa-s) and 7,000,000 mPa-s at rest, preferably 3,000,000 (mPa-s) and 7,000,000 mPa-s at rest. "Shear viscosity" of a system measures its resistance to flow. Illustratively, a simple flow field can be established in a system by placing it between two plates and then pulling the plates apart in opposite directions. Such a force is called a shear force, and the rate at which the plates are pulled apart is the shear rate. "Zero shear velocity" refers to the viscosity of a solution at rest. Shear viscosity is an important factor in the ability of a bioscaffolding platform to remain at an injury site. The osmolality of the resulting cell suspension may be near physiological osmolality, i.e., between about 280 Osmol/kg to about 325 Osmol/kg.

In another embodiment, a single component bioscaffolding solution including cells suspended in a NaHA solution with a weight average molecular weight of 4 million Daltons, a concentration of 23 mg/mL (prior to addition of the cell suspension), and a shear viscosity of 7,000,000 mPa-s (at rest) behaves as a cohesive agent at low shear and a dispersive agent at high shear which allows for greater cell protection at an injury site. In a specific embodiment, 23 mg/mL of NaHA may be combined with 8.5 mg sodium chloride, 0.28 mg disodium hydrogen phosphate dehydrate ($Na_2HPO_4$) and 0.04 mg sodium dihydrogen phosphate monophosphate ($NaH_2PO_4$) and combined with water in a container (e.g., syringe) to bring the total volume to 600 μL. This combination is commercially known as HEALON5™. Applicants have discovered that single component bioscaffolding systems, specifically HA and/or NaHA solutions, should have sufficiently high shear viscosity for adequate cell retention. In one embodiment, this shear viscosity range is between 3,000,000 mPa-s and 7,000,000 mPa-s (at rest). Applicants have discovered that HA and/or NaHA grades which are lower in shear viscosity than this specified range do not possess high enough shear viscosity to remain at the injury site and, in some instances, would migrate along the path of least resistance resulting in, for example, back-up into a needle lumen or injection track (in the case of administration by injection) or into the nearest blood vessel adjacent the injury site.

In some embodiments, the single component bioscaffolding system may be commercially provided in the form of a kit. In one embodiment, a kit may include three containers such as, for example, vials or syringes. A first vial (or syringe) may contain HA or NaHA in phosphate buffered saline solution and an optional second vial (or syringe) may contain plasma. The ratio of HA or NaHA in buffer to plasma may be from 95:5 to 5:95, depending on the particular application desired at the injury site. A third vial (or syringe) may contain at least one cell type suspension which has been previously frozen at least −80° C. or frozen in liquid nitrogen, wherein the cell type is of the type and in an amount as specified previously. In an alternative embodiment, a kit may include two vials and/or syringes. The first vial may contain HA or NaHA in buffer in addition to at least one cell type suspension. The second vial may contain plasma. As discussed previously, the use of PBS assists in the maintenance of mammalian cells and so it is anticipated that the cells within the solution will have a certain shelf-life before being commercially sold. In any embodiment disclosed, the type and properties of the HA or NaHA and of the cells will be within the types and ranges specified previously. Also, in any embodiment disclosed, it is anticipated that at least one container will be a syringe with a syringe barrel for ease of admixing the contents of the second container and optional third container. In this manner, the syringe may be fluidly connected to a catheter system for subcutaneous delivery, or, alternatively, delivery via an open chest procedure.

In some embodiments, a single component bioscaffolding system can be manufactured to provide a commercially-available kit for treatment of a post-myocardial infarct region or compromised cardiac tissue caused by ischemic or chronic heart failure. In one embodiment, a highly viscous solution with HA or NaHA (e.g., HEALON5™) in solution is mixed with a low viscous cell suspension. The type and properties of the cells will be within the types and ranges specified previously. Volume ratios of HEALON5™ to cell suspension include, but are not limited to 1:1, 2:3, or 2:3. To aid in mixing, methods such as syringe-to-syringe mixing (via luer or other connectors), paddle or stir mixing, centrifugation, vacuum mixing, static laminar flow helical mixing, or any combination thereof may be used. In one embodiment, the highly viscous HEALON5™ may be heated to slightly above physiological temperature to initially decrease the zero shear viscosity of the highly viscous solution. This, however, should be highly controlled to prevent cell lysis when the highly viscous solution is mixed with the low viscous cell solution. Mixing methods may be optimized for uniform mixing and maximum cell viability. Air bubbles generated during mixing should be substantially minimized and/or eliminated by employing methods such as: passing the mixture against a nanoporous (such as 20 nm pore size) hydrophobic filter; mixing within a vacuum; applying vacuum after mixing; centrifuging after mixing; or any combination thereof. The resultant mixture may be provided in at least one container as part of a commercially-available kit. In any embodiment disclosed, it is anticipated that at least one container will be a syringe with a syringe barrel for ease of admixing the contents of an optional additional container(s). In this manner, the syringe may be fluidly connected to a catheter system for subcutaneous delivery, or, alternatively, delivery via an open chest procedure.

In another embodiment, at least one cell type may be added to dry or lyophilized HEALON5™ powder and reconstituted with buffer. The resultant mixture may then be frozen in liquid nitrogen or at least −80° C. until ready for in vivo application. HEALON5™ may act as a cryoprotective medium for cells to minimize cell damage during freezing and thawing. The type and properties of the cells will be within the types and ranges specified previously. The resultant mixture may be provided in at least one container as part of a commercially-available kit. In any embodiment disclosed, it is anticipated that at least one container will be a syringe with a syringe barrel for ease of admixing the contents of an optional additional container(s). In this manner, the syringe may be fluidly connected to a catheter system for subcutaneous delivery, or, alternatively, delivery via an open chest procedure.

In the embodiments described, the bioscaffolding is formed in or on a treatment site by delivery of the single component bioscaffolding system thereto by a delivery system. The delivery system may be, for example, a syringe (e.g., for an open chest procedure), or, alternatively, a catheter system (e.g., for a subcutaneous procedure), such as those described in commonly-owned, U.S. Pat. No. 6,692,466 titled "Local Drug Delivery Catheter with Retractable Needle," by Chow et al. and U.S. Pat. No. 7,273,469 titled "Modified Needle Catheter for Directional Orientation Delivery" by Chan, et al. In one embodiment, a single lumen delivery system, such as an echo-guided catheter system with a needle gauge of 27G or greater, may be used. One of ordinary skill in the art will appreciate that other guided catheter systems may be used. A treatment site may include, but is not limited to, a post-myocardial infarction site, a chronic heart failure tissue site, vulnerable plaque within a diseased arterial vessel, or a cancer site.

In another embodiment, an endogenous compound-reacting single component system injected into the infarct region (block 1220) is illustrated. This example utilizes the introduction of a single component that forms a gel after reacting with an endogenous component. One such component may be tropoelastin (discussed previously). Elastin is the insoluble, elastic protein of high tensile strength found in connective tissue of the large arteries, trachea, bronchi and ligaments. Rarely seen endogenously as tropoelastin (the uncross-linked form), it rapidly cross-links to lysine residues in a process of oxidative de-amination by the enzyme lysyl oxidase when introduced in vivo. As stated previously, tropoelastin is available commercially as a recombinant bacterial product. When heated in water tropoelastin forms a coacervate and this may be injected into the infarct region where lysyl oxidase induces lysine cross-linking by the oxidative de-amination process. In one embodiment, tropoelastin may be introduced to the infarct region. In another embodiment, tropoelastin may be introduced to the infarct region after the introduction of the highly insoluble microparticles described above. Another reactive single-component may be cyanoacrylate adhesive. This is a widely used plastics binding agent. In one embodiment the cyanoacrylate may be octyl cyanoacrylate. The octyl cyanoacrylate may be the manufactured product called DERMABOND™ (Johnson and Johnson). This product was recently approved for use as a tissue adhesive for wound closure. Octyl cyanoacrylate may be introduced to the infarct region as a liquid. Once it contacts the infarct region, it solidifies due to its exposure to moisture. In another embodiment, the octyl cyanoacrylate may be introduced to the infarct region after the introduction of the highly insoluble, stable microparticles described above.

In another embodiment, a temperature-sensitive single component system injected into the infarct region (block 1230) is illustrated. One example of this type of component is a component that may be a liquid at room temperature, and, once exposed to a temperature approximately equal to body temperature, the component gels. A more specific component includes introducing block co-polymers of silk protein-like sub units and elastin-like sub units. An example of the block co-polymer synthetic protein may be ProLastin (PPTI, Protein Polymer Technologies). These components gel due to non-covalent interactions (hydrogen bonding and crystallization of silk-like subunits) at elevated temperatures for example approximately equal to body temperature. With these components, no lysine residues are present, so cross-linking due to endogenous lysyl oxidase does not occur. The formation of the gel via a change in temperature may be adjusted using additives. These additives include but are not limited to sodium chloride, diethylene glycol dimethyl ether (diglyme), 2-methoxyethyl ether, bis(2-methoxy ethyl ether), and ethanol.

Many thermal reversible materials may be used for reinforcement of the myocardial tissue. Generally, thermal reversible components at temperatures of approximately 37 degrees Celsius and below are liquid or soft gel. When the temperature shifts to 37 degrees Celsius or above, the thermal reversible components tend to harden. In one embodiment, the temperature sensitive structurally reinforcing component may be triblock poly(lactide-co-glycolide)-polyethylene glycol copolymer. This is commercially available (REGEL™ Macromed, Utah).

In another embodiment, the temperature sensitive structurally reinforcing component may include poly (N-isopropylacrylamide) and copolymers of polyacrylic acid and poly(N-isopropylacrylamide). Another temperature sensitive structurally reinforcing component commercially available is PLURONICS™ (aqueous solutions of PEO-PPO-PEO (poly (ethylene oxide)-poly(propylene oxide)-poly(ethylene oxide) triblock copolymers) (BASF, N.J.). See Huang, K. et al. "Synthesis and Characterization of Self-Assembling Block copolymers Containing Bioadhesive End Groups" Biomacromolecules 2002, 3, 397-406. Another embodiment includes combining two or more of the single components in order to structurally reinforce the infarct region. For example, silk-elastin, collagen and laminin may be used as a one-part system. The silk-elastin would likely form in situ cross-links due to the silk blocks.

In another embodiment, a reactive single component system includes a component that is pH sensitive (block 1230). The component remains in a liquid state if it is sufficiently protonated preventing gelation. In another embodiment, the component is initially maintained at a low pH for example pH 3.0 and later introduced to the treatment area which results in gelation of the component due to the physiological pH of the environment. One example of this is discussed in Example 3. Several possible cationic agents may be, but are not limited to, one of the following cationic agents that remain protonated at low pH: poly(allyl amine), DEAE-dextran, ethoxylated poly (ethylenimine), and poly(L-lysine). Other examples may be one of, but not limited to, the following anionic agents: dextran sulfate, carboxymethyl dextran, carboxymethylcellulose, polystyrene sulfonate and chondroitin sulfate.

Additionally, any of these microparticle components may be accompanied by one or more contrast agent (block 1250) and/or suitable agent(s) (block 1260) for treatment of the region. The contrast agent or treatment agent may be conjugated to or dissolved into the structural component prior to introduction to the infarct area. The agents that may accompany the reinforcing component(s) may include, but are not limited to, angiogenic agents, angiotensin-converting enzyme (ACE) inhibitors, angiotensin receptor blockers, sarcoplasmic reticulum calcium pump increasing agents (SRCA), phospholamban inhibitors and anti-apoptotic drugs. These agents may be in the form of small molecules, peptides, proteins or gene products. The small molecules may be optionally conjugated to a component of the solution, dispersed in solution, or dissolved in solution to improve the adhesion of the reinforcing components to the tissue. One embodiment is to conjugate a peptide with a conserved region that mediates adhesion processes. A conserved region of a peptide may be a sequence of amino acids having a special function of identification that has been conserved in a protein family over time. Another embodiment includes the use of a specific peptide conjugate with a conserved RGD motif in the presence of the reinforcing component. In further embodiments, the RGD motif peptide may include the following: von Willebrand factor, osteopontin, fibronectin, fibrinogen, vitronectin, laminin and collagen. One embodiment seeks to minimize thinning during remodeling of the infarct region. Thus, bulking and reinforcing the infarct region post-MI may preserve the geometry of the ventricle.

Any one or more catheters may be used to deliver the any one or multiple components of the embodiments to the infarct region area. Several catheters have been designed in order to precisely deliver agents to a damaged region within the heart for example an infarct region. Several of these catheters have been described. See U.S. Pat. Nos. 6,309,370; 6,432,119; 6,485,481. The delivery device may include an apparatus for intra-cardiac drug administration, including a sensor for positioning within the heart, a delivery device to administer the desired agent and amount at the site of the position sensor.

2. Dual Component Systems

Figure 13:
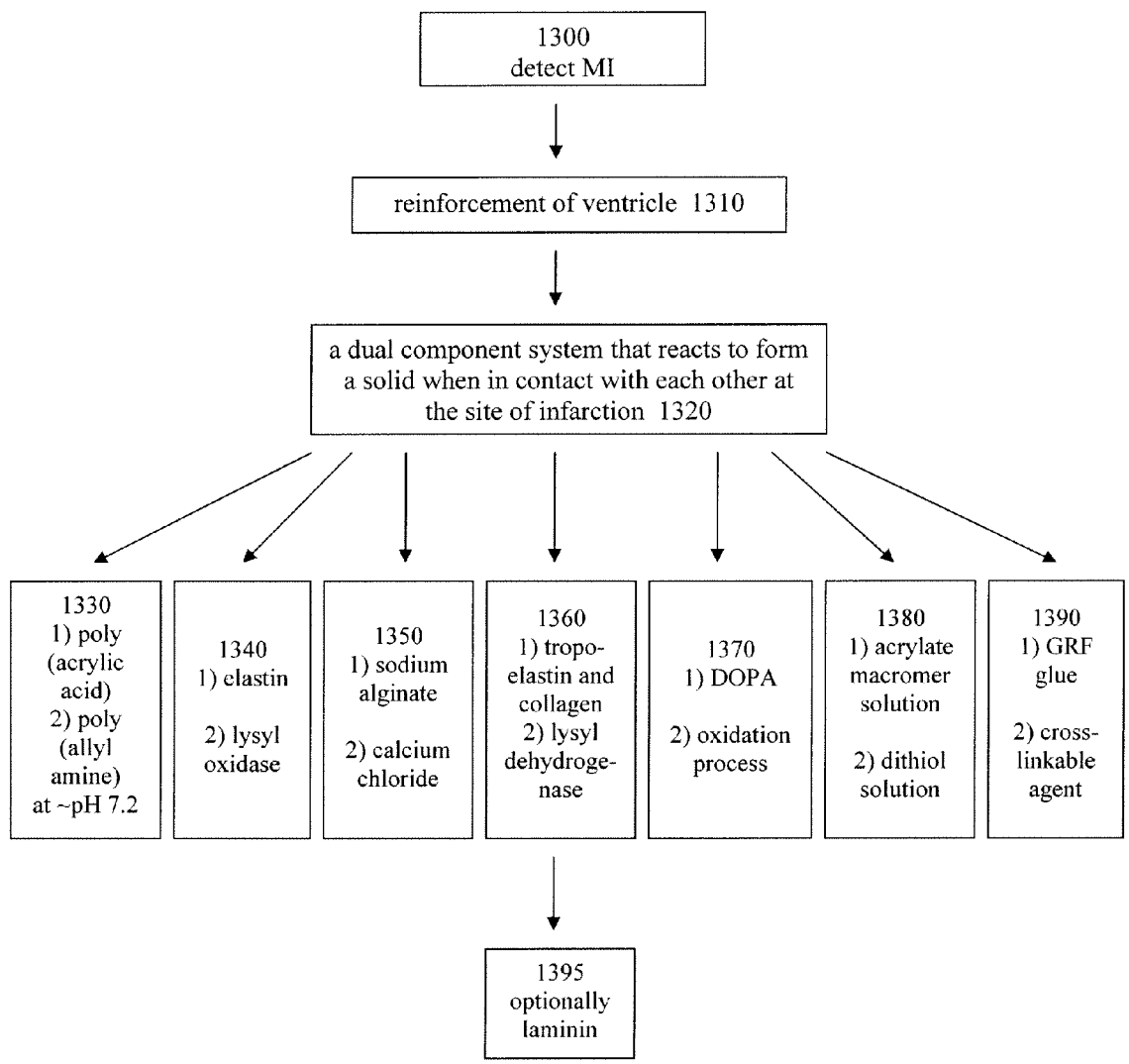
FIG. 13 illustrates an expansion of FIG. 12 disclosing examples of dual component systems.

FIG. 12 illustrates an alternative embodiment of a dual component system injected into the infarct region (block 1240). FIG. 13 illustrates embodiments of a dual component system to form a structurally reinforcing gel in the infarct region (block 1320). Initially, the infarct region is identified (block 1300) by imaging methods previously discussed. In one example, two components are combined at the infarct zone at around physiological pH (block 1330). Component one is a principally anionic solution and component two is principally a cationic solution at approximately physiological pH. When the two components are mixed together at the infarct zone, a gel forms rapidly and irreversibly. In one embodiment, a dual component system may comprise poly (acrylic acid) as a first component and poly(allyl amine) as a second component as illustrated in FIG. 13 (block 1330). In another embodiment, a dual component system may comprise poly (acrylic acid) as a first component and poly(allyl amine) as a second component that may be delivered by a catheter with dual injection lumens. Other dual component systems to form a structurally reinforcing gel in the infarct region may include elastin as a first component and lysyl oxidase as a second component (block 1340); sodium alginate as a first component and an aqueous solution of calcium chloride as a second component (block 1350), and tropoelastin and collagen as a first component and cross-linker lysyl dehydrogenase as a second component (block 1360). Laminin (block 1395) may be added to this combination later. The composition of each component will depend on the mechanical property of the final cross-linked system. Other substances that can replace the lysyl dehydrogenase or complement its cross-linking ability might be used such as glutaraldehyde, and/or photoactivatable crosslinkers, for example, blue dye used to cross-link. Additionally, these dual component systems may be combined with other individual system utilizing commercial products such as AVITENE™ (Microfibrillar Collagen Hemostat), SUGICEL™, (absorbable haemostat, Johnson & Johnson), GELFOAM™, FLO-SEAL™ (Baxter, matrix hemostatic sealant with a granular physical structure and thrombin), FOCAL SEAL™ (Focal, Inc.) or FIBRIN SEAL™ (FS). FLOSEAL™ is a gel constituting collagen-derived particles and topical thrombin capable of being injected. It has been approved for uses including vascular sealing. Several other possible cationic agents may be, but are not limited to, cationic agents which remain protonated at low pH: poly(allyl amine), DEAE-dextran, ethoxylated poly(ethylenimine), and poly(L-lysine). Other examples may be one of, but are not limited to, the following anionic agents: dextran sulfate, carboxymethyl dextran, carboxymethylcellulose, polystyrene sulfonate and chondroitin sulfate. In a preferred embodiment, the first component may be DEAF-dextran and the second component may be poly(styrenesulfonate).

FIG. 13 illustrates the use of another dual component system, DOPA (3,4-dihydroxyphenyl-L-alanine), a principle component responsible for muscle adhesive proteins, capable of forming a hydrogel in conducive conditions (block 1370). Specifically, a component known as star block DOPA-block-PEG undergoes cross-linking in situ forming the hydrogel after an oxidation process converts the DOPA to O-quinone. This process forms a stable in situ hydrogel. FIG. 13 1380 includes the use of an acrylate macromer solution and a dithiol solution injected into the infarct region for structural reinforcement (block 1380). These components when mixed at the infarct site undergo a cross-linking reaction leading to the formation of a hydrogel. A specific embodiment may comprise the use of PEG triacrylate as the first component and PEG thiol as the second component introduced to the infarct zone via a dual lumen needle system discussed previously. In FIG. 13, a glue-like component system may be employed. One embodiment may include the use of GRF glue that is made up of gelatin, resorcinol and formaldehyde (GRF) as a structurally reinforcing agent introduced to the infarct zone (block 1390). To accomplish this, a two-part system may be used to induce cross-linking upon admixture of the components at the infarct zone. In other embodiments, the following structurally reinforcing components may be added along with GRF: cross-linking agents such as poly(glutamic acid), poly (L-lysine) and water-soluble carbodimides (WSC).

Figure 14:
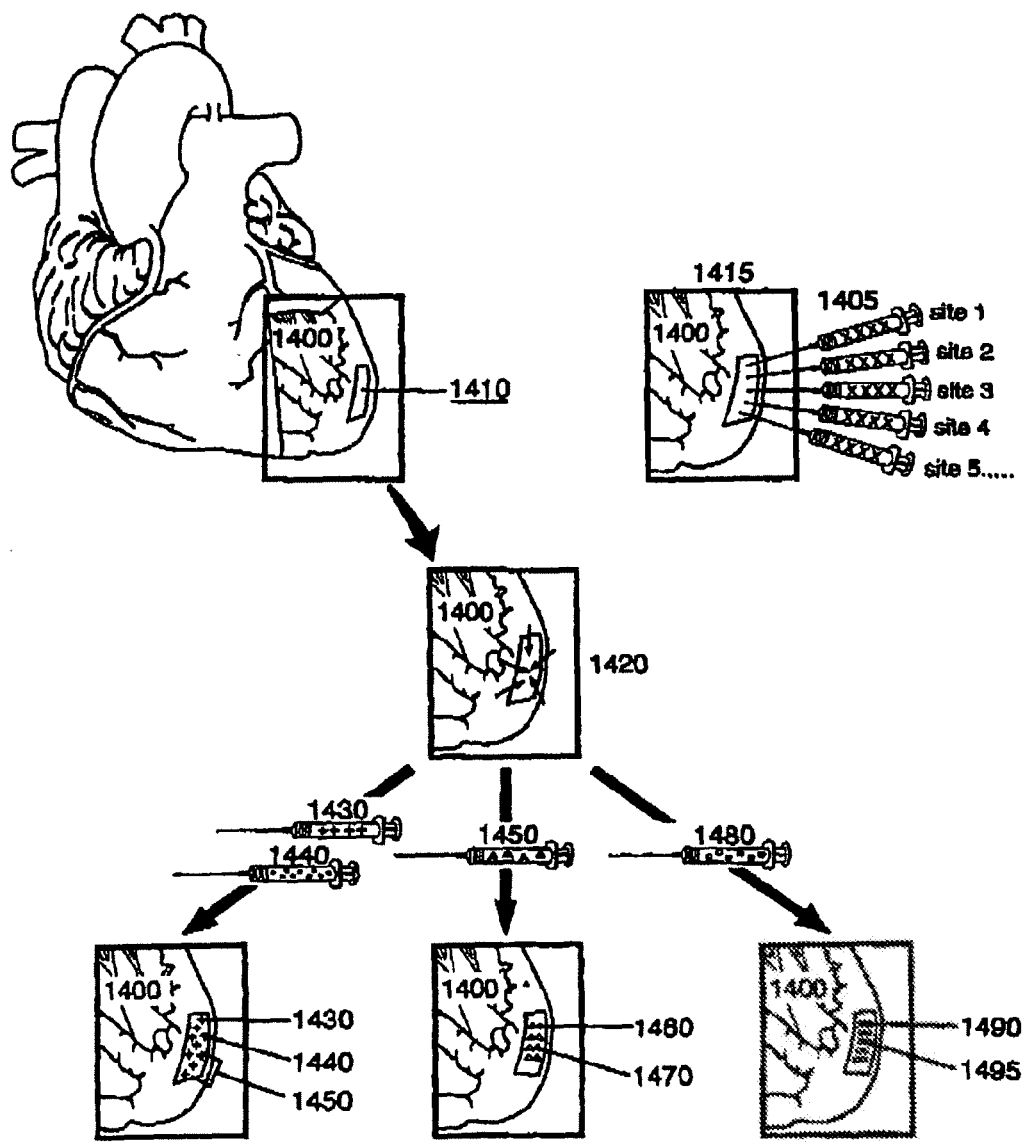
FIG. 14 illustrates introduction and action of the methods illustrated in the flowchart of FIG. 13 in an infarct region.

FIG. 14 illustrates the introduction and action of a single component or dual components to the infarct region for structural reinforcement. FIG. 14 illustrates the identification of the infarct region 1410 of the ventricle 1400 by methods previously described and subsequent multiple injection of the separate components to the site of damage 1420. In a dual component system, the two components 1430/1440 contact each other at the site and form reinforcing structural scaffold 1430/1440. These agents are introduced in final form and require no additional agents. FIG. 14 illustrates the addition of at least one agent 1430/1440/1450/1480 by multiple injections each at a different site 1405/1415 that requires an endogenous component or a temperature change 1460/1490 to convert to a structurally reinforcing form 1450/1470/1495. The structurally reinforcing agent(s) is localized to the infarct region via minimally invasive procedures discussed previously.

In addition, biocompatible viscosifiers, for example, type 1 gels may be added in combination with any of the single or multiple component systems illustrated. For example, hyaluronic acid or PVP may be used to increase the resistance of the active formula from natural degradation once introduced to the infarct zone. In one embodiment the viscosity of the treatment agent may be about 0-100 centipoise. In other embodiments, the viscosity of the treatment agent may be about 0-50 centipoise. In a preferred embodiment, the viscosity of the treatment agent may be about 25-40 centipoise. In a preferred embodiment, the viscosity of the treatment agent may be about 35 centipoise.

In one embodiment, any of the described agents may be introduced in one or more doses in a volume of about 1 µL to 1 mL. In another embodiment, any of the described agents may be introduced in one or more doses in a volume of about 1 µL to 300 µL. In another embodiment, any of the described agents may be introduced in one or more doses in a volume of about 1 µL to 100 µL. In a preferred embodiment, the any of the described agents may be introduced in one or more doses in a volume of about 1 µL to 50 µL. Intra-ventricular or intra-coronary routes may be required which would involve larger treatment volumes (for example about 2 mL to about 250 mL).

Biocompatible dyes may be added to any single or combination components of any of the described embodiments to trace the components in the infarct region in any procedure. Other dyes may be added for experimental purposes to trace the deposition of any agent for example in a rat heart. Some examples of these dyes include but are not limited to Sudan Red B, Fat Brown RR, Eosin Y and Toluidine blue.

In other embodiments, tissue adhesive components may also be added in combination with any of the single or dual component systems illustrated in FIG. 12, 13 or 14. For example, laminin-5, polyacrylic acid, chitosan and water-soluble chitosan may be used to increase the tissue retention of the active formulation. Laminin-5 is a basement membrane extracellular matrix macromolecule that provides an attachment substrate for both adhesion and migration in a wide variety of cell types, including epithelial cells, fibroblasts, neurons and leukocytes. Chitosan is the only natural positive ion polysaccharide obtained from deacetylated chitin. It possesses decomposability, good membrane forming state, biocompatibility, anti-fungal and anti-tumor function. Chitosan has excellent viscosity, compressibility and fluidity.

F. Single Components Suspended in a Delivery Medium

Figure 15:
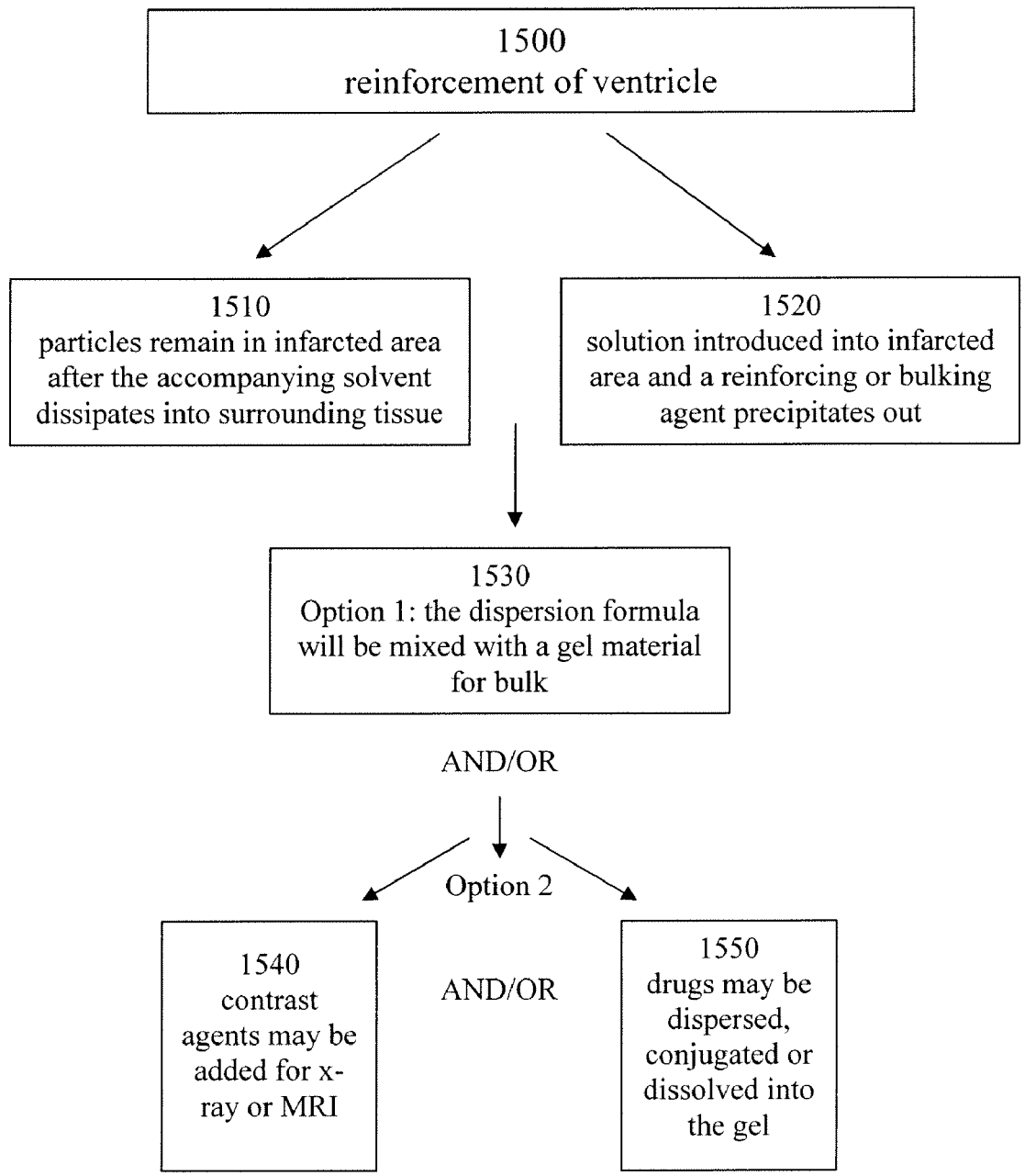
FIG. 15 illustrates two possible methods to structurally reinforce an infarct zone by bulking up a region.

FIG. 15 illustrates a flowchart describing other methods to prevent the remodeling and ultimate thinning of the infarct region. As with several of the previously discussed methods, these methods provide a bulking or structurally reinforcing agent to the infarct region. In FIG. 15, an agent comprising microparticles in solution (i.e., a dispersion) is introduced to the infarct region (block 1510) after identification of the infarct region as described previously. The microparticles may be a predetermined range of about 1 to about 200 microns. In one embodiment, the microparticles may be 20 microns or less. In a preferred embodiment, the microparticles may be 10 microns or less. The microparticle size delivered to an infarct region may be determined by the delivery method used. For example, an intra-ventricular catheter may be used to deliver particles up to 200 microns that may avoid the risk of an embolism. One suspending solution for the microparticles may be water. On the other hand, the suspending solution may also be a solvent, for example, dimethylsulfoxide (DMSO) or ethanol adjuvants. In one embodiment, a suspending solution along with the microparticles may be introduced as a dispersion to an infarct region and the microparticles remain in the region as the solution dissipates into the surrounding tissue. Thus, the microparticles provide a structurally reinforcing bulk to the region. This may result in reduction of stress to the post infarct myocardium. It may also serve as a substrate for additional site for collagen deposition. In one embodiment, the dispersion (detailed above) may be injected into the infarct zone during an open chest procedure via a minimally invasive procedure. In another embodiment, the minimally invasive procedure includes at least one of subxiphoid and percutaneously. In another embodiment, the percutaneous introduction into the infarct zone may include one of intra-ventricular needle, transvascular catheter and retrograde venous perfusion.

In another embodiment, the microparticles precipitate out of the solution In FIG. 15, an agent including microparticles in solution is introduced to the infarct region (block 1520). The microparticles may be a size of 0.1 to 200 microns. In a preferred embodiment, the microparticles are 10 microns or less. In one embodiment, the suspending solution along with the microparticles may be introduced to the infarct region and the microparticles precipitate out of the dispersion in the region. Thus, the microparticles provide a structurally reinforcing bulk to the region. This may result in reduction of stress to the post infarct myocardium. It may also serve as a substrate for additional site for collagen deposition. In one embodiment, the dispersion (detailed above) may be injected in to the infarct zone during an open chest procedure via a minimally invasive procedure. In one embodiment, the introduction of the reinforcing solution includes sub-xiphoid and percutaneous procedures as well as retrograde venous perfusion. In another embodiment, the mode of introduction of the reinforcing solution by percutaneous injection may be performed by an intra-ventricular catheter or a transvascular needle catheter.

Figure 16:
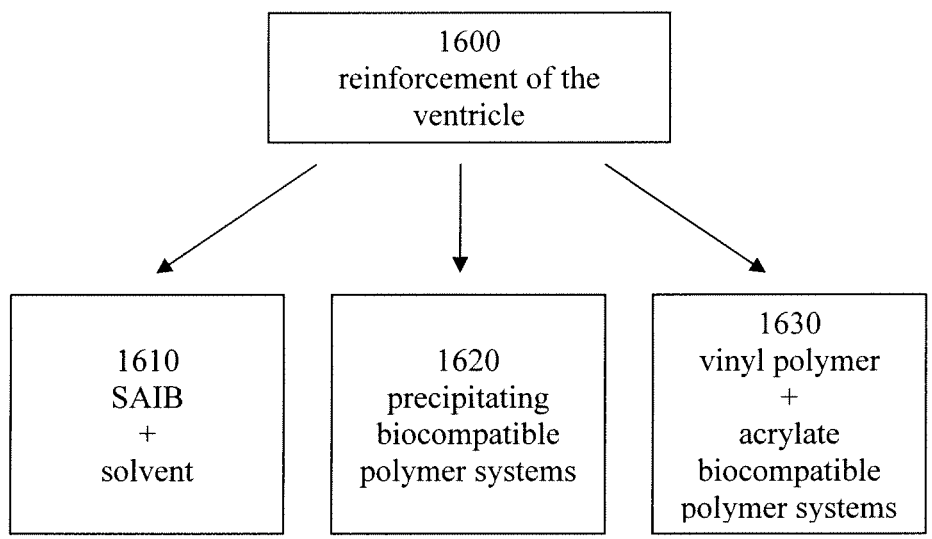
FIG. 16 illustrates examples of bulking agents that may structurally reinforce an infarct region.

Several examples of the microparticles described with reference to FIG. 15 are illustrated in FIG. 16. For example, FIG. 16 illustrates the viscous liquid sucrose acetate isobutyrate (SAIB) (block 1610). SAIB is water-insoluble and may be dissolved in a solvent or a combination of solvents such as, ethanol, dimethylsulfoxide, ethyl lactate, ethyl acetate, benzyl alcohol, triacetin, 2-pyrrolidone, N-methylpyrrolidone, propylene carbonate or glycofurol. These solvents decrease the viscosity of SAIB in order to facilitate the introduction of this agent through a needle or lumen. In one embodiment, SAIB may be introduced accompanied by a solvent to the infarct region and the solvent dissipates at the site leaving behind the viscous SAIB in the region.

Other biocompatible polymer systems may be introduced to an infarct zone (block 1620). Some of these agents are not only biocompatible but also substantially water-insoluble similar to SAIB. Solvents or mixtures of solvents may be used to dissolve the polymer in order to facilitate introduction to the infarct zone. In one embodiment, a biocompatible water-insoluble polymer may include the following consisting of poly(lactides), poly(glycolides), poly(caprolactones), poly (anhydrides), poly(alkylene oxates), poly(amides), poly(urethanes), poly(esteramides), poly(dioxanones), poly(hydroxyvalerates), poly(acetals), polyketals, poly(carbonates), poly(orthoesters), poly(phosphazenes), poly(hydroxybutyrates), poly(alkylene succinates), and poly(amino acids). Any one of these insoluble polymers may be dissolved in solvents, for example, diglyme, dimethyl isosorbide, N-methyl-2-pyrrolidone, 2-pyrrolidone, glycerol, propylene glycol, ethanol, tetraglycol, diethyl succinate, solketal, ethyl acetate, ethyl lactate, ethyl butyrate, dibutyl malonate, tributyl citrate, tri-n-hexyl acetylcitrate, diethyl glutarate, diethyl malonate, triethyl citrate, triacetin, tributyrin, diethyl carbonate, propylene carbonate acetone, methyl ethyl ketone, dimethyl sulfoxide dimethyl sulfone, tetrahydrofuran, caprolactam, N,N-diethyl-m-toluamide, 1-dodecylazacycloheptan-2-one, 1,3-dimethyl-3,4,5,6-tetrahydro-2(1H)-pyrimidinone and glycerol formal to form an injectable polymer solution. The dispersion may be introduced into the infarct region of the heart wherein the solvent may dissipate and the polymer may precipitate out of the dispersion to structurally reinforce the infarct regional wall. In one embodiment, the disclosed polymers may be used in any combination as co-polymers of two or more polymers introduced to the infarct region.

FIG. 16 illustrates a vinyl polymer and acrylate biocompatible polymer system (block 1630). Once injected into an infarct zone, the vinyl polymer/acrylate agent contacts water and the polymer precipitates thus reinforcing the surrounding tissue of the infarct region. In one embodiment, the vinyl polymer/acrylate agent includes the following such as polyvinyl butyral, PBMA-HEMA, PEMA-HEMA, PMMA-HEMA and other acrylate copolymers that dissolve in ethanol, acetone and I-PA. In another embodiment, the vinyl polymer/acrylate agent introduced to the infarct region may be EVAL™ that has a solid phase or melt phase forming process. EVAL™ Resins have a high crystalline structure. Thermoforming grades of EVAL™ resins have monoclinic crystalline structure while most polyolefins have either a hexagonal or orthorhombic type structure. This characteristic provides flexibility within its thermoforming capabilities. In another embodiment, the vinyl polymer/acrylate agent introduced to the infarct region may be BUTVAR™ (polyvinyl butyral). In one embodiment, the agent may be P(BMA co-MMA) (Aldrich Chem.) in diglyme. In another embodiment, the agent may be EVAL™, a co-polymer of ethylene and vinyl alcohol (EVAL Co. of America, Houston, Tex.) in dimethyl acetamide. In another embodiment, the polymer may be PLGA poly(lactide co-glycolide) (Birmingham Polymers, Birmingham, Ala.) in diglyme.

Other components may act as a substrate for endogenous collagen deposition and protect the precipitated or remaining microparticles described in FIG. 16 from erosion. As the reinforcing gel degrades, the highly stable and smooth microparticles may be exposed to the fibroblast cell population occupying the site. This triggers the production of collagen to replace the decomposing gel. Therefore, the infarct zone may be reinforced by the collagen replacement of the temporary gel. The dispersed material includes the following group of microparticle materials: PMMA, P(MMA-co BMA), carbon microparticles (DURASPHERE™), polystyrene, cross-linked acrylic hydrogels and PLGA. In another embodiment, the cross-linked acrylic hydrogel may include the following: HEMA, AA, AMPS, acrylamide, N,N-di-methyl acrylamide, diacetone acrylamide, styrene sulfonate, and di- or tri-functional monomers. The di- or tri-functional monomers may be EGDMA and DVB. Another example of durable microparticles includes pyrolytic carbon-coated microparticles. One example of pyrolytic carbon-coated microparticles was originally produced for urinary incontinence (Carbon Medical Technologies) and tris-acryl gelatin microparticles for use as embolization particles (Biosphere). In addition, the use of highly crystalline (and hydrolysis resistant) PLGA microparticles may outlast the carrier gel and also provide a useful substrate for collagen deposition.

One or more contrast agents (block 1540) and/or suitable treatment agent(s) (block 1550) may accompany the previously detailed components as a treatment of the infarct region. The contrast agent or treatment agent may be conjugated to or dissolved into the structural component prior to introduction to the infarct area. The contrast agents may be used for detection in X-ray or MR analysis. The agents that may accompany the reinforcing component(s) may include, but are not limited to, angiogenic agents, ACE inhibitors, angiotensin receptor blockers, SRCA pump (sarcoplasmic reticulum calcium pump) increasing agents, phospholamban inhibitors and anti-apoptotic drugs. These agents may be in the form of small molecules, peptides, proteins or gene products. The small molecules may be optionally conjugated to a component of the solution, dispersed in solution, or dissolved in solution to improve the adhesion of the reinforcing components to the tissue. One embodiment is to conjugate a peptide with a conserved region that mediates adhesion processes. Another embodiment includes the use of a specific peptide conjugate with a RGD motif in the presence of the reinforcing component. In further embodiments, the RGD motif peptide may include von Willebrand factor, osteopontin, fibronectin, fibrinogen, vitronectin, laminin and collagen.

In one embodiment, any of the described agents may be introduced in one or more doses in a volume of about 1 µL to 1 mL. In another embodiment, any of the described agents may be introduced in one or more doses in a volume of about 1 µL to 300 µL. In another embodiment, any of the described agents may be introduced in one or more doses in a volume of about 1 µL to 100 µL. In a preferred embodiment, the any of the described agents may be introduced in one or more doses in a volume of about 1 µL to 50 µL.

G. Collagen Cross-Linking Agents for Structural Reinforcement

Figure 17:
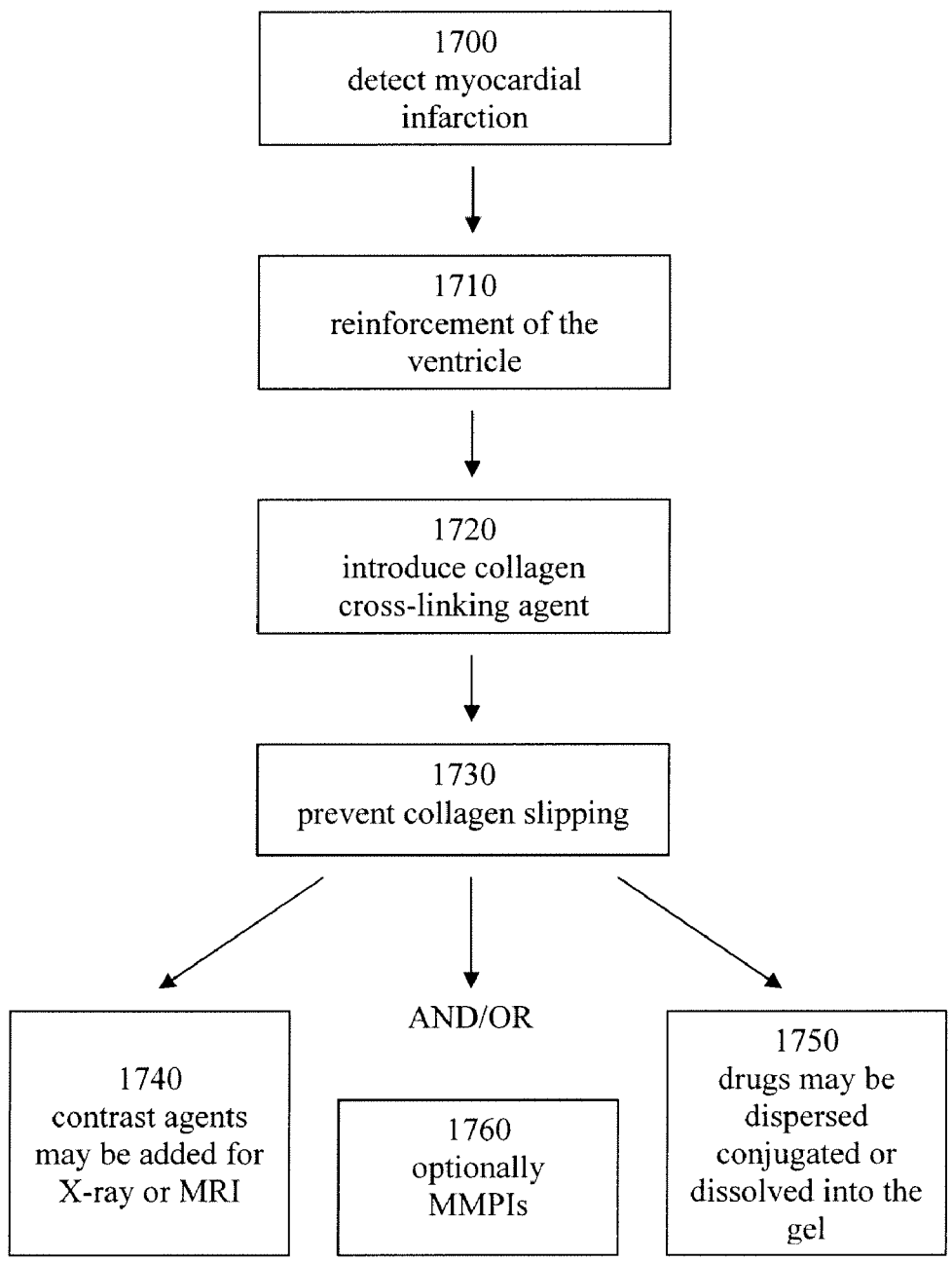
FIG. 17 illustrates stabilizing the collagen in an infarct zone by cross-linking.

FIG. 17 is a flowchart illustrating an alternative method to structurally reinforce the infarct region of the ventricle (block 1710). As previously mentioned, thinning is a key factor in the cascade of events following remodeling of the infarct region. One factor contributing to the thinning is collagen degradation by matrix metalloproteinases (MMPs) and collagen helix slippage due to hemodynamic stress. The collagen slippage generates infarct scar expansion that leads to additional remodeling and remote zone hypertrophy. Previous inventions to prevent collagen slippage include a suturing procedure. See Kelley, S. T., et al., *Restraining Infarct Expansion Preserves Left Ventricular Geometry and Function After Acute Anteroapical Infarction*, Circ., 1999, pp. 135-142, 99. This involves directly suturing a epicardial polymer mesh to the region. According to one embodiment, agents will be introduced to the region by a minimally invasive procedure to prevent collagen slippage. An agent or dispersion will be introduced in one embodiment by multiple injections to the infarct zone, then the agent will react with the collagen scar directly to cross-link it. This results in prevention of slippage and strength to the regional wall. In one embodiment, the dispersion (detailed above) may be injected in to the infarct zone during an open chest procedure via a minimally invasive procedure. In one embodiment, the introduction of the reinforcing solution includes sub-xiphoid and percutaneous procedures as well as retrograde venous perfusion. In another embodiment, the mode of introduction of the reinforcing solution by percutaneous injection may be performed by an intra-ventricular catheter or a transvascular needle catheter.

A contrast agent or treatment agent may be conjugated to or dissolved into the structural component prior to introduction to the infarct area, such as those described previously (block 1740).

Figure 18:
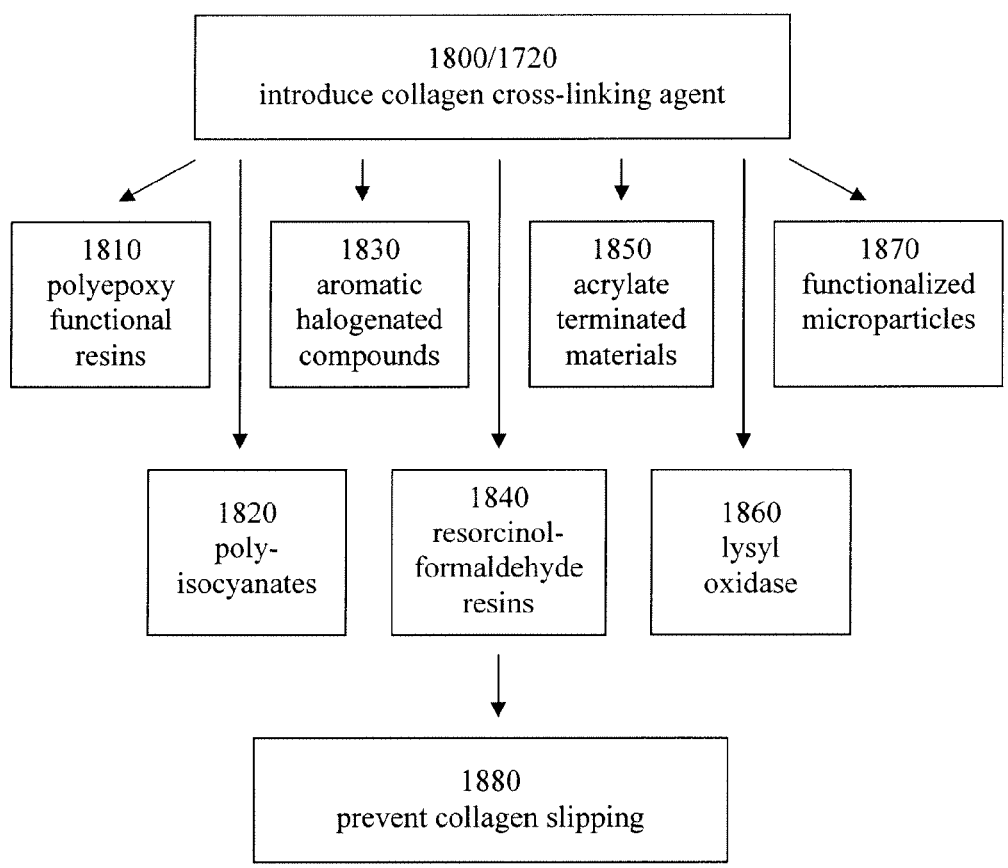
FIG. 18 illustrates various agents that may cross-link the collagen in an infarct region.

Several embodiments of cross-linking agents (block 1720) are illustrated in FIG. 18 to prevent collagen slippage (block 1730). The agent injected into the infarct region may be poly-functional (either hetero- or homo-polymer). Another important feature of the cross-linking agent is the ability of the agent to cross-link to the side groups of the amino acids of the collagen (type I and III). In one embodiment, the agent is soluble in a biocompatible water-miscible solvent that is capable of being drawn out of the dispersion by aqueous fluid present in the myocardium. This enables the cross-linking agent the ability to precipitate out into the infarct region minimizing migration of the cross-linking agent out of the area. In another embodiment, the biocompatible solvent used in the presence of the cross-linking agent may be the following: diglyme and dimethyl isosorbide. Collagen is made up of a large number of lysine and hydroxyproline residues that carry reactive side groups of primary amines and hydroxyl groups respectively. In the following examples, the cross-linking agents react with at least one of these side groups.

FIG. 18 is a flowchart illustrating embodiments of collagen cross-linking agents. In one embodiment, a poly(epoxy) functional resin may be introduced to the infarct region (block 1810). The poly(epoxy) functional resin may comprise the following: Bisphenol A epoxies (Shell 828), Epoxy-Novolak resins (Ciba 1138 and 1139, Dow 431), homopolymers of glycidyl methacrylate (GMA) or copolymers of GMA with other acrylates. In another embodiment, the poly(epoxy) functional resins may include a multifunctional epoxide. In another embodiment, the poly(epoxy) functional resins may include an acrylate. The later resins, multifunctional epoxides and acrylate, are based on a cubic silicone with eight epoxide or acrylate functionalities (silsesquioxanes). In another embodiment, the poly(epoxy)functional resins may include a tetra-functional epoxide silicone. In another embodiment, the poly(epoxy) functional resins may include di-functional epoxide silicone.

In another embodiment, poly(isocyanates) may be introduced to the infarct region (block 1820). Examples of poly(isocyanates) may include the following: the biuret of hexamethylene di-isocyanate and isocyanurate of hexamethylene di-isocyanate. Both of these products are manufactured commercially under the name DESMODUR N 100 and DESMODUR 3300 respectively (commercially available from Bayer). In another embodiment, aromatic halogenated compounds may be introduced to the infarct region (block 1830). An example of a halogen compound used to cross-link the collagen is 1,5-difluoro-2,4-dinitrobenzene (DFNB).

In another embodiment, poly(hydroxyl) aromatics (resorcinol groups) such as vegetable tannins may be introduced to the infarct region (block 1840). Solvent-soluble resorcinol-formaldehyde resins contain numerous resorcinol groups. A methylene bridge and/or an ether bridge connect the resorcinol groups. RESORCINOL™ is capable of cross-linking collagen but one problem is that it is corrosive and water miscible in its monomeric form. In one embodiment, the cross-linking agent to secure the collagen and structurally reinforce the infarct region may be a resorcinol-formaldehyde resin.

In another embodiment, agents that terminate in an acrylate group may be introduced to the infarct region (block 1850). These acrylate-terminating agents react with the primary amine groups of the collagen and form a stabilizing cross-link. Examples of an acrylate-terminating agent used to cross-link the collagen may include a water-insoluble agent such as urethane-acrylates and epoxy-acrylates. These compounds are commercially available (Cognis Corp, Ohio, U.S.A.). In another embodiment, lysyl oxidase may be introduced to the infarct region (block 1860). Lysyl oxidase may be use alone or in combination with other agents to cross-link the collagen for prevention of slippage (block 1880) and as a structurally reinforcing agent in the infarct region. Lysyl oxidase is an enzyme that oxidatively de-aminates lysine side groups and forms reactive aldehyde groups capable of forming strong cross-linking bonds with the collagen. In one embodiment, lysyl oxidase may be introduced to the infarct region to cross-link the existing collagen for prevention of slippage.

In another embodiment, functionalized microparticles may be introduced to the infarct region (block 1870). One example includes the use of surfactant free styrene latex particles in narrow size distributions that also contain the following functional surface groups such as chloromethyl, epoxy and aldehyde. The aldehyde surface groups may be tightly packed therefore borohydride reduction would not be necessary for a stable linkage. Chloromethyl groups react with primary and secondary amines thus forming a stable cross-link. Other possible functional reacting groups may include succinimidyl ester, benzotriazole carbonate and p-nitrophenyl carbonate. In one embodiment, the size limitation of the microparticles may include submicron to single digit micron size. This size range may prevent the microparticles that may backwash out of the site from causing an embolic hazard. In other embodiments, the cross-linking agent may be a functionalized surfactant free styrene latex microparticle. Several examples exist of these styrene microparticles. Examples of commercially available functional styrene microparticles are manufactured by Interfacial Dynamics Corporation and Magsphere.

Additionally, any one of these agents illustrated in FIGS. 17 and 18 may be accompanied by one or more contrast agent (block 1740) and/or suitable agent(s) (block 1750) for treatment of the region. The contrast agent or treatment agent may be conjugated to or dissolved into the structural component prior to introduction to the infarct area. The agents that may accompany the reinforcing component(s) may include, but are not limited to, angiogenic agents, ACE inhibitors, angiotensin receptor blockers, SRCA pump-increasing agents, phospholamban inhibitors and anti-apoptotic drugs. These agents may be in the form of small molecules, peptides, proteins or gene products. The small molecules may be optionally conjugated to a component of the solution, dispersed in solution, or dissolved in solution to improve the adhesion of the reinforcing components to the tissue. One embodiment is to conjugate a peptide with a conserved region that mediates adhesion processes. Another embodiment includes the use of a specific peptide conjugate with a RGD motif in the presence of the reinforcing component. In further embodiments, the RGD motif peptide comprises the following: von Willebrand factor, osteopontin, fibronectin, fibrinogen, vitronectin, laminin and collagen.

H. Prevention of Myocardial Edema and "Cementing" of the Infarct Region

Figure 19:
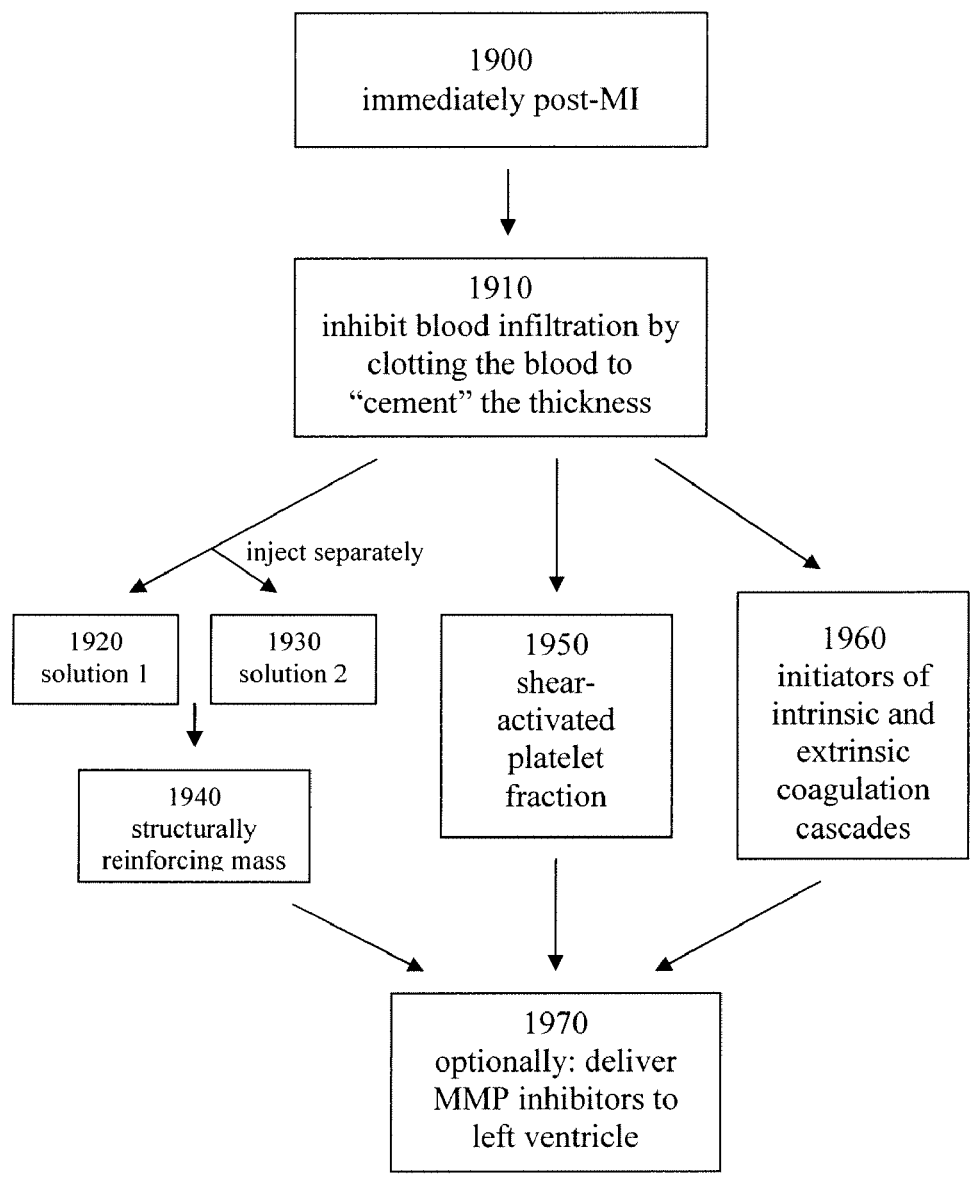
FIG. 19 illustrates various embodiments to clot the blood in an infarct region post MI.

FIG. 19 is a flowchart illustrating an alternative method to treat an infarct region of the ventricle (block 1900). One of the initial responses of the process post-MI is myocardial edema. The edema is composed of extravasated blood evident within a few hours after infarction. This is followed by its dissolution within the next few hours. The process that occurs immediately post-MI is that the infarct regional wall thickens and then thins. FIG. 19 illustrates the introduction of one or more clotting factors to the region thereby "cementing" the now clotted blood to reinforce the wall and thicken the wall (block 1910). FIG. 19 illustrates one method to clot the blood using a dual solution technique (blocks 1920/1930). In one embodiment, the first solution (block 1920) includes calcium chloride and thrombin and the second solution (block 1930) includes fibrinogen and tranexamic acid. Tranexamic acid is an anti-fibrinolytic agent. The introduction of these two solutions to the infarct region sequentially result in localized clotting of the blood that forms a structurally reinforcing mass (block 1940), e.g., fibrin glue, within the region preventing thinning of the infarct site. In another embodiment, intravenous pressure perfusion may be used to deliver the clot inducing solutions to the infarct zone. This prevents the possibility of the clot releasing into the arterial circulation. FIG. 19 illustrates the use of shear-activated platelet fraction to induce localized clotting (block 1950) This platelet fraction may be isolated from the MI subject's own blood or another source. FIG. 19 illustrates the use of other initiators of the clotting cascade (block 1960). These factors encompass factors that are termed intrinsic and extrinsic factors. Intrinsic factors initiate clotting in the absence of injury. Extrinsic factors initiate clotting that is caused by injury. In one embodiment, the clotting factor used to cease myocardial edema and reinforce the ventricular wall at the infarct zone may comprise the following: von Willebrand Factor (vWF), high molecular weight kininogen (HMWK), fibrinogen, prothrombin, and tissue factors III-X. In another embodiment, any combination of the clotting factors mentioned previously may be used that may provide increased tensile strength the infarct regional wall.

I. Matrix Metalloproteinase Inhibitors Use in the Infarct Region

After an MI injury occurs, macrophages tend to infiltrate the infarct region. The macrophages release matrix metalloproteinases (MMPs). As members of a zinc-containing endoproteinase family, the MMPs have structural similarities; however, each enzyme has a different substrate specificity, produced by different cells and additionally have different inducibilities. These enzymes cause destruction in the infarct zone. One important structural component destroyed by MMPs is the extracellular matrix (ECM). The ECM is a complex structural entity surrounding and supporting cells that are found within mammalian tissues. The ECM is often referred to as the connective tissue. The ECM is composed of three major classes of biomolecules: structural proteins, such as, collagen and elastin; specialized proteins, such as, fibrillin, fibronectin, and laminin; and proteoglycans. These are composed of a protein core to which is attached long chains of repeating disaccharide units termed of glycosaminoglycans (GAGs) forming extremely complex high molecular weight components of the ECM. Collagen is the principal component of the ECM and MMPs induce ECM degradation and affect collagen deposition. Inhibitors of MMP(s) (block 1970 of FIG. 19) exist and some of these inhibitors are tissue specific. It was previously demonstrated that acute pharmacological inhibition of MMPs, or in some cases a deficiency in MMP-9, that the left ventricle dilatation is attenuated in the infarct heart of a mouse. See Creemers, E., et al., *Matrix Metalloproteinase Inhibition After MI: A New Approach to Prevent Hear Failure?* Circ., 2001, pp. 201-210, 89. The inhibitors of MMPs are referred to as tissue inhibitors of metalloproteinases (TIMPs). Synthetic forms of MMPIs also exist, for example, BB-94, AG3340, Ro32-355b and GM 6001. It was previously shown that TIMPs reduce the remodeling in the left ventricle by reducing wall thinning. These experiments were performed on rabbits. In addition, this study also demonstrated that MMPI increases rather than decreases neovascularization in the sub-endocardium. See Lindsey, M. L., et al., *Selective Matrix Metalloproteinase Inhibitors Reduces Left Ventricular Remodeling but Does Not Inhibit Angiogenesis After Myocardial Infarction*, Circ., Feb. 12, 2002, pp. 753-758, 105(6). In one embodiment, TIMPs may be introduced to the infarct region to delay the remodeling process by reducing the migration of fibroblasts and deposition of collagen and prevent ECM degradation, reduce leukocyte influx and also reduce wall stress. In one embodiment, the TIMP may include the following: TIMP-1, TIMP-2, TIMP-3 and TIMP-4, which can be introduced to the infarct region in combination with the introduction of any of the described structurally reinforcing agents. In another embodiment, naturally occurring inhibitors of MMPs may be increased by exogenous administration of recombinant TIMPs. In another embodiment, the TIMP is a synthetically-derived TIMP introduced to the infarct region in combination with the introduction of any of the described structurally reinforcing agents. The introduction of TIMPs to the infarct zone may be accomplished by several different methods. It is critical that the introduction of these TIMP agents be accomplished by a minimally invasive technique. In one embodiment, TIMP agents will be introduced to the region by a minimally invasive procedure to prevent ECM degradation. An agent or dispersion will be introduced, in one embodiment, by multiple injections to the infarct region. This results in prevention of ECM degradation and increased strength to the regional wall. In one embodiment, the TIMP agent may be injected into the infarct zone during an open chest procedure or via a minimally invasive procedure. The minimally invasive procedure may include one of sub-xiphoid and percutaneous methods. In another embodiment, the percutaneous introduction into the infarct zone may include one of intra-ventricular needle, transvascular needle catheter and retrograde venous perfusion. In addition, the TIMP agents may be introduced via suspension or sustained release formula, for example, introduced in microparticles detailed in the three-component system of FIG. 6. In one embodiment, the introduction of TIMPs may follow any of the cross-linking events that prevent collagen slippage (see FIG. 18). In another embodiment, the cross-linking agent may be cleared from the targeted infarct area prior to introducing the TIMP(s).

After an MI, the myocardium may be significantly affected resulting in a percentage of the tissue being akinetic or dyskinetic. This often occurs when the MI is caused by an occluded left anterior descending artery. Moderate infarct where 20 to 40 percent of the tissue is affected decreased cardiac output occurs resulting in the activation of the neuron-hormonal system (via a renin-angiotensin-aldosterone system). Thus, the neuron-hormonal activation causes an increase in blood pressure resulting in further stress to the myocardium. The induced necrosis results in an inflammatory response that clears the site of the necrotic tissue and ultimately leads to thinning of the myocardium. The cycle continues with an increase in stress on the myocardium and may result ultimately in heart failure.

J. Structural Reinforcement of the Infarct Zone by Inducible Gel Systems

Figure 20:
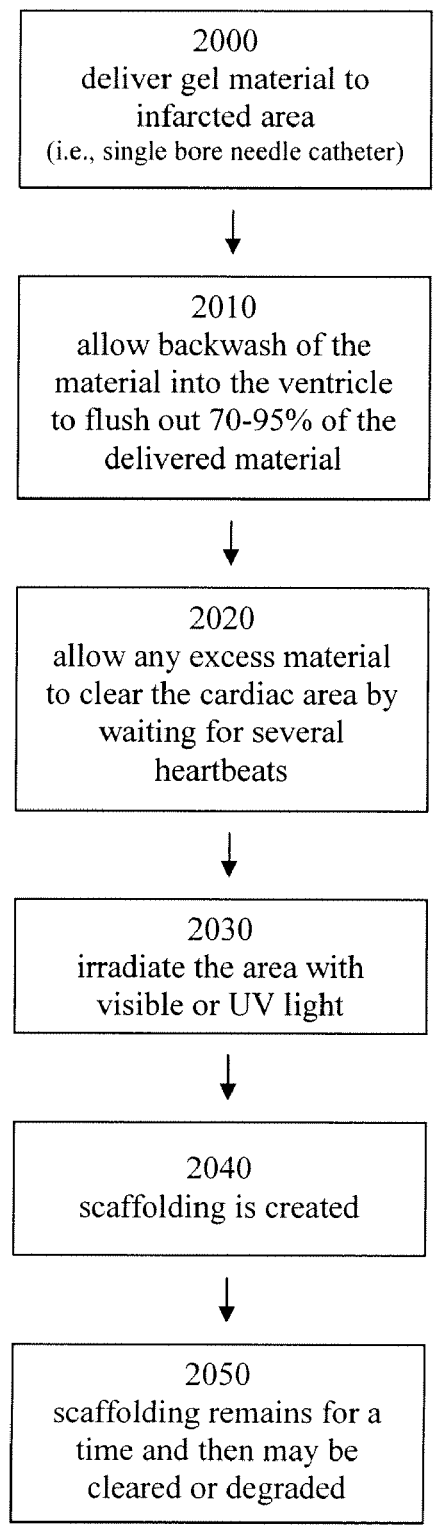
FIG. 20 illustrates various methods to reinforce an infarct region using light sensitive components.

FIG. 20 is a flowchart illustrating an alternative method to structurally reinforce the infarct region of the ventricle. A photo-polymerizable hydrogel may be administered to the infarct region (block 2000) for structural reinforcement of the infarct zone. Hydrogels have been used before in tissue engineering applications. These gels are biocompatible and do not cause thrombosis or tissue damage. These hydrogels may be photo-polymerized in vivo and in vitro in the presence of ultraviolet (UV) or visible light depending on the photoinitiation system. Photo-polymerizing materials may be spatially and temporally controlled by the polymerization rate. These hydrogels have very fast curing rates. A monomer or macromer form of the hydrogel may be introduced to the infarct zone for augmentation with a photoinitiator. Examples of these hydrogel materials include PEG acrylate derivatives, PEG methacrylate derivatives or modified polysaccharides. After administration to the infarct region, backwash of the material into the ventricle to flush 70-95% of the delivered material may be allowed (block 2010) and any excess material to clear the cardiac area by waiting for several heartbeats may be allowed (block 2020).

Visible light (block 2030) may be used to initiate interfacial photopolymerization of a polyoxyethylene glycol (PEG)-co-poly(alpha-hydroxy acid) copolymer 2100 based on PEG 8000 macromonomer in the presence of an initiator, for example, Quantacure QTX. Initiator 2-hydroxy-3-[3,4,dimethyl-9-oxo-9H-thioxanthen-2-yloxy] N,N,N-trimethyl-1-propanium chloride photo-initiator may be obtained as Quantacure QTX. This is a specific water-soluble photoinitiator that absorbs ultraviolet and/or visible radiation and forms an excited state that may subsequently react with electron-donating sites and may produce free radicals. This technology has been used to demonstrate adherence to porcine aortic tissue, resulting in a hydrogel barrier that conformed to the region of introduction. The resulting matrix was optimized in vitro and resulted in the formation of a 5-100 microns thick barrier. See Lyman, M. D., et al., *Characterization of the Formation of Interfacially Photopolymerized Thin Hydrogels in Contact with Arterial Tissue*, Biomaterials, February 1996, pp. 359-364, 17(3). Scaffolding (block 2040) may be directed to only the desired area of the ventricle using minimally invasive procedures discussed previously. The structural reinforcement could remain in place until it is cleared or degraded (block 2050).

One embodiment includes introduction to the infarct zone of benzoin derivatives, hydroxalkylphenones, benziketals and acetophenone derivatives or similar compounds. These photoinitiators form radicals upon exposure to UV light by either photo-cleavage or by hydrogen abstraction to initiate the reaction (see FIGS. 21A-21E). The source of the UV or visible light may be supplied by means of catheter 2160, such as a fiber optic tip catheter, or lead on a catheter, or transdermally. FIGS. 22A-22B illustrates a catheter assembly that may be used to deliver a light-sensitive material. The catheter 2210 is designed to provide a delivery device with at least one lumen for one or more agent(s) 2230 and a light source 2220 for modification of the delivered agent. The catheter controller 2240 may house a switch 2250 for the light source 2220 and a controller for agent delivery 2260. In another embodiment, the photoinitiator camphorquinone may be used. Camphorquinone has been used extensively in dental applications and has a $\lambda_{max}$ of 467 nanometers. For example, this agent can be activated by a GaN blue LED on the tip of a catheter. One embodiment includes the use of visible light at the end of the delivery catheter to induce the polymerization event in the presence of a light sensitive initiator. Another embodiment includes the use of the photoinitiator camphorquinone which may facilitate the cross-linking of the hydrogel by a light on the tip of a catheter within the infarct region. Another embodiment includes the use of the photoinitiator Quantacure QTX which facilitates the cross-linking of the hydrogel by a light on the tip of a catheter within the infarct region. Another embodiment includes the use of a catheter with a UVA light source to induce the polymerization event in the presence of a light sensitive initiator. Other initiators of polymerization in the visible group include water-soluble free radical initiator 2-hydroxy-3-[3,4,dimethyl-9-oxo-9H-thioxanthen-2-yloxy] N,N,N-trimethyl-1-propanium chloride. This cascade of events provides the necessary environment for initiation of polymerization of suitable vinyl monomers or pre-polymers in aqueous form within the infarct region. See Kinart, et al., *Electrochemical Studies of 2-hydroxy-3-(3,4-dimethyl-9-oxo-9H-thioxanthen-2-yloxy)N,N,N-trimethyl-1-propanium chloride*, J. Electroanal. Chem., 1990, pp. 293-297, 294.

One possible method of introducing a photo-polymerizable agent to the infarct region is illustrated in FIGS. 21A-21E. In one embodiment, the photo-polymerizable material is introduced to the infarct region during an open chest procedure 2130 or via a minimally invasive procedure. A minimally invasive procedure includes sub-xiphoid and percutaneous methods. In another embodiment, the percutaneous introduction into the infarct zone may comprise one of the following: intra-ventricular needle, transvascular needle catheter and retrograde venous perfusion. A single bore needle catheter 2120 may be used to introduce the photo-polymerizable material into the infarct zone 2110 resulting in treated infarct zone 2140. Once the agent is introduced to the region, several heartbeats clear the excess agent into the ventricle 2150, and this excess agent is cleared from the cardiac region. Once the excess material is cleared, light source 2160 may be introduced to induce polymerization 2170. Thus, the structural reinforcement is confined to the local area of damage where tissue augmentation is required. As illustrated in FIG. 20, the scaffolding may be made up of a resistant material or a biodegradable material (block 2050). Some examples of biodegradable materials include PEG-co-poly α-hydroxy acid) diacrylate macromers, derivatives of this material that vary the length and composition of the α-hydroxy acid segment in the co-polymer, poly(propylene fumarate-co-ethylene)glycol and hyaluronic acid derivatives. The degradation rates of the polymers may be varied according to the optimum length of time the material is required to remain in the infarct region. It has been shown that the degradation rates of theses gels can be modified by the appropriate choice of the oligo(α-hydroxy acid) from less than one day to as long as 4 months. See Sawhney, A. S., et al., *Bioerodable Hydrogels Based on Photopolymerized Poly(ethylene glycol)-co-poly(a-hydroxy acid) Diacrylate Macromers*, Macromolecules, 1993, pp. 581-587, 26. Any of these polymer chains may be formed in the presence of a photoinitiator, such as Quantacure QTX, and a light source.

Figure 21A:
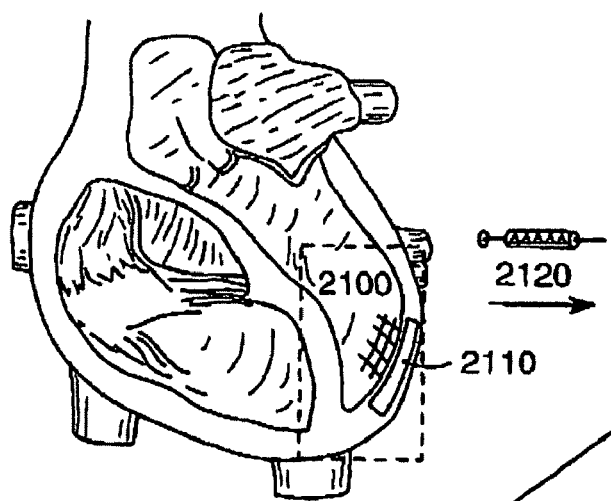
FIGS. 21A-21E illustrates a cross-sectional view of introduction of an embodiment using a photo-polymerizable component of FIG. 20 to an infarct region.
Figure 21B:
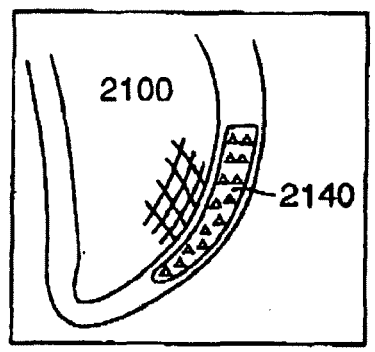
Figure 21C:
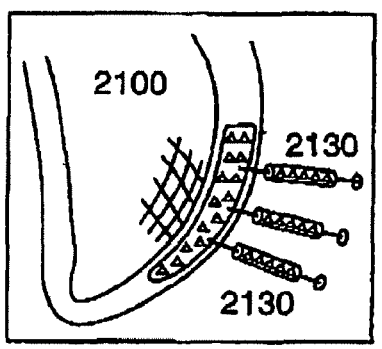
Figure 21D:
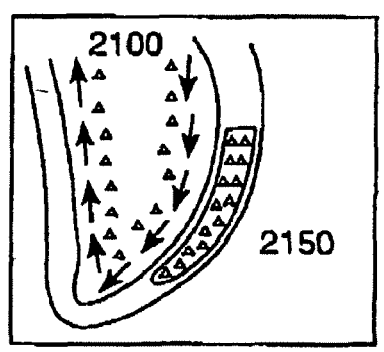
Figure 21E:
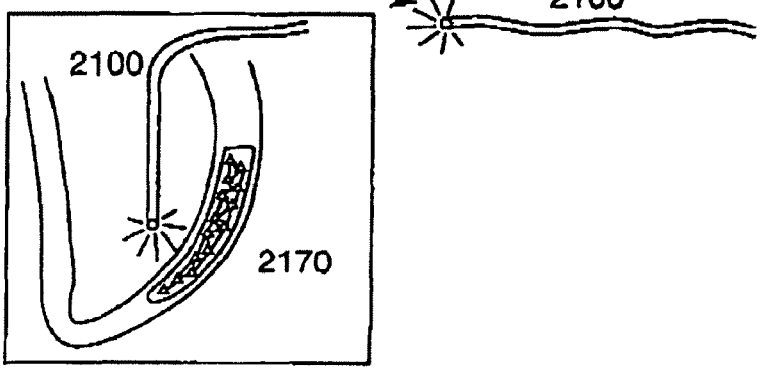
Figure 22A:
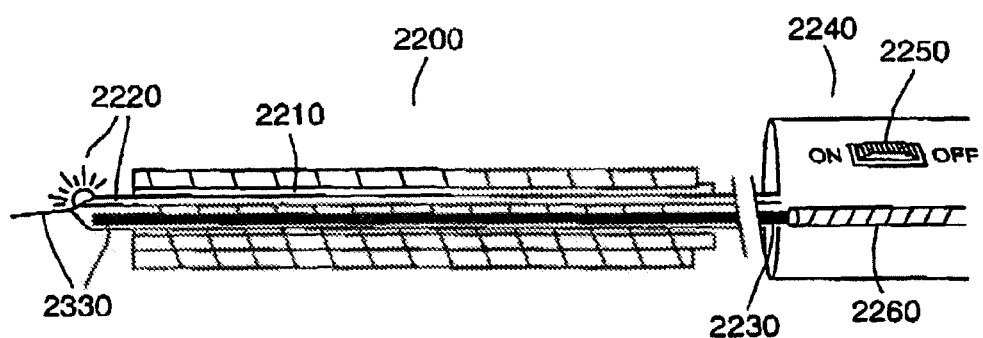
FIG. 22A illustrates a longitudinal view of a catheter device that has a light source and at least one component lumen.
Figure 22B:
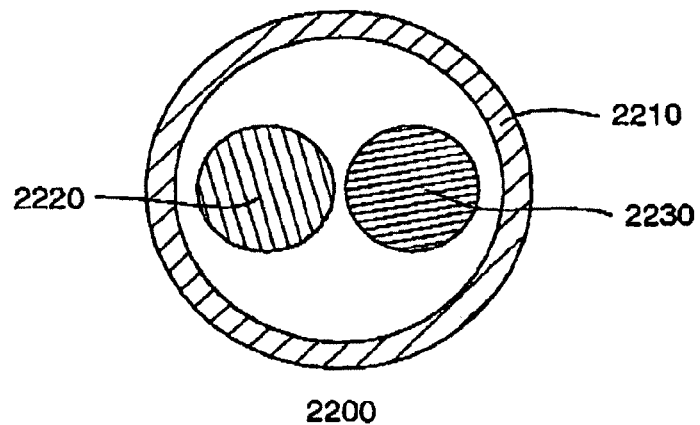
FIG. 22B illustrates a cross-sectional view of a catheter device that has a light source and at least one component lumen.
Figure 23:
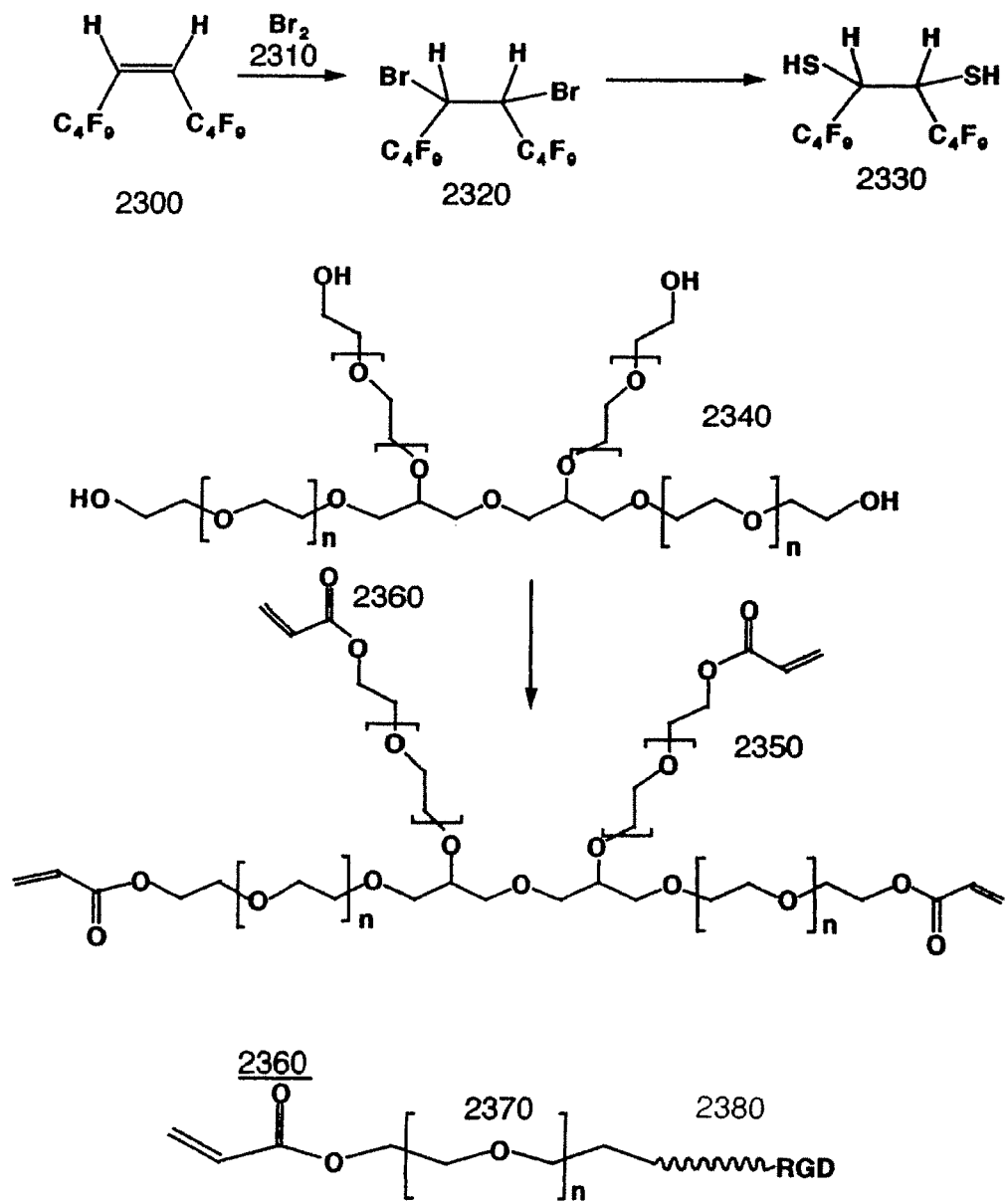
FIG. 23 illustrates one example of a multi-component method to reinforce the infarct region and/or re-oxygenate the infarct region.

FIGS. 21A-21E illustrates the process of introduction of a photo-polymerizable material to the infarct zone. FIG. 21A and FIG. 21B illustrates the introduction of the material to the treatment site 2100 at the infarct region 2110. FIG. 21C illustrates the clearing of the excess material into the ventricle 2150. Then, in FIG. 21D the light source may be introduced via a catheter to polymerize the material 2160. The material remains in the site 2170 as structural reinforcement until at which time it degrades or not depending on the material used.

In one embodiment, any of the described agents may be introduced in one or more doses in a volume of about 1 µL to 1 mL. In another embodiment, any of the described agents may be introduced in one or more doses in a volume of about 1 µL to 300 µL. In another embodiment, any of the described agents may be introduced in one or more doses in a volume of about 1 µL to 100 µL. In a preferred embodiment, the any of the described agents may be introduced in one or more doses in a volume of about 1 µL to 50 µL.

Figure 24A:
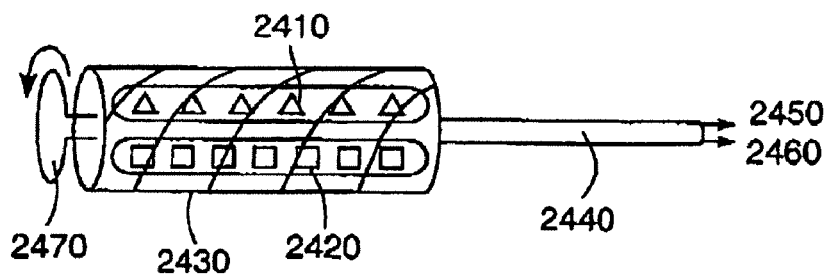
FIG. 24A illustrates a longitudinal view of a catheter device that has two delivery ports and a control mechanism to deliver one component prior to the second component.
Figure 24B:
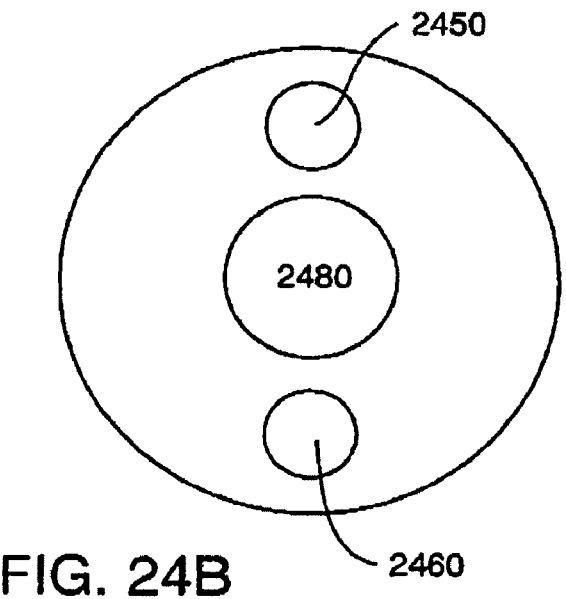
FIG. 24B illustrates a front view of the distal end of a catheter device with two delivery ports.
Figure 24C:
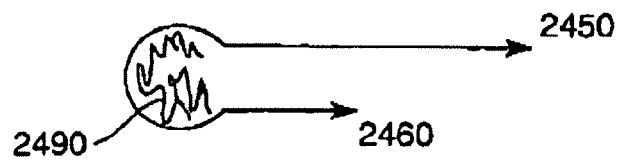
FIG. 24C illustrates the distal end of a catheter device where one delivery port may be extended while the second port may be confined to the housing of the catheter.

FIGS. 24A-24B illustrate a catheter assembly that may be used to deliver a dual component composition. In FIG. 24A, component one 2410 and component two 2420 are housed 2430 in separate lumens of a delivery device. Delivery of the components is controlled by a handle 2470 at the base of the assembly. Handle 2470 may be rotated to allow one needle to extend and then the other. In one embodiment, only one needle is engaged at a time. A cross-sectional view illustrated in FIG. 24B illustrates first needle port 2450 and second needle port 2460 and central tendon 2480 that controls the needle extension. At distal end 2490 of the assembly, (see FIG. 24C), the handle is turned and the needle extends while retracting the other needle. In one embodiment, this catheter assembly may be used to deliver components to the infarct region of a left ventricle intra-myocardially. In another embodiment, this catheter device may be used to deliver a first component to the area and a second component after the excess first component is allowed time to wash away.

FIGS. 25A-25D illustrate the introduction of dual components using the catheter device of FIG. 24 to an infarct region while avoiding the possibility of injecting the agents into the exact same site. The delivery device of FIG. 24 may be used to deliver the components to the infarct region. The infarction is illustrated as a region between endocardium 2520 and epicardium 2510. Device 2540 is advanced to this site and the first component is delivered by extending first needle 2550 dispersing component 2560 throughout area 2530. Then, first needle 2550 is retracted while second needle 2570 is extended. Second component 2580 is thereby dispersed throughout area 2530. The delivery of the two components to area 2530 is capable of forming gel 2590.

Figure 26:
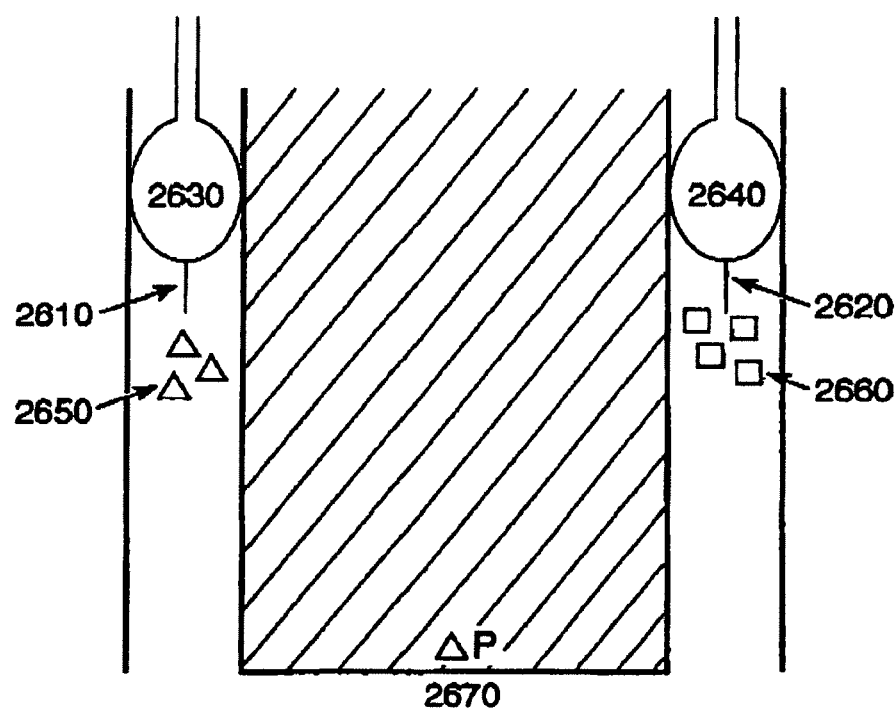
FIG. 26 illustrates the introduction of one component through a vein and the second through an artery using the catheter with retractable dual delivery ports.

FIG. 26 illustrates an embodiment of the delivery of the catheter device illustrated in FIGS. 24 and 25. Both of components 2650 and 2660 are delivered through a lumen of a catheter (for example, a balloon catheter) 2630/2640 at the same time. For example, first component 2650 may be delivered through a venous route 2610 and second component 2660 may be delivered through an arterial route 2620. This procedure ensures the appropriate pressure balance to contain the components in the microcirculation. This avoids leakage to either the venous or arterial side. The driving pressure 2670 for the venous side is greater than 100 mm Hg ($\Delta P$) and is calculated to ensure the confinement of the component at capillary level. The arterial side does not require an external pressure gradient. The arterial side may be accomplished by infusion. In one embodiment, the catheter may be used to deliver the first component through the venous tree followed by the second component through the arterial tree. This device may be used to deliver any of the component combination methods described in the embodiments detailed previously.

K. Ventricular Plugs

Another method for reinforcing the damaged wall of a ventricle may include introduction of a solid material to the damaged area. The solid material may be used to fill or bulk the region by introducing plugs of the solid material to the site and may increase the compliance of the ventricle. These materials may be made of organic or silicon-based polymers, biodegradable polymers, non-biodegradable polymers, engineered biomaterials and/or metals. In one embodiment, the plug may have barbs or pointed ends in order to lodge the material into the area and ensure it remains there. In other embodiments, the sealant or plug may add bulk to the thinning wall of an infarct post myocardial infarction. This may result in an increase in the modulus of elasticity of the damaged area. In other embodiments, the sealant or plug may invoke an inflammatory response to the infarct region. The inflammatory response will result in the increase in angiogenic response capable of causing recruitment and activation of fibroblasts that deposit additional collagen to bulk the thinning infarct region and increase the modulus of elasticity of this region. Still, other embodiments include the addition of a plug to the damaged region of a ventricle that may add strength to the wall and also cause an inflammatory response to the region.

In one embodiment, the plug supplied to the damaged region of the ventricle may include biocompatible organic components. In other embodiments, the plug supplied to the damaged region of the ventricle may include a biocompatible silicone-based polymer. In other embodiments, the plug supplied to the damaged region of the ventricle may include biocompatible biodegradable polymers for example PLGA, Poly(hydroxyvalerate) and poly ortho esters. In other embodiments, the plug supplied to the damaged region of the ventricle may include biocompatible non-biodegradable material, for example, polypropylene and PMMA. In still further embodiments, the plug supplied to the damaged region of the ventricle may include biocompatible metal compounds, for example, 316L, Co—Cr alloy, tantalum and titanium. Another advantage to using a plug directly implanted in the region of interest may be to add additional surface components to the plug such as side groups. These side groups may contain reactive side groups that react with exogenously supplied or endogenous collagen, for example, type I and type III collagen. Since collagen contains a significant number of lysine and hydroxyproline residues, these residues harbor primary amine and hydroxyl groups capable of reacting with other moieties. In one embodiment, the plug supplied to the damaged region of the ventricle may include surface aldehyde groups capable of reacting with the primary amines of lysine in collagen.

The size and the shape of the plugs may vary depending on the situation. For example, polymeric plugs mentioned previously may be machined, injection molded, extruded or solution cast. In one embodiment, the shape of the plug may be elongated and thin in order to facilitate delivery by a catheter device. These plugs may also possess a barb or side protrusion to prevent the plug from slipping out of the site once it is introduced to the damaged region of the ventricle. In other embodiments, the plug may be created in the shape similar to a screw or a helix. In one embodiment, the plug may be a polymeric material. In other embodiments, the plug may be a polymeric material with SS anchors for example, a plug with a stainless steel band with anchors for embedding the plug into the site of interest. The size of the plug may also vary. In one embodiment, the radial diameter of the plug may be from about 0.1 mm to about 5 mm. In other embodiments, the radial diameter of the plug may be about 0.2 mm to about 3 mm. In other embodiments, the length of the plug may be from about 1 mm to about 20 mm. In other embodiments, the length of the plug may be about 2 mm to about 12 mm. In addition to the size and shape of the plug, the number of plugs supplied to a region in the ventricle may also vary depending on the extent of damage and the condition of the subject. In one embodiment, the number of plugs supplied to the region may about 1 to about 200. In other embodiments, the number of plugs supplied to the region may be about 5 to about 50. In still further embodiments, the number of plugs supplied to the region may be about 2 to about 20.

In a preferred embodiment, the plug may be a processed biocompatible biomaterial. This biomaterial may be advantageous for recruiting cells to the damaged region for additional strength to the site. One example of a biomaterial includes porcine-derived small intestine submucosa (SIS). This engineered biomaterial may be supplied from DePuy Inc and the Cook Group. It is available in sterile sheets. SIS includes the complete small intestinal sub-mucosa, including de-cellularized extracellular matrix (ECM) in a native configuration. It also includes important endogenous growth factors adhered to the matrix. SIS has previously been shown to recruit pluripotent bone marrow-derived stem cells that adhere to the SIS and induce healing. SIS has previously been used to repair rotator cuff injuries, diabetic foot ulcers and hip joints. SIS has been shown to re-absorb after a period of approximately 3 to 4 months. After re-absorption, the healed live tissue has replaced the matrix. In one embodiment, small disks of SIS may be supplied to a region in the ventricle for example an infarct region. The SIS disks may provide similar recruitment of cells into the damaged myocardium. These cells may then transform into viable muscle tissue and may form contractile myocytes.

There are several methods that may be used to introduce any of the plugs described. An optimum approach for introduction of the plugs may include, but is not limited to, introduction to the infarct region and/or the border zone of an infarct region during an open-heart procedure. Alternatively, introduction through a minimally invasive procedure such as sub-xiphoid or percutaneous methods using an intra-ventricular catheter or transvascular catheter (venous or arterial) may be used. One embodiment for introducing the plugs to the infarct region may include directly introducing the plugs to the site during an open-heart surgical procedure.

One or more contrast agents and/or suitable treatment agent(s) may accompany the previously detailed components. The contrast agent or treatment agent may be dispersed into, conjugated to, or dissolved into the plug component prior to introduction to the infarct area. The contrast agents may be used for detection in X-ray or MR analysis. The agents that may accompany the reinforcing component(s) may include, but are not limited to angiogenic agents, ACE inhibitors, angiotensin receptor blockers, SRCA pump-increasing agents, phospholamban inhibitors and anti-apoptotic drugs. These agents may be in the form of small molecules, peptides, proteins or gene products. The agents may be optionally conjugated to a component of the resin mix that makes the plug, dispersed in the plug solution prior to forming the plug, or dissolved in the plug solution prior to forming the plug, or packed into machined pockets or reservoirs in the plug to elicit a biological effect (e.g., improve implant adhesion, recruit cells, promote healing). One embodiment is to conjugate a peptide with a conserved region that mediates adhesion processes. Another embodiment includes the use of a specific peptide conjugate with a RGD motif or the peptide receptor to RGD, such as aspartate-aspartate-methionine (DDM) in the presence of the reinforcing component. In further embodiments, the RGD motif peptide may include von Willebrand factor, osteopontin, fibronectin, fibrinogen, vitronectin, laminin and collagen.

In the foregoing specification, the embodiments have been described with reference to specific exemplary embodiments. It will, however, be evident that various modifications and changes may be made without departing from the broader spirit and scope of the invention as detailed in the appended claims. The specification and drawings are, accordingly, to be regarded in an illustrative rather than a restrictive sense.

EXAMPLES

Example 1

Example 1 illustrates one possible three-component system described in FIG. 7 to treat a myocardial infarction. A cross-linking functionality can be synthesized starting from a fluorinated molecule with an ethylene functionality as in FIG. 22. Bromine 2310 is added to a fluoronated molecule 2300. Reduced thiols rapidly replace the bromine groups forming a di-functional thiol component 2320. The di-functional thiol 2330 can then react with a tetra-acryloyl(polyethylene glycol) 2340 and a di-functional polyethylene glycol with both the thiol functionality and the RGD 2380 peptide sequence. The tetra-acryloyl(polyethylene glycol) can be obtained from Shearwater Polymers as a specialty polymer (product number 0J0000D04; $M_r$=2,000 with each arm having a molecular weight of 500 g/mol or ~15 PEG sequences long). It is generated by the reaction of the tetra-hydroxyl terminated polyethylene glycol and acryloyl in the presence of a tertiary amine.

The third component is a peptide binding sequence 2350 with a polyethylene glycol functionality. The polyethylene glycol spacer 2370 must be longer then the spacer functionality of the other two components to prevent steric hindrance of the matrix components and ensure bio-availability of the peptide binding sequence. In this mixture of these three components, the average functionality must be two or greater to ensure desired gel formation.

In order to use this component system for the treatment of an MI, an aliquot of acryloyl functionalities are diluted in water, preferably with a basic pH. Then the aliquot is added to a syringe that feed a bore of a dual-bore needle (described previously). The thiol component is then added to a syringe that controls the second bore of the dual bore syringe. The two components with acryloyl functionalities and thiol functionalities are added simultaneously to the infarct region via the dual bore system or via a catheter. The components come in contact with one another at the site and form a gel network with a high oxygen carrying capability.

Example 2

Example 2 incorporates all of the components of Example 1 with an additional component. Adult skin cells capable of differentiating into cardiomyocytes are added to the second component, a perfluoronated compound. The cells may be injected along with the perfluoronated thiol. This would result in the formation of a hydrogel capable of supporting the oxygen demands of the cell. In addition the gel would swell by taking up fluids, provide nutrients for the cells and is capable of eliminating cellular wastes as well as serving as a cellular scaffold for deposition of the fibroblasts. Other sources of cells that could be delivered and survive may include but are not limited to adult, fetal and embryonic stems cells (e.g., mesenchymal, skeletal myoblast cells).

Example 3

Example 3 illustrates the use of gel introduction to the infarct region of a deceased rat heart. Ex vivo rat hearts were obtained and the hearts were mapped for the infarct region. Less than 30 microliters of material were injected into the infarct region. An agent, 10% poly (allyl amine) hydrochloride (3.1 grams) plus 35% poly(acrylic acid) (0.7 grams) system is protonated, resulting in a stable aqueous solution was maintained at pH 3.0 within the catheter until it reached the targeted area. The solution was injected into 10% gelatin gel in phosphate-buffered saline. The injectate gels instantly. The same injectate was used on the ex-vivo rat heart. The injectate gelled instantly at the infarct region.

Example 4

Sprague-Dawley rats were infarcted by an open chest procedure, ligature on LAD. Survived for 7 days to allow scar formation, then sacrificed. Hearts removed and packed in ice cold PBS. The hearts were injected in infarct region by a 1 cc syringe, 30-gauge needle. The following polymers were used in the infarct region: (1) PLGA (Birmingham Polymers), a 20% solution in diglyme, with 0.6% Sudan Red B was introduced. It was injected into infarcted wall. The tissue swells immediately and then the solution precipitates in the infarct region; (2) poly(butyl methacrylate co-methyl methacrylate. Mr=100,000 daltons (Aldrich), a 20% solution in diglyme, with 1% Fat Brown RR. It was injected into infarcted wall. The tissue swells immediately and then the solution precipitates in the infarct region; (3) a 3.1 gram aliquot of a 10% solution of poly(allyl amine) (Aldrich) was mixed with 0.7 grams of 35% poly(acrylic acid) in water (Aldrich). In addition, 1% Toluidine blue was added to the solution. This composition was injected into infarcted wall. The tissue swells immediately and the solution precipitates. Histology sections (10 micron sliced) demonstrated that the dyed polymers precipitated within the infarct tissue in the infarct region.

What is claimed is:

1. A kit, comprising:
   a first container having (i) hyaluronic acid or a salt thereof, the hyaluronic acid or a salt thereof having a zero-shear viscosity of between 3,000,000 mPa-s and 7,000,000 mPa-s at rest at a physiological temperature in a buffer solution, and (ii) at least one cell type; and
   a second container having one of plasma or a plasma product wherein the contents of the first container and the second container are designed for admixing thereof to form a single component bioscaffolding when administered to a treatment site.

2. The kit of claim 1 wherein the cell type is selected from the group consisting of localized cardiac progenitor cells, mesenchymal stem cells, cardiac stem cells, bone marrow derived mononuclear cells, adipose-derived stem cells, embryonic stem cells, umbilical cord blood derived stem cells, smooth muscle cells, and skeletal myoblasts and an amount of cells in the first container is in a range from about 0.5 million to about 100 million.

3. The kit of claim 2 wherein an amount of cells in the first container is about 20 million.

4. The kit of claim 1 wherein the hyaluronic acid or a salt thereof: has a molecular weight of at least 4 million Daltons; is in a solution at a concentration between 10 mg/mL and 23 mg/mL; and is derived from rooster combs or a fermentation process.

5. The kit of claim 1 wherein the ratio of the hyaluronic acid or salt thereof to the plasma or plasma product is between 5:95 and 95:5.

6. The kit of claim 1 wherein the buffer is phosphate buffered saline and the plasma or plasma product is one of refrigerated plasma, fresh frozen plasma, platelet-enriched plasma, or dried plasma.

7. The kit of claim 1 wherein the first container further comprises one of: at least one hydrogel different from hyaluronic acid or a salt thereof blended, composited, or covalently grafted or linked to the hyaluronic acid or salt thereof; at least one growth factor; or at least one growth factor encapsulated within a bioerodable carrier.

8. A composition, comprising:
   a solution comprising hyaluronic acid or a salt thereof in a buffer, the solution having the following characteristics: the hyaluronic acid or a salt thereof is present in an amount of between 10 milligrams/mL and 23 milligrams/mL; the hyaluronic acid or a salt thereof has a shear viscosity of between 3,000,000 mPa-s and 7,000,000 mPa-s at a physiological temperature; the hyaluronic acid or a salt thereof has a molecular weight of at least 4 million Daltons;
   a suspension including at least one cell type admixed with the solution wherein a ratio of the suspension to the solution is one of 1:1, 2:3, or 1:3; and
   a plasma or a plasma product admixed with the solution.

9. The composition of claim 8 wherein the cell type is selected from the group consisting of localized cardiac progenitor cells, mesenchymal stem cells, cardiac stem cells, bone marrow derived mononuclear cells, adipose-derived stem cells, embryonic stem cells, umbilical cord blood derived stem cells, smooth muscle cells, and skeletal myoblasts and an amount of cells in the suspension are in a range from about 0.5 million to about 100 million.

10. The composition of claim 8 wherein the hyaluronic acid or a salt thereof is in a solution and the solution further comprises one of: at least one hydrogel different from hyaluronic acid or a salt thereof blended, composited, or covalently grafted or linked to the hyaluronic acid or salt thereof; at least one growth factor; or at least one growth factor encapsulated within a bioerodable carrier.

* * * * *